US010329542B2

(12) United States Patent
Tavis et al.

(10) Patent No.: US 10,329,542 B2
(45) Date of Patent: Jun. 25, 2019

(54) HBV RNASE H PURIFICATION AND ENZYME INHIBITORS

(71) Applicant: Saint Louis University, St. Louis, MO (US)

(72) Inventors: John Tavis, St. Louis, MO (US); Yuan Hu, St. Louis, MO (US)

(73) Assignee: Saint Louis University, St. Louis, MO (US)

( * ) Notice: Subject to any disclaimer, the term of this patent is extended or adjusted under 35 U.S.C. 154(b) by 0 days.

(21) Appl. No.: 15/670,008

(22) Filed: Aug. 7, 2017

(65) Prior Publication Data

US 2017/0335296 A1 Nov. 23, 2017

Related U.S. Application Data

(62) Division of application No. 14/647,331, filed as application No. PCT/US2013/072201 on Nov. 27, 2013, now abandoned.

(60) Provisional application No. 61/821,623, filed on May 9, 2013, provisional application No. 61/730,344, filed on Nov. 27, 2012.

(51) Int. Cl.

| | |
|---|---|
| *C12N 9/12* | (2006.01) |
| *C12N 9/22* | (2006.01) |
| *C12Q 1/48* | (2006.01) |
| *C12Q 1/68* | (2018.01) |
| *A61K 38/21* | (2006.01) |
| *A61K 31/513* | (2006.01) |
| *A61K 31/5377* | (2006.01) |
| *A61K 31/519* | (2006.01) |
| *C12Q 1/70* | (2006.01) |
| *C12Q 1/34* | (2006.01) |

(52) U.S. Cl.
CPC .............. *C12N 9/12* (2013.01); *A61K 31/513* (2013.01); *A61K 31/519* (2013.01); *A61K 31/5377* (2013.01); *A61K 38/21* (2013.01); *C12N 9/22* (2013.01); *C12Q 1/34* (2013.01); *C12Q 1/485* (2013.01); *C12Q 1/68* (2013.01); *C12Q 1/706* (2013.01); *C12Y 207/00* (2013.01); *C12Y 301/26004* (2013.01); *G01N 2333/922* (2013.01)

(58) Field of Classification Search
None
See application file for complete search history.

(56) References Cited

U.S. PATENT DOCUMENTS

| | | |
|---|---|---|
| 5,968,781 A | 10/1999 | Yoon et al. |
| 7,572,579 B2 | 8/2009 | Yoshinaga et al. |

| | | |
|---|---|---|
| 2010/0130505 A1 | 5/2010 | Smrcka et al. |
| 2011/0021464 A1 | 1/2011 | Lanier et al. |
| 2014/0227729 A1 | 8/2014 | Subramanian et al. |

FOREIGN PATENT DOCUMENTS

WO    WO 2012/040204    3/2012

OTHER PUBLICATIONS

"Affinity His-Tag Purification—Procedure for Use Chelating Agarose NTA Beads Bulk Resins," ABT, available from www.brunschwig-ch.com/pdf/downloads/ABT_NTAProcedure.pdf, 10 pages, 2011.
"Proteus IMAC Handbook: Mini and Midi spin columns," Pro-Chem, Inc., 58 pages.
Arauz-Ruiz et al., "Genotype H: a new Amerindian genotype of hepatitis B virus revealed in Central America," *J. Gen. Virol.*, 83(8):2059-2073, 2002.
Arnold et al., "Poliovirus RNA-dependent RNA polymerase (3DP$^{pol}$). Divalent cation modulation of primer, template, and nucleotide selection," *J Biol Chem*, 274:37060-37069, 1999.
Beck and Nassal, "Efficient Hsp90-independent in vitro activation by Hsc70 and Hsp40 of duck hepatitis B virus reverse transcriptase, an assumed Hsp90 client protein," *J Biol Chem*, 278:36128-36138, 2003.
Billamboz et al., "2-Hydroxyisoquinoline-1,3(2H,4H)-diones as inhibitors of HIV-1 integrase and reverse transcriptase RNase H domain: influence of the alylation of position 4," *European Journal of Medicinal Chemistry*, 46:535-546, 2011.
Billamboz et al., "Design, synthesis, and biological evaluation of a series of 2-hydroxyisoquinoline-1,3(2H,4H)-diones as dual inhibitors of human immunodeficiency virus type 1 integrase and the reverse transcriptase RNase H domain," *J Med Chem*, 51:7717-7730, 2008.
Billamboz et al., "Magnesium chelating 2-hydroxyisoquinoline-1,3(2H,4H)-diones, as inhibitors of HIV-1 integrase and/or the HIV-1 reverse transcriptase ribonuclease H domain: discovery of a novel selective inhibitor of the ribonuclease H function," *J Med Chem*, 54:1812-1824, 2011.
Cai et al., "Hepatitis B virus replication is blocked by a 2-hydroxyisoquinoline-1,3(2H,4H)-dione (HID) inhibitor of the viral ribonuclease H activity," *Antiviral Research*, 108:48-55, 2014.
Cao et al., "Recent progress in the research of small molecule HIV-1 RNase H inihibtors," *Current Medicinal Chemistry*, 21:1956-1967, 2014.
Chang et al., "Effects of insertional and point mutations on the functions of the duck hepatitis B virus polymerase," *J Virol*, 64:5553-5558, 1990.
Chang et al., "Phenotypic mixing between different hepadnavirus nucleocapsid proteins reveals C protein dimerization to be cis preferential," *J Virol.*, 68(8):5225-5231, 1994.
Chen et al., "Selected mutations of the duck hepatitis B virus P gene RNase H domain affect both RNA packaging and priming of minus-strand DNA synthesis," *J Virol*, 68:5232-5238, 1994.
Chen et al., "The design, synthesis and biological evaluations of C-6 or C-7 substituted 2-hydroxyisoquinoline-1,3-diones as inhibitors of hepatitis C virus," *Bioorganic & Medicinal Chemistry*, 20:467-479, 2012.

(Continued)

*Primary Examiner* — Stacy B Chen
(74) *Attorney, Agent, or Firm* — Parker Highlander PLLC

(57) ABSTRACT

Provided herein are methods for the obtention of an active HBV RNaseH preparation and its use in screening methods to identify potential inhibitors of the enzyme for possible use as therapeutic agents. Also provided are methods of treatment using agents identified according to the screen.

20 Claims, 28 Drawing Sheets

Specification includes a Sequence Listing.

(56) References Cited

OTHER PUBLICATIONS

Choi et al., "Expression of the active human and duck hepatitis B virus polymerases in heterologous system of Pichia methanolica," *Antiviral Res*, 55:279-290, 2002.

Esposito and Tramontano, "Past and future. Current drugs targeting HIV-1 integrase and reverse transcriptase-associated ribonuclease H activity: single and dual active site inhibitors," *Antivir Chem Chemother*, 23(4):129-144, 2014.

Gerelsaikhan et al., "Hepatitis B virus nucleocapsid envelopment does not occur without genomic DNA synthesis," *J Virol*, 70:4269-4274, 1996.

Hu and Anselmo, "In vitro reconstitution of a functional duck hepatitis B virus reverse transcriptase: posttranslational activation by Hsp90," *J Virol*, 74:11447-11455, 2000.

Hu and Seeger, "Hsp90 is required for the activity of a hepatitis B virus reverse transcriptase," *Proc Natl Acad Sci USA*, 93:1060-1064, 1996.

Hu et al., "Hepadnavirus assembly and reverse transcription require a multi-component chaperone complex which is incorporated into nucleocapsids," *EMBO J*, 16:59-68, 1997.

Hu et al., "β-Thujaplicinol inhibits hepatitis B virus replication by blocking the viral ribonuclease H activity," *Antiviral Research*, 99:221-229, 2013.

Ilina et al., "Inhibitors of HIV-1 reverse transcriptase-associated ribonuclease H activity," *Biology (Basel)*, 1(3):521-541, 2013.

Ireland et al., "Synthetic α-hydroxytropolones inhibit replication of wild-type and acyclovir-resistant herpes simplex viruses," *Antimicrob. Agents Chemother.*, pp. 1-35, 2016.

Keck and Marqusee, "Substitution of a highly basic helix/loop sequence into the RNase H domain of human immunodeficiency virus reverse transcriptase restores its $Mn^{2+}$-dependent RNase H activity," *Proc. Natl. Acad. Sci. USA*, 92(7):2740-2744, 1995.

Klarmann et al., "Uncovering the complexities of retroviral ribonuclease H reveals its potential as a therapeutic target," *AIDS Rev*, 4:183-194, 2002.

Lanford et al., "Nucleotide priming and reverse transcriptase activity of hepatitis B virus polymerase expressed in insect cells," *J Virol*, 69:4431-4439, 1995.

Lee et al., "RNase H activity of human hepatitis B virus polymerase expressed in *Escherichia coli*," *Biochem Biophys Res Commun*, 233:401-407, 1997.

Lin et al., "Functional and structural dynamics of hepadnavirus reverse transcriptase during protein-primed initiation of reverse transcription: effects of metal ions," *J Virol*, 82:5703-5714, 2008.

Lu et al., "Hydroxylated tropolones inhibit hepatitis B virus replication by blocking viral ribonuclease H activity," *Antimicrobial Agents and Chemotherapy*, 59(2):1070-1079, 2015.

Office Action issued in U.S. Appl. No. 14/647,331, dated Jun. 16, 2016.

Office Action issued in U.S. Appl. No. 14/647,331, dated Jan. 12, 2017.

Office Action issued in U.S. Appl. No. 14/647,331, dated May 9, 2017.

PCT International Preliminary Report on Patentability issued in International Application No. PCT/US2013/072201, dated Jun. 11, 2015.

PCT International Search Report and Written Opinion issued in International Application No. PCT/US2013/072201, dated May 29, 2014.

Pelletier et al., "A structural basis for metal ion mutagenicity and nucleotide selectivity in human DNA polymerase beta," *Biochemistry*, 35:12762-12777, 1996.

Potenza et al., "Optimized expression from a synthetic gene of an untagged RNase H domain of human hepatitis B virus polymerase which is enzymatically active," *Protein Expr Purif*, 55:93-99, 2007.

Radziwill et al., "Mutational analysis of the hepatitis B virus P gene product: domain structure and RNase H activity," *J Virol*, 64:613-620, 1990.

Shaw-Reid, et al., "Inhibition of HIV-1 ribonuclease H by a novel diketo acid, 4-[5-(benzoylamino)thien-2-yl]-2,4-dioxobutanoic acid," *J Biol Chem*, 278:2777-2780, 2003.

Stürmer et al., "Human immunodeficiency virus: 25 years of diagnostic and therapeutic strategies and their impact on hepatitis B and C virus," *Med. Microbiol. Immunol.*, 198(3):147-155, 2009.

Suchaud et al., "Development of a series of 3-hydroxyquinolin-2(1H)-ones as selective inhibitors of HIV-1 reverse transcriptase associated RNase H activity," *Bioorganic & Medicinal Chemistry Letters*, 22:3988-3992, 2012.

Suchaud et al., "Investigation of a novel series of 2-hydroxyisoquinoline-1,2(2H,4H)-diones as human immunodeficiency virus type 1 integrase inhibitors," *Journal of Medicinal Chemistry*, 57:4640-4660, 2014.

Tavis and Ganem, "Expression of functional hepatitis B virus polymerase in yeast reveals it to be the sole viral protein required for correct initiation of reverse transcription," *Proc Natl Acad Sci USA*, 90:4107-4111, 1993.

Tavis and Lomonosova, "The hepatitis B virus ribonuclease H as a drug target," *Antiviral Research*, 118:132-138, 2015.

Tavis et al., "Inhibitors of nucleotidyl transferase superfamily enzymes suppress herpes simplex virus replication," *Antimicrob Agents Chemother*, 58(12):7451-7461, 2014.

Tavis et al., "The hepatitis B virus ribonuclease H is sensitive to inhibitors of the human immunodeficiency virus ribonuclease H and integrase enzymes," *PLoS Pathog.*, 9(1):e1003125, 2013.

Vartanian et al., "Hypermutagenic PCR involving all four transitions and a sizeable proportion of transversions," *Nucleic Acids Res*, 24:2627-2631, 1996.

Vernekar et al., "Design, synthesis, biochemical, and antiviral evaluations of C6 benzyl and C6 biarylmethyl substituted 2-hydroxylisopquinoline-1,3-diones: dual inhibition against HIV reverse transcriptase-associated RNase H and polymerase with antiviral activities," *Journal of Medicinal Chemistry, J. Med. Chem.*, 58:651-664, 2015.

Vianna et al., "Screening of CHO cell clones expressing histidine-tagged major S hepatitis B surface protein using a semi-quantitative PCR protocol," *Journal of Virological Methods*, 114(2):171-174, 2003.

Wei and Peterson, "Expression, purification, and characterization of an active RNase H domain of the hepatitis B viral polymerase," *J Biol Chem*, 271:32617-32622, 1996.

Wei et al., "Relationship between viral DNA synthesis and virion envelopment in hepatitis B viruses," *J Virol*, 70:6455-6458, 1996.

Williams et al., "Potent and selective HIV-1 ribonuclease H inhibitors based on a 1-hydroxy-1,8-naphthyridin-2(1H)-one scaffold," *Bioorg Med Chem Lett*, 20:6754-6757, 2010.

Hydroxylated Tropolone Derivatives
46. Beta Thujaplicinol 
47. Beta Thujaplicin 
48. Gamma thujaplicin 
49. Nootkatin 
50. 5-nitrosotropolone 
51. Tropolone p-nitrobenzoate 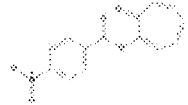
52. NSC 79555 
53. Tropolone 
54. Tropolone p-nitrobenzoate 
55. NSC 282885 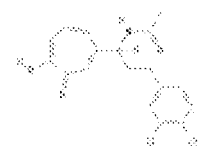
56. Manicol 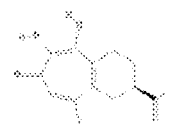
57. 2-Chlorotropolone 
59. Chembridge 5945310 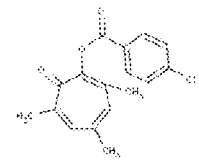
60. Chembridge 5942159 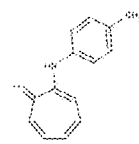
61. Chembridge 5940946 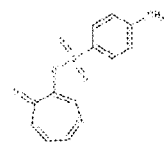
62. Chembridge 5946384 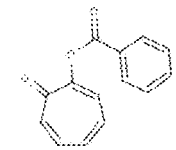
63. Chembridge 5938894 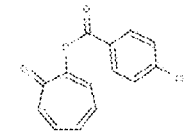
FIG. 12

Ciclopirox Derivatives
1. FCHC 2456 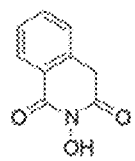
41. Ciclopirox 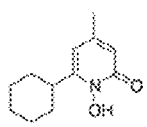
42. Labotest 72543251 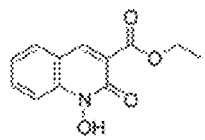
43. Sigma PH008969 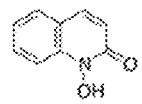
44. Labotest 12243782 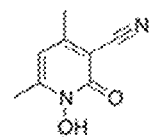
45. TCI America H1040 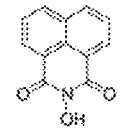
Hydroxyxanthenone Derivatives
8. Sigma S439274 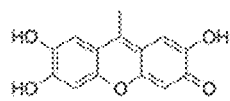
30. Chembridge 7248520 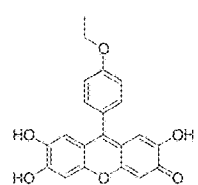
31. Chembridge 5104346 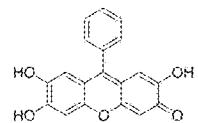
34. Idofine D-009 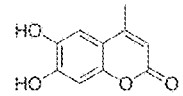
35. TCI America D1118 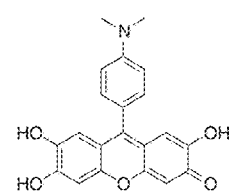
39. Asinex BAS0223612 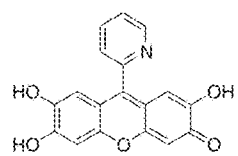
FIG. 12 (cont.)

Aminocyanothiophenes Derivatives
6. Chembridge 7929959 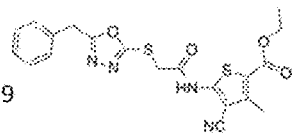
28. Chembridge 7570508 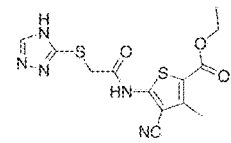
24. Chembridge 7933420 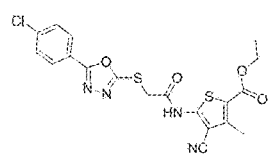
29. Chembridge 7943262 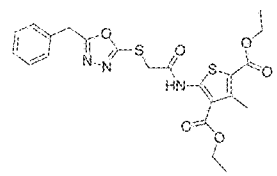
25. Chembridge 7878467 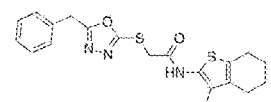
32. Enamine T6060486 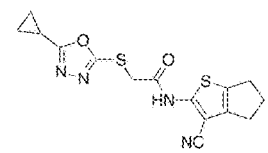
26. Chembridge 7962359 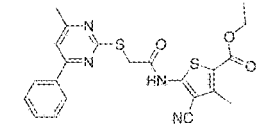
37. Vistas M Lab STK082278 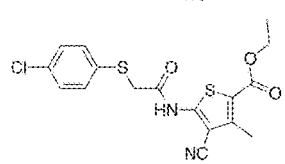
27. Chembridge 7698174 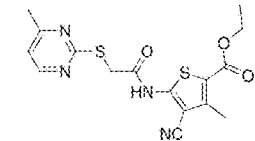
Cyanopyran Derivatives
5. Enamine T0506-3483 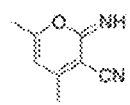
21. Sigma S647632 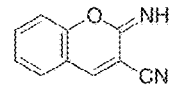
19. Sigma 586862 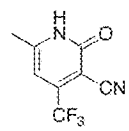
33. Idofine 17-083 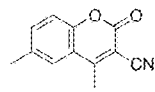
20. Sigma L133671 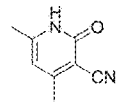
FIG. 12 (cont.)

Miscellaneous Compounds
2. Sigma 74540 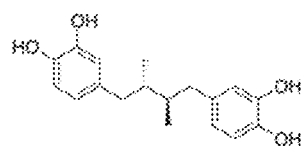
3. Sigma n8164 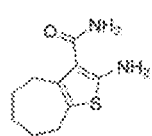
4. TimTec ST029023 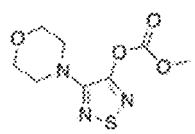
7. Idofine 021030 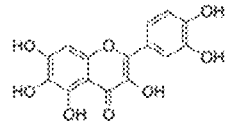
9. Sigma 70050 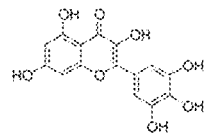
12. Napthyridinone 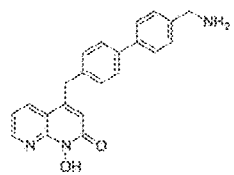
13. KHMP05 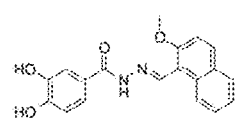
14. KHMP02 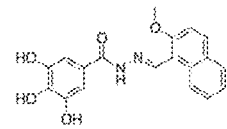
15. BHMP07 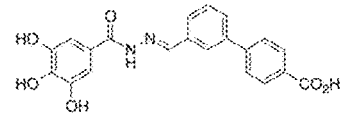
22. CAS 40106-12-5 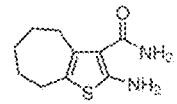
38. Visas M Lab STK317995 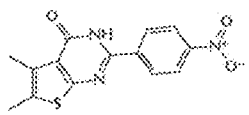
FIG. 12 (cont.)

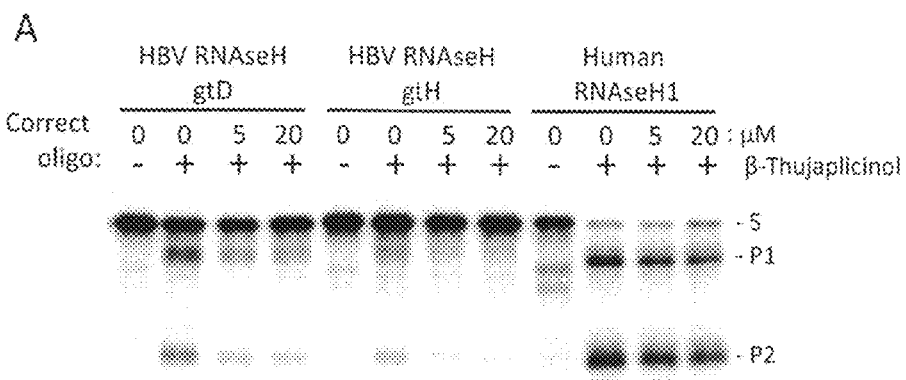
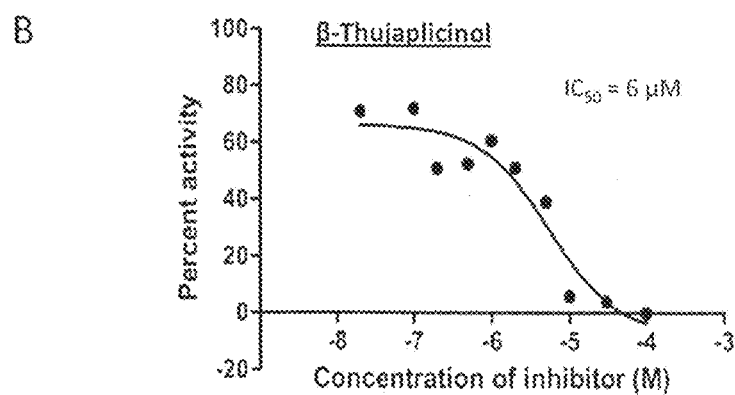
FIG. 13A-B

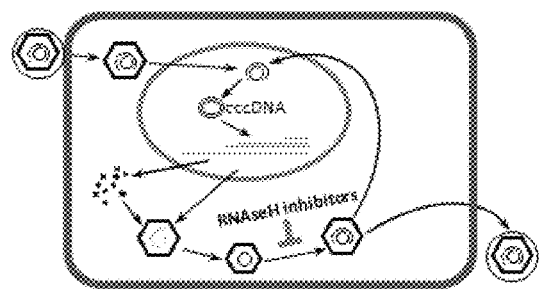
FIG. 20
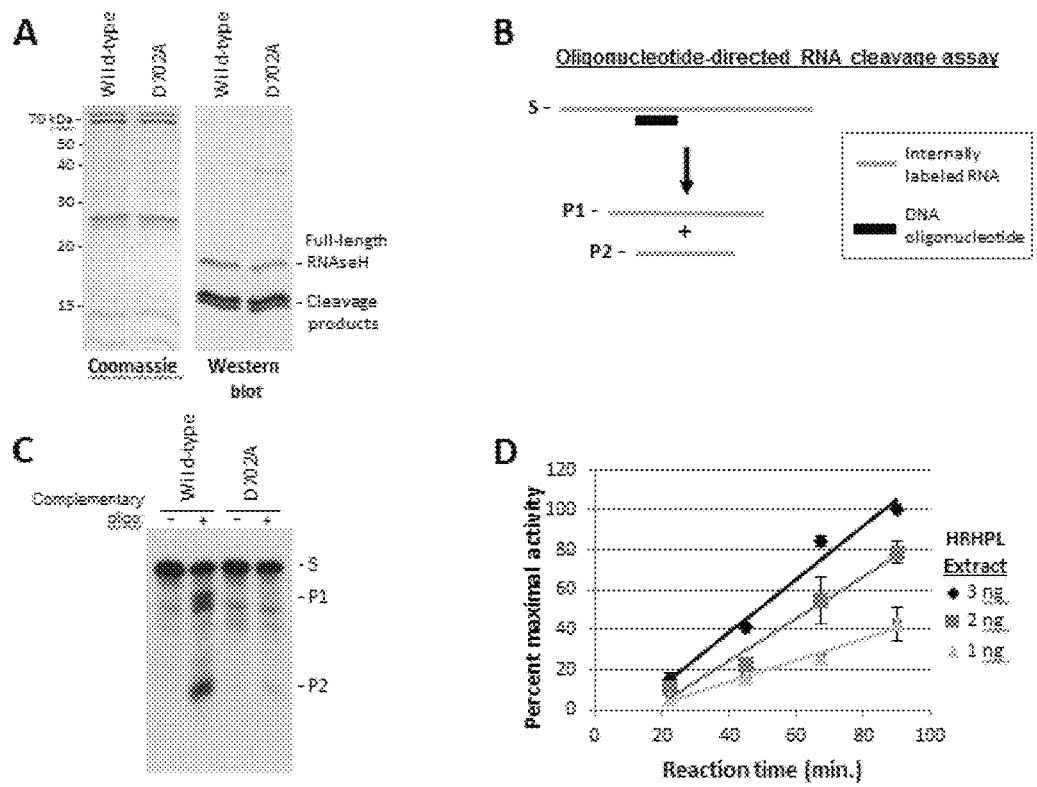
FIGS. 21A-D

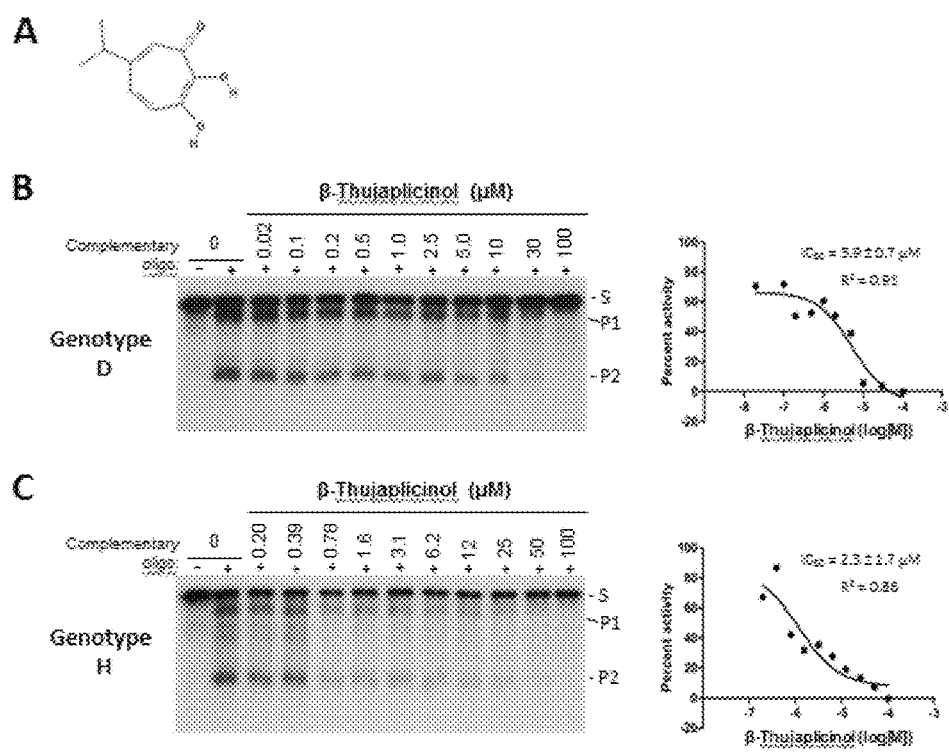
FIGS. 22A-C

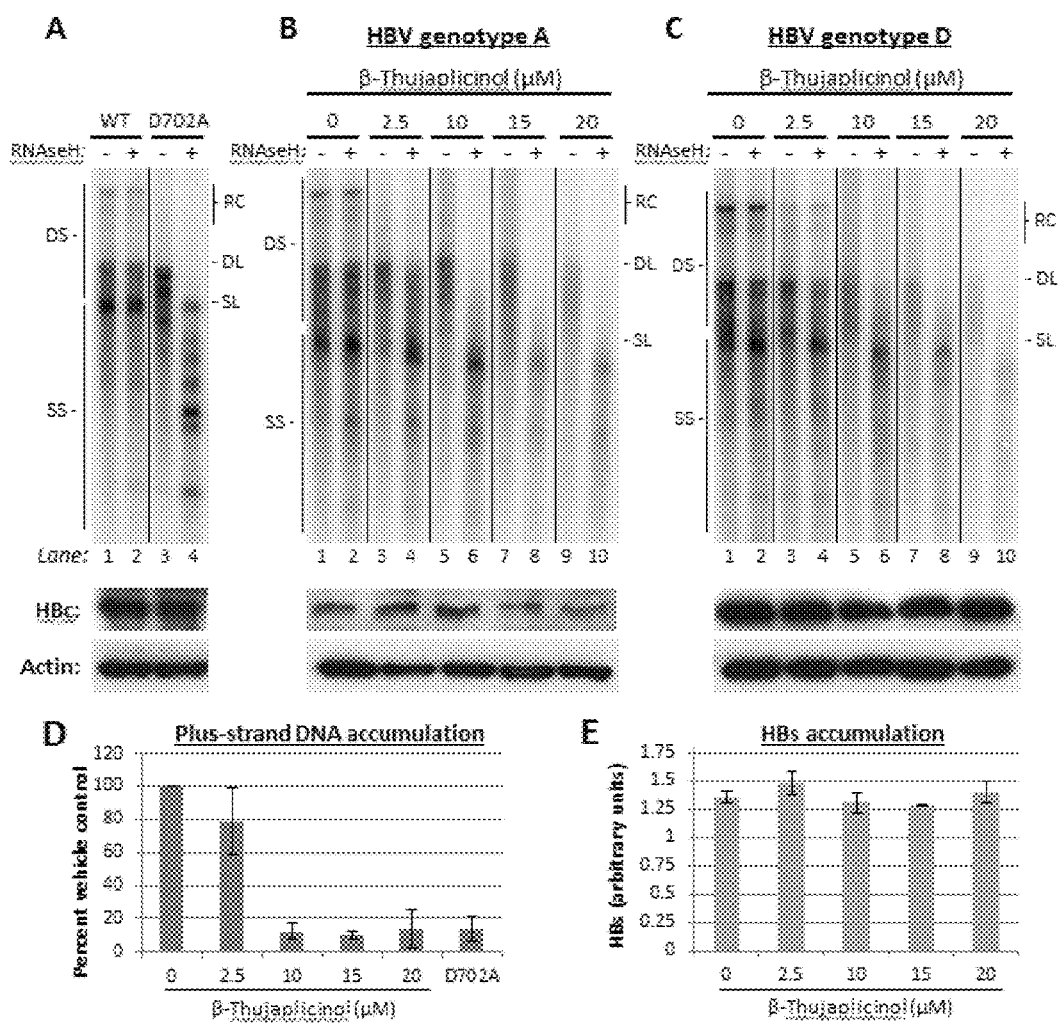
FIGS. 24A-E

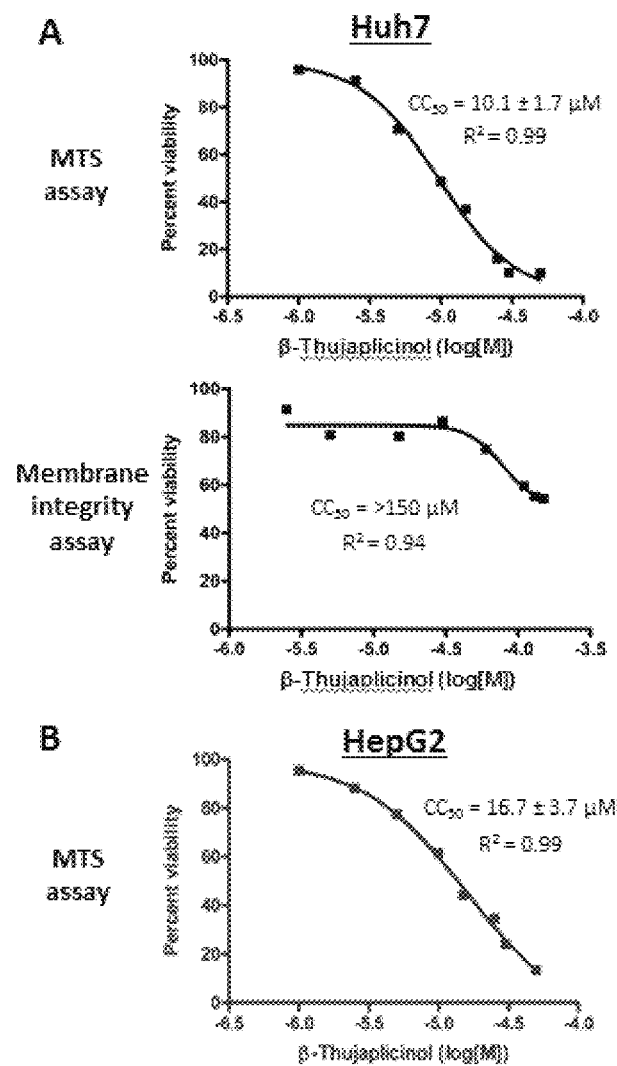
FIGS. 25A-B

HBV RNASE H PURIFICATION AND ENZYME INHIBITORS

The present application is a divisional of U.S. application Ser. No. 14/647,331, filed May 26, 2015, which is a national phase application under 35 U.S.C. § 371 of International Application No. PCT/US2013/072201, filed Nov. 27, 2013, which claims benefit of priority to U.S. Application Ser. No. 61/730,344, filed Nov. 27, 2012 and Ser. No. 61/821,623, filed May 9, 2013, the entire contents of each of the above-referenced applications being hereby incorporated by reference.

BACKGROUND OF THE INVENTION

I. Field of the Invention

The invention relates to the fields of pathology, virology, molecular biology and pharmaceuticals. More specifically, the invention relates to the purification of active forms of hepatitis B virus RNAase H and its use to identify candidate inhibitors for the treatment and prevention of HBV disease. Also provided are compounds having such activity.

II. Related Art

Hepatitis B virus (HBV) is a hepatotropic DNA virus that replicates by reverse transcription (Hostomsky et al., 1993). It chronically infects >350 million people world-wide and kills up to 1.2 million patients annually by inducing liver failure and liver cancer (Steitz, 1995; Katayanagi et al., 1990; Yang et al., 1990; Lai et al., 2000). Reverse transcription is catalyzed by a virally-encoded polymerase that has two enzymatic activities: a DNA polymerase that synthesizes new DNA and a ribonuclease H (RNAseH) that destroys the viral RNA after it has been copied into DNA (Hostomsky et al., 1993; Rice et al., 2001; Hickman et al., 1994; Ariyoshi et al., 1994). Both activities are essential for viral replication.

HBV infections are treated with interferon α or one of five nucleos(t)ide analogs (Parker et al., 2004; Song et al., 2004; Lima et al., 2001). Interferon α leads to sustained clinical improvement in 20-30% of patients, but the infection is very rarely cleared (Hostomsky et al., 1993; Katayanagi et al., 1990; Braunshofer-Reiter et al., 1998). The nucleos(t)ide analogs are used more frequently than interferon. They inhibit DNA synthesis and suppress viral replication by 4-5 $\log_{10}$ in up to 70-90% patients, often to below the standard clinical detection limit of 300-400 copies/ml (Braunshofer-Reiter et al., 1998; Nowotny et al., 2005; Klumpp et al., 2003. However, treatment eradicates the infection as measured by loss of the viral surface antigen (HBsAg) from the serum in only 3-6% of patients even after years of therapy (Braunshofer-Reiter et al., 1998; Nowotny et al., 2005; Klumpp et al., 2003; Nowotny et al., 2006). Antiviral resistance was a major problem with the earlier nucleos(t)ide analogs, but resistance to the newer drugs entecavir and tenofovir is very low (Parker et al., 2004; Keck et al., 1998; Goedken et al., 2001; Li et al., 1995). This has converted HBV from a steadily worsening disease into a controllable condition for most individuals (McClure, 1993). The cost of this control is indefinite administration of the drugs (probably life-long; (Song et al., 2004), with ongoing expenses of $400-600/month (Poch et al., 1989; Hu et al. 1996; Hu et al., 1997) and unpredictable adverse effects associated with decades-long exposure to the drugs.

The key form of the HBV genome in cells that must be eliminated to clear the infection is the nuclear episomal covalently-closed circular DNA (cccDNA) that is the template for transcription of all HBV RNAs (Gong et al. 2001 and Radziwill et al., 1988). Following reverse transcription in the cytoplasm, newly synthesized genomes can either be enveloped and secreted from the cell as virions, or they can be transported into the nucleus to replenish the cccDNA pool (FIG. 1) (Gong et al. 2001; Radziwill et al., 1988; Gerelsaikhan et al., 1996). Transfer of newly synthesized viral genomes into the nucleus via "recycling" is the default pathway, and virion secretion occurs only if the cccDNA pool is large enough to support adequate synthesis of the HBsAgs.

The cccDNA pool is very stable, but nucleos(t)ide therapy can suppress cccDNA levels in the liver by ~1 $\log_{10}$ after 1-2 years (Wei et al., 1996; Chen et al., 1994; Chang et al., 1994). The indefinite persistence of the cccDNA even in patients whose HBV titres in serum have been suppressed below the limit of clinical detection by the nucleos(t)ide analogs is due to residual viral replication, leading to replenishment of the cccDNA pool by a combination of intracellular recycling and low-level infection of new cells (Radziwill et al., 1988 and Radziwill, et al., 1990). The sequential accumulation of resistance mutations during nucleos(t)ide therapy confirms that cccDNA maintenance by residual viral replication occurs in the absence of clinically detectable viremia (Goedken et al., 2001; Li et al., 1995; Chang et al., 1990). A recent genetic analysis of HBV DNA in the liver explicitly demonstrated that low levels of cccDNA replenishment occurs even when nucleos(t)ide analog therapy has reduced viral titres below the clinical detection limit (Radziwill, et al., 1990).

RNAseH enzymes hydrolyze RNA in an RNA:DNA heteroduplex (Hostomsky et al., 1993). They belong to the nucleotidyl transferase superfamily whose members share a similar protein fold and presumably have similar enzymatic mechanisms (Yang and Steitz, 1995). This family includes E. coli RNAseH I and II (Katayanagi, et al., 1990, Yang et al., 1990, Lai et al., 2000), DNA transposases including the Tn5 transposase (Rice and Baker, 2001), retroviral integrases including the HIV integrase (Dyda, et al., 1994), the RuvC Holliday junction resolvase (Ariyoshi, et al., 1994), the Argonaute RNAse (Parker, et al., 2004; Song, et al., Science 305: 1434-1437, 2004), and human RNAseH 1 and 2 (Lima et al., 2001; Frank et al., 1998, Frank, et al., 1998). The canonical RNAseH structure contains about 100 aa including four conserved carboxylates (the "DEDD" motif) that coordinate two divalent cations (Nowotny et al., 2005). The RNAseH mechanism is believed to involve both divalent cations (Yang and Steitz, 1995, Klumpp, et al., 2003, Nowotny and Yang, 2006), although a one-ion mechanism has also been proposed (Keck et al., 1998 and Goedken and Marqusee, 2001). The HBV RNAseH domain shares low but recognizable (~20%) sequence identity with the RNAseH domains of reverse transcriptases and other retro-elements (Li et al., 1995, McClure, 1993, Poch et al., 1998). Manually optimizing alignment of the HBV RNAseH and the HIV-1 RNAseH yielded 23% identity and 33% similarity (FIG. 2). A similar alignment between the HBV RNAseH and the HIV integrase revealed 19% identity and 33% similarity.

The HBV RNAseH is encoded at the carboxy-terminus of the viral polymerase protein that also encodes the viral DNA polymerase activity (reverse transcriptase). The high hydrophobicity of the HBV polymerase and its existence as a complex with host chaperones (Hu and Seeger, 1996 and Hu et al., 1997) have severely restricted study of the HBV RNAseH. Furthermore, the inventor demonstrated that the RNAseH in its native context within the polymerase protein is unable to accept exogenous heteroduplex substrates (Gong et al., 2001), analogous to the inability of the DNA polymerase active site to engage exogenous primer-templates (Radziwill et al., 1988). Consequently, most of the limited knowledge of the RNAseH comes from mutational studies of the viral genome in the context of viral replication conducted by us and others (Chang et al., 1990, Radziwill et al., 1990, Gerelsaikhan et al., 1996, Wei et al., 1996, Chen et al., 1994 and Chang et al., 1994). These restrictions have prevented biochemical characterization of the RNAseH and blocked biochemical screens for anti-HBV RNAseH drugs to date.

A few reports of recombinant forms of the hepadnaviral RNAseH exist. Wei and co-workers (Wei et al., 1996) expressed the HBV RNAseH domain in *E. coli* and purified it by denaturing nickel-affinity chromatography. Following refolding, they found an RNAse activity. (Lee et al., 1997) expressed the HBV RNAseH domain in *E. coli* as a dual maltose-binding protein/hexahistidine fusion and purified soluble protein by two-step affinity chromatography; this enzyme had RNAseH activity. Choi and co-workers (Choi et al., 2002) expressed the intact duck hepatitis B virus polymerase in yeast and reported that it had a weak RNAse activity. Finally, Potenza et al. (Potenza et al., 2007) expressed the HBV RNAseH domain as a synthetic gene in *E. coli*. Following purification from inclusion bodies and refolding, this enzyme had RNAse activity. However, only the (Lee et al., 1997) publication included controls sufficient to demonstrate that the observed RNAse activity was actually an RNAseH and not another type of RNAseH or contamination with cellular RNAseH enzymes. Furthermore, no follow-up reports have appeared with any of these systems, possibly due to the technical difficulties associated with the purification protocols and/or contamination challenges with host RNAseH or other RNAse classes.

Human Immunodeficiency Virus (HIV) reverse transcription also requires a virally encoded RNAseH activity (Freed and Martin, 2007), and consequently the RNAseH has attracted much attention as a potential drug target (Klumpp, et al., 2003; Klarmann et al., 2002; Klumpp and Mirzadegan, 2006; Takada, et al., 2007; Bokesch, et al., 2008; Wendeler et al., 2008; Fuji et al., 2009; Su et al., 2010; Di, et al., 2010; Chung, et al., 2010; Williams, et al., 2010; Chung, et al., 2011; Billamboz et al., 2011; Didierjean et al., 2005; Budihas, et al., 2005; Himmel et al., 2009; Shaw-Reid, et al., 2003; Himmel, et al., 2006; Kirschberg et al., 2009; Suchaud et al., 2012 and Gong et al., 2011). Over 100 anti-HIV RNAseH compounds have been reported, typically with inhibitory concentration-50% ($IC_{50}$) values in the low µM range. Most of the compounds inhibit HIV replication in culture, typically with effective concentration-50% ($EC_{50}$) values that are ~10-fold higher than the biochemical $IC_{50}$ values. These compounds are often modestly cytotoxic, leading to therapeutic indices (TI) that are usually <10. Second-generation inhibitors with substantially improved efficacy have been reported, but their TI values were not necessarily improved markedly (Williams, et al., 2010; Chung, et al., 2011; Billamboz et al., 2011). Despite these limitations, compounds with efficacy and TI values appropriate for a drug exist (Williams, et al., 2010 and Himmel, et al., 2006). Most of the compounds inhibit the RNAseH by binding to the enzyme and chelating the divalent cations in the active site (Fuji et al., 2009; Su et al., 2010; Chung, et al., 2011; Billamboz et al., 2011; Himmel et al., 2009 and Kirschberg et al., 2009), but compounds that appear to inhibit the RNAseH by altering the enzyme's conformation or its interaction with nucleic acids have also been reported (Wendeler et al., 2008 and Himmel, et al., 2006). As predicted from their common membership in the nucleotidyl transferase superfamily, some anti-HIV RNAseH compounds can inhibit the HIV integrase, and some anti-integrase compounds can inhibit the RNAseH (Klarmann et al., 2002; Williams, et al., 2010; Billamboz et al., 2011; Shaw-Reid, et al., 2003 and Billamboz, et al., 2008).

The ability of the nucleos(t)ide analog drugs to profoundly suppress HBV in most patients and to cure HBV infection in a few patients indicates that they can push the virus to the brink of elimination. This presents an opportunity to cure many more patients by suppressing HBV replication further, but achieving a cure will require novel drugs against targets other than the DNA polymerase active site. These drugs, when identified, could be used in combination with the nucleos(t)ide analogs to suppress viral replication below the level needed to maintain the cccDNA.

SUMMARY OF THE INVENTION

Provided herein is a method isolating a hepatitis B virus (HBV) RNAseH comprising (a) providing a cell that expresses said HBV RNAseH; (b) lysing said cell by sonication to produce a lysate; (c) applying said lysate to a nickel-agarose affinity chromatography column; (d) eluting bound material from said column with imidazole; and (e) removing imidazole from the eluate. The cell may be a cell infected with HBV. The cell may comprise an HBV RNAseH expression vector. The cell may be a prokaryotic cell, such as an *Eschericia coli* cell, or may be a eukaryotic cell. The imidazole may be applied to said column at 100 mM to 500 mM. The removing imidazole step may comprise dialyzing the eluate into a buffered salt solution, such as a salt solution containing, or has added thereto, glycerol and/or dithiothreitol. The RNAseH mat be produced in an in vitro translation system. The lysing step may comprise sonication, lysozyme/detergent treatment, shearing or nitrogen rupture.

In another embodiment, there is provided an isolated and active hepatitis B virus (HBV) RNAseH obtained by the process comprising (a) providing a cell that expresses said HBV RNAseH; (b) lysing said cell to produce a lysate; (c) applying said lysate to a nickel-agarose affinity chromatography column; (d) eluting bound material from said column with imidazole; and (e) removing imidazole from the eluate. The cell may be infected with HBV. The cell may be a cell comprising an HBV RNAseH expression vector. The imidazole may be applied to said column at 100 mM to 500 mM. The step of removing imidazole may comprise dialyzing the eluate into a buffered salt solution.

In still yet another embodiment, there is provided a purified or isolated hepatitis B virus (HBV) RNAseH composition retaining RNAseH activity and being substantially devoid of other enzyme activity, and wherein said composition has (a) RNAseH activity in the presence 2-8 mM $Mg^{2+}$ and (b) no specific activity for RNA:DNA heteroduplexes below 90 mM NaCl. The RNAseH may be a genotype H RNAseH.

In a further embodiment, there is provided a method of screening a substance for hepatitis B virus (HBV) RNAseH inhibitory activity comprising (a) providing a purified or isolated hepatitis B virus (HBV) RNAseH composition retaining RNAseH activity and being substantially devoid of other enzyme activity; (b) contacting said HBV RNAseH composition with a candidate substance; and (c) assessing the activity of said HBV RNAseH composition in step (b), wherein a reduced level of activity of said HBV RNAseH composition in step (b), as compared to activity of said HBV RNAseH composition in the absence of said candidate substance, identifies said candidate substance as an inhibitor of said HBV RNAseH. Assessing may comprise a DNA oligonucleotide-directed RNA cleavage assay, may comprise gel electrophoresis, such as SDS-PAGE or urea-PAGE, and may comprise measuring fluorescent quenching from a dual-labeled substrate, may comprise measuring soluble radioactivity following annealing of radiolabeled RNA to DNA, or may comprise measuring soluble fluorescence following annealing of radiolabeled RNA to DNA. The DNA may be immobilized on a surface. The method may further comprise assessing activity of said HBV RNAseH composition in the absence of said candidate substance. The step of providing may comprises (a) providing a cell that expresses said HBV RNAseH; (b) lysing said cell to produce a lysate; (c) applying said lysate to a nickel-agarose affinity chromatography column; (d) eluting bound material from said column with imidazole; and (e) removing imidazole from the eluate. The RNAseH may present at between about 0.5 and 100 ng/µl, or 0.15 and 0.75 ng/µl.

The HBV RNAse H composition may be a buffered aqueous solution having a NaCl concentration of in the range of about 120 mM to about 240 mM, or having a NaCl concentration in the range of about 170 mM to about 210 mM. The HBV RNAse H composition may comprise $Mg^{+2}$ ions or $Mn^{+2}$ ions. The HBV RNAse H composition may comprise between about 0.05% to about 1% of a nonionic surfactant, by volume.

In still a further embodiment, there is provided a method of inhibiting a hepatitis B virus (HBV) RNAseH comprising contacting said enzyme with a compound having the formula:

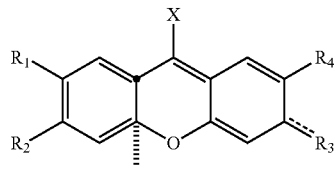

FORMULA I wherein:
$R_1$ is —OH; $R_2$ is —OH; $R_3$ is —OH or O; $R_4$ is —OH; and X is H, methyl, substituted or unsubstituted phenyl or piperidine; or

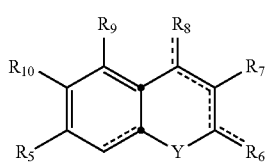

FORMULA II wherein:
$R_5$ is H, —OH or $C_1C_6$ alkoxy; $R_6$ is H, O or substituted or unsubstituted phenyl; $R_7$ is H, —OH or —COOH; $R_8$ is —CH$_3$ or O; $R_9$ is —OH or H; $R_{10}$ is H, —OH, $C_1$-$C_4$ alkyl optionally substituted with substituted or unsubstituted phenyl; Y is O or $NR_{11}$, wherein $R_{11}$ is branched or straight-chain $C_1$-$C_6$ alkyl or hydroxyalkyl or

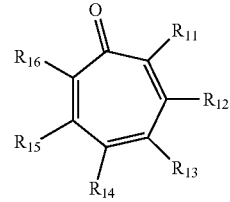

FORMULA III wherein: $R_{11}$ is hydrogen, —$OR_{17}$, hydroxy, or halo, wherein $R_{17}$ is $C_1$-$C_8$ acyl, $C_1$-$C_8$ alkyl, or a substituted version of either of these groups; $R_{12}$ is hydrogen, hydroxy or halo; $R_{13}$ and $R_{14}$ are each independently hydrogen, hydroxy, nitroso, $C_1$-$C_{12}$ alkyl, $C_1$-$C_{12}$ alkenyl, $C_1$-$C_{12}$ alkynyl, $C_1$-$C_{12}$ aryl, $C_1$-$C_{12}$ aralkyl, $C_1$-$C_{12}$ amido, a substituted version of any of these groups, or $R_{13}$ is taken together with $R_{14}$ as provided below; $R_{15}$ is hydrogen, $C_1$-$C_{12}$ alkyl, $C_1$-$C_{12}$ alkenyl, $C_1$-$C_{12}$ alkynyl, $C_1$-$C_{12}$ aryl, $C_1$-$C_{12}$ aralkyl,

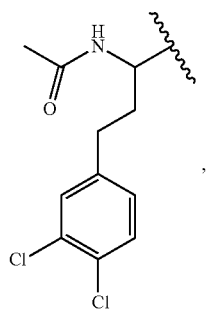

or a substituted version of any of these groups; and $R_{16}$ is hydrogen, unsubstituted $C_1$-$C_6$ alkyl, substituted $C_1$-$C_6$ alkyl, or hydroxyl; provided that when $R_{13}$ and $R_{14}$ are taken together as further defined by FORMULA IV:

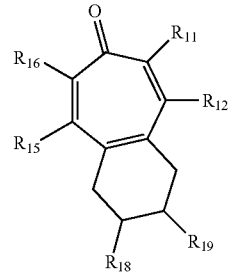

FORMULA IV $R_{18}$ and $R_{19}$ are each independently hydrogen, $C_1$-$C_6$ alkyl, $C_1$-$C_6$ alkenyl, $C_1$-$C_6$ alkynyl.

The compound may be of FORMULA I and X may be phenyl substituted with O or $NR_{12}R_{13}$ at the para position, wherein $R_{12}$ and $R_{13}$ are H or —CH$_3$. The compound may be of FORMULA II and $R_6$ may be di- or tri-substituted phenyl. The compound may be of FORMULA II and $R_{10}$ may be CH$_2R_{14}$, wherein $R_{14}$ is halogen-disubstituted phenyl. The compound may be of FORMULA III and $R_{11}$ is hydroxy. The compound may be of FORMULA III and at least one of $R_{12}$, $R_{13}$, $R_{14}$ or $R_{15}$ is $C_1$-$C_{12}$-alkyl. The compound may be of FORMULA IV and $R_{18}$ is $C_1$-$C_6$ alkenyl.

The method may further comprise contacting said enzyme with a second inhibitor of RNAse enzyme activity. The second inhibitor may be a nucleoside analog. The method may further comprise contacting said enzyme with said compound a second time. The enzyme may be located in a cell or may be located in vitro. The cell may be located in a living subject, such as a mammal, including a mammal infected with HBV. The compound may be administered intravenously, intra-arterially, orally, or subcutaneously. The subject may be further administered a second inhibitor of RNAse enzyme activity, such as a nucleoside analog. The second inhibitor may be administered to said subject before or after said compound, or at the same time as said compound. The subject may have previously received a first-line HBV therapy, and further may have HBV that has developed resistance to said first-line HBV therapy. The subject may be administered interferon or pegylated interferon.

In an additional embodiment, there is provided a method of inhibiting a hepatitis B virus (HBV) RNAseH comprising contacting said enzyme with a compound having the formula selected from the group consisting of:

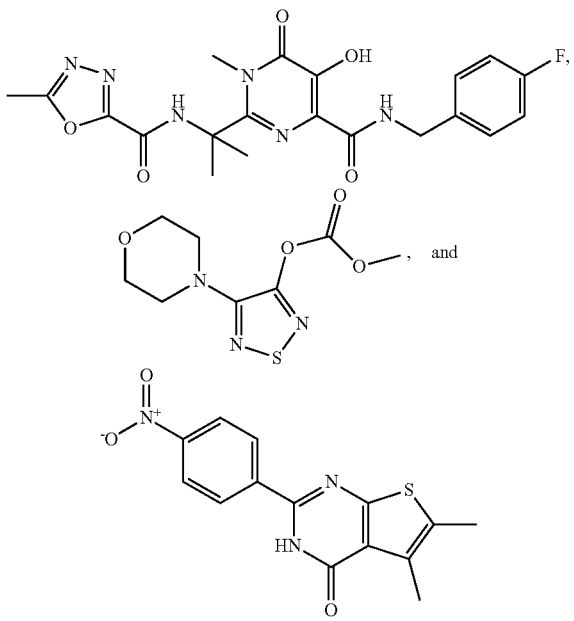

The method may further comprise contacting said enzyme with a second inhibitor of RNAse enzyme activity. The second inhibitor may be a nucleoside analog. The method may further comprise contacting said enzyme with said compound a second time. The enzyme may be located in a cell or may be located in vitro. The cell may be located in a living subject, such as a mammal, including a mammal infected with HBV. The compound may be administered intravenously, intra-arterially, orally, or subcutaneously. The subject may be further administered a second inhibitor of RNAse enzyme activity, such as a nucleoside analog. The second inhibitor may be administered to said subject before or after said compound, or at the same time as said compound. The subject may have previously received a first-line HBV therapy, and further may have HBV that has developed resistance to said first-line HBV therapy. The subject may be administered interferon or pegylated interferon.

In still a further embodiment, there is provided a composition comprising purified hepatitis B virus RNAse H in a storage medium that retains at least 50% of initial RNAse H activity for at least 5 hours at 0° C. The composition may be at a temperature below minus 50° C. The storage medium may maintain reducing conditions, such as with dithiothreitol (DTT). The storage medium may be buffered to a pH in the range of about pH 6.6 to about pH 8.5, or to a pH in the range of about pH 7.2 to about pH 7.8. The composition may further comprise NaCl at a concentration in the range of of about 300 mM to about 1M. The composition may be stored in liquid nitrogen, such as in at least 5 containers each having a volume of less than 1 ml. The composition may have RNAse H present at about 0.1 to 1.0 ng/μl, at about 0.1 to 0.5 ng/μl or at about 0.5 ng/μl. The RNAse H may be present at about 0.01 to 0.05% of total protein, or at about 0.02 to 0.025% of total protein.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 2A-B. Alignments between the HBV RNAseH and the HIV-1 RNAseH and integrase. Manually optimized alignments between HBV RNAseH (SEQ ID NO: 17) and the HIV-1 RNAseH (SEQ ID NO:18) (FIG. 2A) or integrase (SEQ ID NO:19) (FIG. 2B). The HBV genotype D sequence is from Genbank entry V01460 and the HIV-1 sequences are from strain HBX2; Genbank K03455.1. Identical residues are shaded in black and similar residues are shaded in gray. The numbering for each sequence is indicated at top. * indicates the conserved nucleotidyl transferase superfamily active site carboxylates (D-E-D-D for the RNAseH enzymes and D-D-E for the integrase).

(FIG. 4A) Structure of the recombinant RNAseHs. The HBV polymerase with its major domains labeled is at top. The recombinant RNAseH derivatives are shown below with the C-terminal hexahistidine tag in brown. TP, terminal protein domain; RT, reverse transcriptase domain; *, mutations D702A or E731A to RNAseH active site residues. (FIG. 4B) Proteins in the enriched lysates. The left panel is a Coomassie-blue stained SDS-PAGE gel of enriched RNAseH extracts as employed in the RNAseH assays. The right panel is a western blot of the extracts employing monoclonal antibody 9F9 which recognizes an epitope near the C-terminus of the HBV polymerase.

(FIG. 5A) Oligonucleotide-directed RNAseH assay. Uniformly $^{32}$P-labeled RNA (blue or red) is annealed to a complementary DNA oligonucleotides (black). RNAseH activity cleaves the RNA in the heteroduplex formed where the oligonucleotide anneals to the RNA and yields two products (P1 and P2). (FIG. 5B) Recombinant HBV RNAseH is active. An oligonucleotide-directed RNAseH assay was conducted with E. coli RNAseH, wild-type HBV RNAseH (HRHPL), or RNAseH-deficient HRHPL (D702A). A complementary oligonucleotide (+) or non-complementary oligonucleotide (−) was mixed with labeled DRF+ RNA and the reactions were incubated to allow RNAseH activity. The products were resolved by SDS-PAGE and the RNAs were detected by autoradiography. Oligonucleotide set 1 was D2507− and D2526+ and oligonucleotide set #2 was D2543M-Sal and D2453+. The positions of the cleavage products (P1 and P2) are indicated in blue for reactions containing oligonucleotide D2507− and in red for reactions containing oligonucleotide D2543M-Sal. (FIG. 5C) FRET-based RNAseH assay. A self-complementary chimeric RNA:DNA synthetic oligonucleotide (RHF1) forms a stem-loop in which the stem is an RNA:DNA heteroduplex. The stem brings the fluorescein (F) and quencher (Q) at the 5' and 3' ends of the oligonucleotide into close proximity. Cleavage of the RNA releases the fluorescein and increases its fluorescence. (FIG. 5D) Detection of HBV RNAseH activity employing the fluorescent assay. The substrate in FIG. 5C was employed in an RNAseH assay employing buffer alone, wild-type HBV RNAseH (HRHPL), or RNAseH-deficient HRHPL (D702A/E731A). *, P<0.05.

(FIG. 6A) Sequence alignment for genotype A (SEQ ID NO:1), B (SEQ ID NO:2), C (SEQ ID NO:3), D (SEQ ID NO:4), and H (SEQ ID NO:5) versions of the HBV RNAseH expression construct HRHPL. The additional methionine at residue 10 of the genotype D sequence is a product of the cloning strategy; this insertion has no impact on the RNAseH activity because the first 10 amino acids of HRHPL can be deleted without altering the biochemical profile of the enzyme. The DEDD active sites are indicated by a *, and the hexahistidine tag at the C-terminus is underlined. (FIG. 6B) Western analysis of RNAseH proteins in the enriched lysates probed with the anti-HBV RNAseH monoclonal antibody 9F9. (FIG. 6C) RNAseH activity of RNAseH from HBV genotypes A, B, C, D, and H detected by the oligonucleotide-directed RNA cleavage assay. HRHPL-D702A (genotype D) is a negative control. gt, genotype.

(FIG. 7A) Structure of the chimeric RNAseHs. HBV sequences are blue, HIV sequences are grey, and the hexahistidine tag is brown. The boundaries of the HIV insertions are indicated with HBV polymerase numbering in blue and HIV-1 reverse transcriptase numbering in grey. HRHPL, wild-type HBV genotype D RNAseH; *, D702A active site mutation. (FIG. 7B) Activity of the chimeric RNAseHs in the oligonucleotide-directed RNAseH assay.

(FIG. 9A) Inhibition of HBV genotype D RNAseH by irrelevant compounds at 10 µM in the oligonucleotide-directed RNAseH assay. Compound #4 was employed as an example HBV RNAseH inhibitor. (FIG. 9B) Anti-HBV RNAseH inhibitors do not significantly inhibit the HCV RNA polymerase. The ability of compounds #5, 6 and 8 to inhibit production of poly-G by the HCV RNA-directed RNA polymerase was measured in a primed homopolymeric RNA synthesis assay (Cao, et al., 2011. The compounds were employed at 10 µM. DMSO, vehicle control. (FIG. 9C) Dose-responsiveness of HBV RNAseH inhibition. The effects of compounds #6, 8, and 12 on the RNAseH activity of HRHPL (genotype D) were measured at concentrations ranging from 0.5 to 50 µM. The dose-response profile is plotted for compound #12.

(FIG. 10A) Proteins in the enriched recombinant human RNAseH1 lysates employed in the RNAseH reactions were detected by Coomassie-blue staining following SDS-PAGE. (FIG. 10B) An oligonucleotide-directed RNAseH assay was conducted with wild-type HBV RNAseH (genotype D) and recombinant human RNAseH1 under identical reaction conditions. The inhibitory compounds were employed at 10 µM. The upper and lower panels are derived from a single experiment and the data were collected on a single sheet of film, so the reactions can be directly compared. DMSO, vehicle control. S, the DRF+ substrate; P1 and P2, RNAseH cleavage products.

FIG. 13A-B. β-Thujaplicinol inhibits HBV RNAseH but not human RNAseH1. (FIG. 13A) Oligonucleotide-directed RNAseH assay performed with recombinant HBV RNAseH (genotypes D and H) and recombinant human RNAseH1 in the presence of 0, 5, or 20 μM β-thujaplicinol. Increasing amounts of β-thujaplicinol shown left to right. S, substrate RNA; P1; larger RNA cleavage product; P2; smaller RNA cleavage product. (FIG. 13B) The inhibitory 50% concentration of β-thujaplicinol was determined to be 6 μM by titrating the compound over a wide range of concentrations.

(FIG. 15A) The compound β-thujaplicinol and 11 derivatives were tested for inhibition of RNAseH. "+++" represents strong inhibition at 10 μM, "++" represents modest inhibition at 20 μM, "+" represents detectable inhibition at 60 μM, and "−" represents no inhibition at 60 μM. (FIG. 15B) Photographs of the gel runs showing the efficacy of different inhibitors.

FIG. 20. Role of RNAseH inhibitors in blocking HBV replication and cccDNA accumulation. HBV reverse transcription occurs in cytoplasmic capsid particles. The viral RNA is encapsidated by the viral capsid protein HBc, copied by the viral polymerase to minus-polarity DNA, and then plus-polarity DNA strand is made. Mature capsid particles can either be transported to the nucleus to replenish the cccDNA, or they can be secreted as virions. RNAseH inhibitors would block plus-polarity DNA synthesis and consequently would suppress both secretion of functional virions and cccDNA replenishment. The hepatocyte is represented as a rectangle, the nucleus as an oval, HBV capsid particles as hexagons, and enveloped HBV virions as hexagons within a circle. RNAs are grey and DNAs are black.

FIGS. 21A-D. RNAseH expression and activity. (FIG. 21A) Recombinant HBV RNAseH. Proteins in enriched extracts following nickel-affinity chromatography were detected by Coomassie blue staining or western analysis with monoclonal antibody 9F9 specific for the HBV RNAseH domain. D702A, RNAseH-deficient active-site mutant. (FIG. 21B) Oligonucleotide-directed RNAseH assay. Uniformly $^{32}P$-labeled RNA substrate (S) is annealed to a complementary DNA oligonucleotide. RNAseH activity cleaves the RNA in the heteroduplex formed where the oligonucleotide anneals to the RNA and yields two products (P1 and P2). (FIG. 21C) RNAseH activity of enriched recombinant HBV RNAseH. An oligonucleotide-directed RNA cleavage assay was conducted with wild-type and RNAseH-deficient (D702) HBV RNAseH. +, complementary DNA oligonucleotide employed; −, non-complementary oligonucleotide employed. (FIG. 21D) Time- and enzyme-concentration dependence of the RNAseH reaction. Reactions containing 3, 2, or 1 ng RNAseH were incubated for 20 to 90 minutes and fit to linear relationships ($R^2 > 0.97$ for each fit). Error bars are ±1 standard deviation from three experiments.

FIG. 22A-C. Inhibition of the HBV RNAseH by βTJ. (FIG. 22A) Structure of 13-Thujaplicinol. (FIGS. 22B-C) Inhibition of the HBV RNAseH by βTJ was measured with oligonucleotide-directed RNAseH assays and dose-response curves were plotted. S, substrate; P1, larger RNA cleavage product; P2, smaller RNA cleavage product. FIG. 22B. Genotype D RNAseH. FIG. 22C. Genotype H HBV RNAseH. The curves are from representative experiments and the $IC_{50}$ values are the average±1 standard deviation from three to four experiments.

FIGS. 24A-E. βTJ inhibits HBV replication by blocking the RNAseH activity. (FIG. 24A) Control assay employing wild-type or D702A RNAseH-deficient HBV genotype A. (FIG. 24B) Effect of βTJ on replication of the wild-type HBV genotype A isolate. (FIG. 24C) Effect of βTJ on replication of a wild-type HBV genotype D isolate. The top images in FIGS. 24A-C show Southern analyses of HBV capsid DNAs preparations from Huh7 cells replicating HBV. Replicate nucleic acid aliquots were either mock treated or treated with *E. coli* RNAseH to destroy RNA:DNA heteroduplexes. The positions of the mature relaxed-circular (RC), duplex linear (DL), and full-length single-stranded linear (SL) DNAs are shown. DS indicates the spectrum of double-stranded nucleic acids produced by reverse transcription, and SS indicates the spectrum of single-stranded nucleic acids. 0 µM indicates the DMSO vehicle control. The center and bottom images of panels A-C show western analyses of the HBV core protein (HBc) or β-actin in the cytoplasmic lysates. (FIG. 24D) Suppression of HBV plus-polarity DNA strand accumulation. Quantitative PCR preferential for the plus-polarity HBV DNA strand was performed on cytoplasmic capsid particle-derived nucleic acids isolated from Huh7 cells replicating genotype A HBV in the presence of βTJ. The results were normalized to the DMSO vehicle control. Error bars represent ±1 standard deviation from three independent experiments. (FIG. 24E) HBs accumulation in the medium. Medium was collected after four days incubation in the presence of the indicated concentrations of βTJ for the HBV genotype D isolate and HBs was quantified by ELISA. Error bars are ±1 standard deviation from three experiments.

FIGS. 25A-B. Cytotoxicity of βTJ. Cells were incubated with the indicated concentrations of βTJ and cellular viability was measured with MTS or membrane integrity assays at day four post-transfection. The $CC_{50}$ value is the average±1 standard deviation from three experiments. (FIG. 25A) Huh7 cells. (FIG. 25B) HepG2 cells.

DETAILED DESCRIPTION

Figure 1:
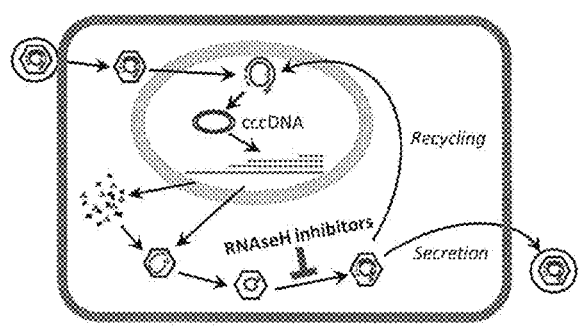
FIG. 1. The HBV replication cycle. HBV replicates by reverse transcription in the cytoplasm of infected hepatocytes. After completion of reverse transcription, intracellular capsids can either be transported into the nucleus to maintain the cccDNA pool (Recycling), or they can be enveloped and be secreted from the cells as mature virions (Secretion). Inhibiting RNAseH activity blocks plus-strand DNA synthesis during reverse transcription; this would prevent both recycling and secretion of mature virions. The hepatocyte is represented as a rectangle, the nucleus as an oval, HBV capsids as a hexagon, and the viral lipid envelop as a circle surrounding the extracellular capsids. HBV proteins are green or black, RNAs are red, and DNAs are blue.

As discussed above, the ability of the nucleos(t)ide analog drugs to profoundly suppress HBV in most patients and to cure HBV infection in a few patients confirms these drugs as first line therapies. However, the need to push the virus over the brink of elimination may not be achieved using these monotherapies alone. Other drugs used in combination with the nucleos(t)ide analogs to suppress viral replication below the level needed to maintain the cccDNA might very well achieve this goal. A logical target is the second of HBV's two enzymatic activities, the RNAseH. Here, the inventors report production of enzymatically active recombinant HBV RNAseH suitable for low throughput antiviral drug screening. Using this previously unavailable reagent, they demonstrated that the HIV RNAseH and integrase activities are similar enough to the HBV RNAseH activity to allow information derived from HIV RNAseH and integrase inhibitors to guide identification of anti-HBV RNAseH compounds. These and other aspects of the invention are described in detail below.

A. HEPATITIS B VIRUS

1. Biology

Hepatitis B virus, abbreviated HBV, is a species of the genus *Orthohepadnavirus*, which is likewise a part of the Hepadnaviridae family of viruses. This virus causes the disease hepatitis B. In addition to causing hepatitis B, infection with HBV can lead to cirrhosis and hepatocellular carcinoma. It has also been suggested that it may increase the risk of pancreatic cancer.

The hepatitis B virus is classified as the type species of the *Orthohepadnavirus*, which contains three other species: the Ground squirrel hepatitis virus, Woodchuck hepatitis virus, and the Woolly monkey hepatitis B virus. The genus is classified as part of the Hepadnaviridae family, which contains two other genera, the *Avihepadnavirus* and a second which has yet to be assigned. This family of viruses have not been assigned to a viral order. Viruses similar to hepatitis B have been found in all the Old World apes (orangutan, gibbons, gorillas and chimpanzees) and from a New World woolly monkey suggesting an ancient origin for this virus in primates.

The virus is divided into four major serotypes (adr, adw, ayr, ayw) based on antigenic epitopes present on its envelope proteins, and into eight genotypes (A-H) according to overall nucleotide sequence variation of the genome. The genotypes have a distinct geographical distribution and are used in tracing the evolution and transmission of the virus. Differences between genotypes affect the disease severity, course and likelihood of complications, and response to treatment and possibly vaccination.

Hepatitis B virus is a member of the Hepadnavirus family. The virus particle (virion) consists of an outer lipid envelope and an icosahedral nucleocapsid core composed of protein. The nucleocapsid encloses the viral DNA and a DNA polymerase that has reverse transcriptase activity similar to retroviruses. The outer envelope contains embedded proteins which are involved in viral binding of, and entry into, susceptible cells. The virus is one of the smallest enveloped animal viruses with a virion diameter of 42 nm, but pleomorphic forms exist, including filamentous and spherical bodies lacking a core. These particles are not infectious and are composed of the lipid and protein that forms part of the surface of the virion, which is called the surface antigen (HBsAg), and is produced in excess during the life cycle of the virus. It consists of HBsAg, HBcAg (HBeAg is an amino-terminal extension of HBcAg initiating from an upstream start codon), Hepatitis B virus DNA polymerase, and HBx. The functions of this non-structural regulatory protein are not yet well known.

The genome of HBV is made of circular DNA, but it is unusual because the DNA is not fully double-stranded. One end of the full length strand is linked to the viral DNA polymerase. The genome is 3020-3320 nucleotides long (for the full length strand) and 1700-2800 nucleotides long (for the short length strand). The negative-sense, (non-coding), is complementary to the viral mRNA. The viral DNA is found in the nucleus soon after infection of the cell. The partially double-stranded DNA is rendered fully double-stranded by completion of the (+) sense strand and removal of a protein molecule from the (−) sense strand and a short sequence of RNA from the (+) sense strand. A short terminal duplication of are removed from the ends of the (−) sense strand and the ends are rejoined. The mature nuclear form of the genome is called the "cccDNA".

There are four known genes encoded by the genome called C, X, P, and S. The core protein is coded for by gene C (HBcAg), and its start codon is preceded by an upstream in-frame AUG start codon from which the pre-core protein is produced. HBeAg is produced by proteolytic processing of the pre-core protein. The DNA polymerase is encoded by gene P. Gene S is the gene that codes for the surface antigen (HBsAg). The HBsAg gene is one long open reading frame but contains three in frame "start" (ATG) codons that divide the gene into three sections, pre-S1, pre-S2, and S. Because of the multiple start codons, polypeptides of three different sizes called large, middle, and small (pre-S1+pre-S2+S, pre-S2+S, or S) are produced. The function of the protein coded for by gene X is not fully understood.

There are eight known genotypes labeled A through H. A possible new "I" genotype has been described, but acceptance of this notation is not universal. Different genotypes may respond to treatment in different ways. The genotypes differ by at least 8% of the sequence and have distinct geographical distributions and this has been associated with anthropological history. Type F which diverges from the other genomes by 14% is the most divergent type known. Type A is prevalent in Europe, Africa and South-east Asia, including the Philippines. Type B and C are predominant in Asia; type D is common in the Mediterranean area, the Middle East and India; type E is localized in sub-Saharan Africa; type F (or H) is restricted to Central and South America. Type G has been found in France and Germany. Genotypes A, D and F are predominant in Brazil and all genotypes occur in the United States with frequencies dependent on ethnicity. The E and F strains appear to have originated in aboriginal populations of Africa and the New World, respectively. Within genotypes 24 subtypes have been described which differ by 4-8% of the genome:

Type A has two subtypes: Aa (A1) in Africa/Asia and the Philippines and Ae (A2) in Europe/United States.

Type B has two distinct geographical distributions: Bj/B1 ('j'—Japan) and Ba/B2 ('a'—Asia). Type Ba has been further subdivided into four clades (B2-B4).

Type C has two geographically subtypes: Cs (C1) in South-east Asia and Ce (C2) in East Asia. The C subtypes have been divided into five clades (C1-C5). A sixth clade (C6) has been described in the Philippines but only in one isolate to date. Type C1 is associated with Vietnam, Myanmar and Thailand; type C2 with Japan, Korea and China; type C3 with New Caledonia and Polynesia; C4 with Australia; and C5 with the Philippines. A further subtype has been described in Papua, Indonesia.

Type D has been divided into 7 subtypes (D1-D7).

Type F has been subdivided into 4 subtypes (F1-F4). F1 has been further divided in to 1a and 1b. In Venezuela subtypes F1, F2, and F3 are found in East and West Amerindians. Among South Amerindians only F3 was found. Subtypes Ia, III, and IV exhibit a restricted geographic distribution (Central America, the North and the South of South America respectively) while clades Ib and II are found in all the Americas except in the Northern South America and North America respectively.

The life cycle of hepatitis B virus is complex (FIG. 20). Hepatitis B is one of a few known non-retroviral viruses which use reverse transcription as a part of its replication process:

Attachment—The virus gains entry into the cell by binding to a receptor on the surface of the cell and enters it by endocytosis.

Penetration—The virus membrane then fuses with the host cell's membrane releasing the DNA and core proteins into the cytoplasm.

Uncoating—Because the virus multiplies via RNA made by a host enzyme, the viral genomic DNA has to be transferred to the cell nucleus by host proteins. The core proteins dissociate from the partially double-stranded viral DNA is then made fully double-stranded and transformed into covalently closed circular DNA (cccDNA) that serves as a template for transcription of four viral mRNAs.

Replication—The cccDNA is the transcriptional template for all of HBV's RNAs. The largest of the mRNAs is called the pre-genomic RNA. This mRNA is longer than the viral genome and is packaged into nascent capsids along with the viral polymerase. Reverse transcription within the capsids is catalyzed by the coordinate activity of the polymerase's reverse transcriptase and ribonuclease H activities and results in the partially double-stranded viral DNA found within HBV virions.

Assembly and Release—Progeny virions are formed budding of the viral capsid particles containing the viral DNA into endoplasmic-reticulum-derived membranes, where they pick up their envelope and HBsAgs are released from the cell by non-cytolytic secretion or are returned to the nucleus and re-cycled to produce even more copies of the nuclear cccDNA.

2. Treatment

Currently, there are seven FDA approved drugs in the U.S. to treat chronic HBV: Intron A® (Interferon Alpha), Pegasys® (Pegylated Interferon), Epivir HBV® (Lamivudine), Hepsera® (Adefovir), Baraclude® (Entecavir), Tyzeka® (Telbivudine), and Viread® (Tenofovir).

Adefovir, previously called bis-POM PMEA, with trade names Preveon® and Hepsera®, is an orally-administered nucleotide analog reverse transcriptase inhibitor (ntRTI). It can be formulated as the pivoxil prodrug adefovir dipivoxil. Adefovir works by blocking reverse transcriptase, the enzyme that is crucial for the hepatitis B virus (HBV) to reproduce in the body because it synthesizes the viral DNA. It is approved for the treatment of chronic hepatitis B in adults with evidence of active viral replication and either evidence of persistent elevations in serum aminotransferases (primarily ALT) or histologically active disease. The main benefit of adefovir over drugs like lamivudine (below) is that it takes a much longer period of time before the virus develops resistance to it. Adefovir dipivoxil contains two pivaloyloxymethyl units, making it a prodrug form of adefovir.

Lamivudine (2',3'-dideoxy-3'-thiacytidine, commonly called 3TC) is a potent nucleoside analog reverse transcriptase inhibitor (nRTI). It is marketed by GlaxoSmithKline with the brand names Zeffix®, Heptovir®, Epivir®, and Epivir-HBV®. Lamivudine has been used for treatment of chronic hepatitis B at a lower dose than for treatment of HIV. It improves the seroconversion of e-antigen positive hepatitis B and also improves histology staging of the liver. Long term use of lamivudine unfortunately leads to emergence of a resistant hepatitis B virus (YMDD) mutant. Despite this, lamivudine is still used widely as it is well tolerated.

Lamivudine is an analogue of cytidine. It can inhibit both types (1 and 2) of HIV reverse transcriptase and also the reverse transcriptase of hepatitis B. It is phosphorylated to active metabolites that compete for incorporation into viral DNA. They inhibit the HIV reverse transcriptase enzyme competitively and act as a chain terminator of DNA synthesis. The lack of a 3'—OH group in the incorporated nucleoside analogue prevents the formation of the 5' to 3' phosphodiester linkage essential for DNA chain elongation, and therefore, the viral DNA growth is terminated.

Lamivudine is administered orally, and it is rapidly absorbed with a bio-availability of over 80%. Some research suggests that lamivudine can cross the blood-brain barrier. Lamivudine is often given in combination with zidovudine, with which it is highly synergistic. Lamivudine treatment has been shown to restore zidovudine sensitivity of previously resistant HIV. Lamivudine showed no evidence of carcinogenicity or mutagenicity in in vivo studies in mice and rats at doses from 10 to 58 times those used in humans.

Entecavir, abbreviated ETV, is an oral antiviral drug used in the treatment of hepatitis B infection. It is marketed under the trade names Baraclude® (BMS) and Entaliv® (DRL). Entecavir is a nucleoside analog (more specifically, a guanosine analogue) that inhibits reverse transcription, DNA replication and transcription in the viral replication process. The drug's manufacturer claims that entecavir is more efficacious than previous agents used to treat hepatitis B (lamivudine and adefovir). Entecavir was approved by the U.S.FDA in March 2005 and is used to treat chronic hepatitis B. It also helps prevent the hepatitis B virus from multiplying and infecting new liver cells. Entecavir is also indicated for the treatment of chronic hepatitis B in adults with HIV/AIDS infection. However, entecavir is not active against HIV.

Telbivudine is an antiviral drug used in the treatment of hepatitis B infection. It is marketed by Swiss pharmaceutical company Novartis under the trade names Sebivo® (Europe) and Tyzeka® (United States). Clinical trials have shown it to be significantly more effective than lamivudine or adefovir, and less likely to cause resistance. Telbivudine is a synthetic thymidine nucleoside analogue; it is the L-isomer of thymidine. It is taken once daily.

Tenofovir disoproxil fumarate (TDF or PMPA), marketed by Gilead Sciences under the trade name Viread®, it is also a nucleotide analogue reverse transcriptase inhibitor (nRTIs) which blocks the HBV reverse transcriptase, an enzyme crucial to viral production. Tenofovir disoproxil fumarate is a prodrug form of tenofovir. Tenofovir is also available in a fixed-dose combination with emtricitabine in a product with the brand name Truvada for once-a-day dosing. Atripla, a fixed-dose triple combination of tenofovir, emtricitabine and efavirenz, was approved by the FDA on 12 Jul. 2006 and is now available, providing a single daily dose for the treatment of HIV. Tenofovir is indicated in combination with other antiretroviral agents for the treatment of HIV-1 infection in adults. This indication is based on analyses of plasma HIV-1 RNA levels and CD4 cell counts in controlled studies of tenofovir in treatment-naive and treatment-experienced adults. There are no study results demonstrating the effect of tenofovir on the clinical progression of HIV. It also has activity against wild-type and lamivudine-resistant HBV.

B. HBV RNASE H

RNAseH enzymes hydrolyze RNA in an RNA:DNA heteroduplex (Hostomsky et al., 1993). They belong to the nucleotidyl transferase superfamily whose members share a similar protein fold and presumably have similar enzymatic mechanisms (Steitz, 1995). This family includes *E. coli* RNAseH I and II (Katayanagi et al., 1990; Yang et al., 1990 and Lai et al., 2000), DNA transposases including the Tn5 transposase (Rice et al., 2001), retroviral integrases including the HIV integrase (Hickman et al., 1994), the RuvC Holiday junction resolvase (Ariyoshi et al., 1994), the Argonaute RNAse (Parker et al., 2004 and Song et al., 2004), and human RNAseH 1 and 2 (Lima et al., 2001; Braunshofer-Reiter et al., 1998 and Braunshofer-Reiter et al., 1998). The canonical RNAseH structure contains about 100 aa including four conserved carboxylates (the "DEDD" motif) that coordinate two divalent cations (Nowotny et al., 2005). The RNAseH mechanism is believed to involve both divalent cations (Steitz, 1995; Klumpp et al., 2003 and Nowotny et al., 2006), although a one-ion mechanism has been proposed (Keck et al., 1998 and Goedken et al., 2001). The HBV RNAseH domain shares low but recognizable (~16-18%) homology with the RNAseH domains of reverse transcriptases and other retro-elements (Li et al., 1995; McClure, 1993 and Poch et al., 1989).

The HBV RNAseH is encoded at the carboxy-terminus of the viral polymerase protein that also encodes the viral DNA polymerase activity (reverse transcriptase). The high hydrophobicity of the HBV polymerase and its existence as a complex with host chaperones (Hu et al. 1996; Hu et al., 1997) have severely restricted study of the HBV RNAseH. Furthermore, we demonstrated that the RNAseH in its native context within the polymerase protein is unable to accept exogenous heteroduplex substrates (Levrero et al., 2009), analogous to the inability of the DNA polymerase active site to engage exogenous primer-templates (Zoulim, 2004). Consequently, most of our limited knowledge of the RNAseH comes from mutational studies of the viral genome in the context of viral replication conducted by us and others (Tuttleman et al., 1986; Werle-Lapostolle, et al., 2004; Cheng, et al., 2011; Wong et al., 2006; Coffin, et al., 2011 and Monto, et al., 2010). These restrictions have prevented biochemical characterization of the RNAseH and blocked biochemical screens for anti-HBV RNAseH drugs to date.

C. PURIFICATION METHODS

As used herein, "purified" refers to a purity that allows for the effective use of the protein in vitro, ex vivo, or in vivo. For a protein to be useful in in vitro, ex vivo, or in vivo applications, it should be substantially free of contaminants, other proteins, and/or chemicals that could interfere with the use of that protein in such applications, or that at least would be undesirable for inclusion with the protein of interest. Such applications include use of the protein in inhibition assays or in other methods of interest. Preferably, a "purified" HBV RNAse H protein, as referenced herein, is a protein that has a purity significantly higher than would be found in mammalian tissue infected by HBV, e.g., at least 2, 5, 10, 50, 100, 500, or 1000 times more concentrated than in such mammalian tissue. "Purified" can also mean that the protein has been purified from other protein components such that the protein comprises at least about 1% weight/weight of the total protein in a given composition, and more preferably, at least about 2%, 5%, 10%, 20% 30%, 40%, 50%, 60%, 70%, 80% or more of the total protein in the composition. In some embodiments, it may comprise at least 90%, 91%, 92%, 93%, 94%, 95%, 96%, 97%, 98%, or 99% weight/weight of the total protein in a given composition.

As used herein, "isolated" refers to a protein that has been separated from a majority of the material (excluding water) with which it is associated in nature. In the case of HBV RNAse H protein, it means that more than 50% of such material in mammalian tissue infected with HBV has been removed from the RNAse H (or the RNAse H has been removed from such material), and more preferably that the RNAse H is in contact with less than about 40%, 30%, 20%, 15%, 10%, 9%, 8%, 7%, 6%, 5%, 4%, 3%, 2%, or 1% of the non-water materials with which HBV RNAse H would ordinarily be combined in such infected mammalian tissue.

In some embodiments, there is provided a new method for the purification of HBV RNAse H that, for the first time, permits demonstrable, confirmed and reproducible production of active enzyme.

The RNAseH is expressed in *E. coli* induced using any of the standard inducible protein expression vectors, such as pTrcHis2B from Invitrogen. The gene to be employed includes a carboxy-terminal hexahistidine affinity tag. Expression of the protein is induced for a moderate amount of time by the appropriate inducing agent, such as 3-8 hours at 30° to 37° C. with 0.1-1.0 mM IPTG. Cells are collected and lysed on ice by sonication or other physical disruption means in a buffer with high salt, moderate concentrations of non-ionic detergent, moderate pH, low concentrations of imidazole and strong reducing conditions (for example, 0.8-1.2 M NaCl, 1-3% NP-40, pH 7.0-8.0, 20-50 mM imidazole, and 2-5 mM DTT). The lysates are clarified by centrifugation and the RNAseH is bound to a nickel-affinity matrix. The matrix is washed with 10-50 column volumes of lysis buffer, eluted with >300 mM imidazole in lysis buffer, and dialyzed into a storage buffer containing moderate NaCl concentrations, moderate pH, a stabilizer such as glycerol, and strong reducing conditions, for example 200-500 mM NaCl, pH 7.0-8.0, 10-30% glycerol, and ≥4 mM DTT. The protein can be stored for at least 3 months in liquid nitrogen.

1. HBV RNAseH Induction

A specific induction protocol for RNAseH expression may be performed as follows. HBV RNAseH expression vectors are transformed into BL21-DE3(codon plus) cells. A 25 ml LB-amp-cm culture is inoculated and incubated at 37° C. overnight. The overnight culture is diluted with 75 ml LB-amp-cm. 0.1 mM IPTG and 1% sorbitol is used to induce and the culture is incubated at 37° C. for 6 hours. Cells are collected by centrifugation and either use immediately or store bacterial pellet at −75° C.

2. HBV RNAseH Purification

A specific purification protocol for RNAseH expression may be performed as follows:
1. Thaw frozen cell pellet from a 100 ml induction on ice.
2. Resuspend pellet in 20 ml wash buffer plus protease inhibitors and 2 mM DTT (40 µl 1M DTT and 200 µl protease inhibitors per 20 ml).
3. Transfer resuspended pellet to a cold oakridge tube. Sonicate at 70% for 3 bursts of 20 seconds with a probe sonicator. Keep sample cold at all times.
4. Clarify the lysate by centrifuging in an SS-34 rotor at 40 for 10 min. at 10K RPM.
5. Transfer supernatant to 50 ml conical tube. Save 100 µl as the "lysate" fraction.
6. Equilibrate Ni-NTA beads in wash buffer plus protease inhibitors and 2 mM DTT.
   Pipet 200 µl of Ni-NTA for each sample to an eppendorf tube using wide bore tips.
   Add 1 ml of equilibration buffer. Vortex, spin down beads and remove supernatant.
   Wash again with 1 ml of wash buffer.
   Suspend beads in 1 ml of wash buffer
7. Add equilibrated beads to the lysate and rock in the cold room for 1.5-2.5 hours.
8. Transfer lysate/bead suspension to a 1 ml polypropylene column in the cold room. Allow supernatant to flow through column to pack the beads. Save 100 µl as the "flow-through" fraction.
9. Wash each column with 20 ml of wash solution plus 40 ul 1M DTT and 200 µl protease inhibitors in the cold room.
10. Elute with 2 ml of elution solution plus 2 mM DTT and protease inhibitors (4 µl 1M DTT and 20 ul protease inhibitors). Collect ~750 ul in the first fraction and ~600 µl in fractions 2 and 3.
11. Resolve 16 µl of each elution fraction on a 12% SDS page gel. For controls include 5 µl of lysate, 5 µl of the follow-through, and a molecular weight marker.
12. Pool fractions with significant protein yield (use the 25 kDa SlyD protein as a surrogate for the RNAseH; usually only fraction 1 is saved) and dialyze overnight into 500 ml dialysis buffer per sample.
13. Aliquot to 200 µl fractions and store in LN₂ until needed.
14. Resolve 16 µl of the dialyzed protein on a 15% SDS-PAGE gel and western blot using the mouse monoclonal antibody 9F9 (Santa Cruz Biotech) to monitor yield of the RNAseH. Do all incubations and washes at 4° C.; the primary incubation should be overnight, the secondary incubation can be for 2-3 hours.

Purification Solutions

Wash Solution

| | 100 ml |
|---|---|
| 50 mM hepes pH 8.0 | 5 ml (1M stock) |
| 1.2M NaCl | 24 ml (5M stock) |
| 1.0% NP40 | 1 ml |
| 27.5% glycerol | 27.5 ml (34.65 g) |
| 20 mM imidazole | 800 µl (2.5M stock) |
| diH₂O to 100 ml | |

Add Just Before Use:
2 mM DTT
Protease inhibitors
Elution Buffer

| | 100 ml |
|---|---|
| 50 mM hepes pH 8.0 | 5 ml (1M stock) |
| 0.3M NaCl | 6 ml (5M stock) |
| 0.1% NP40 | 100 µl |
| 27.5% glycerol | 27.5 ml (34.65 g) |
| 350 mM imidizole | 14 ml (2.5M stock) |

1M Hepes pH 8.0
  23.83 g to 100 ml
Dialysis Solution

| | 2 L |
|---|---|
| 50 mM hepes pH 7.3 | 100 ml (1M stock) |
| 0.3M NaCl | 120 ml (5M stock) |
| 20% glycerol | 400 ml (504 g) |
| 5 mM DTT | 1.542 g |
| diH₂O to 2 L | |

Protease Inhibitors
  Sigma P-8849 5 ml
  Sigma P-8849 1 ml

D. SCREENING METHODS

Also contemplated is the screening of compounds for their ability to inhibit HBV RNAse H. The ability of the present inventors to reproducibly produce a functional enzyme provides the ability to test various compounds for therapeutic activity. In the screening assays, the candidate substance may first be screened for basic biochemical activity, e.g., binding to RNAse H, and/or inhibiting its activity, and then tested for its ability to inhibit the enzyme, at the cellular, tissue or whole animal level. Thus, in particular embodiments, screening assays may be performed in vitro, in cyto or in vivo.

Some embodiments described herein relate generally to a method for determining the ability of a candidate substance to inhibit HBV, generally including the steps of: (a) providing a source of HBV RNAse H enzyme; (b) contacting the enzyme with a candidate substance; (c) determining the enzyme function in step (b); and (d) comparing the enzyme function in step (c) with the enzyme function of the enzyme in the absence of the candidate substance, wherein decreased enzyme function in the presence of the candidate substance, as compared to enzyme function in the absence of the candidate substance, identifies the candidate substance as an inhibitor of HBV.

Some embodiments described herein relate generally to a method for determining the ability of a candidate substance to inhibit HBV, generally including the steps of: (a) providing a cell culture that is actively replicating HBV (for example the HepG2.2.15 cell line, or the HepG2 or Huh7 cell lines transfected with an HBV genomic expression vector); adding the test compound to the cell culture supernatant; (c) isolating viral nucleic acids from within intracellular or extracellular capsid particles; and (d) detecting suppression of viral genomic replication with the appropriate characteristics stemming from suppression of RNAseH activity. Such products can be detected in multiple manners, including but not limited to: (i) Southern analysis of HBV DNAs in which replicate samples have been either mock-treated or treated with exogenous RNAseH to destroy the RNA:DNA heteroduplexes that accumulate in the absence of RNAseH action. In this case, the signature of inhibiting the RNAseH would be an increase in electrophoretic mobility of the nucleic acids following treatment with exogenous RNAseH; or (ii) Real-time PCR analysis of the nucleic acid. In another embodiment of the real-time method, the real-time PCR detection system preferentially detects HBV positive-polarity DNAs because positive-polarity DNA synthesis is blocked when the RNA template is not degraded by the HBV RNAseH during negative-polarity DNA synthesis. In this case, preferential amplification of the plus-polarity DNA is achieved by flanking the gap in the minus-polarity HBV DNA with the amplification primers for real-time PCR.

Alternatively, a quick, inexpensive and easy assay to run is a binding assay. Binding of a molecule to a target may, in and of itself, be inhibitory, due to steric, allosteric or charge-charge interactions. This can be performed in solution or on a solid phase and can be utilized as a first round screen to rapidly eliminate certain compounds before moving into more sophisticated screening assays. In one embodiment of this kind, the screening of compounds that bind to HBV RNAse H or fragment thereof is provided.

The HBV RNAse H may be either free in solution or fixed to a support. Either the HBV RNAse H or the compound (or both) may be labeled, thereby permitting determining of binding. In another embodiment, the assay may measure the inhibition of binding of HBV RNAse H to a natural or artificial substrate. Competitive binding assays can be performed in which one or both of the agents are labeled. Usually, the target will be the labeled species, decreasing the chance that the labeling will interfere with the HBV RNAse H's binding function. One may measure the amount of free label versus bound label to determine binding or inhibition of binding.

A technique for high throughput-screening of compounds is described in WO 84/03564. Large numbers of small peptide test compounds are synthesized on a solid substrate, such as plastic pins or some other surface. The peptide test compounds are reacted and washed. Bound polypeptide is detected by various methods. Purified HBV RNAse H can be coated directly onto plates for use in the aforementioned drug screening techniques. However, non-neutralizing antibodies may be used to immobilize the enzyme to a solid phase. Also, fusion proteins containing a reactive region (preferably a terminal region) may be used to link an active region to a solid phase.

Subsequently, the compounds described herein may be tested for activity in HBV RNAse H-expressing cells, including those infected with HBV, and in animal models of disease. Treatment of these animals with test compounds will involve the administration of the compound, in an appropriate form, to the animal. Administration will be by any route the could be utilized for clinical or non-clinical purposes, including but not limited to oral, nasal, buccal, or even topical. Alternatively, administration may be by intratracheal instillation, bronchial instillation, intradermal, subcutaneous, intramuscular, intraperitoneal or intravenous injection. Specifically contemplated are systemic intravenous injection, regional administration via blood or lymph supply.

1. Exemplary Assay Conditions

The following is an exemplary protocol for an HBV RNAseH assay. The standard substrate is $^{32}$P-labeled DRF+ RNA and standard oligos are D2526+(negative control) and D2507− at a concentration of 1 µg/µl. An optional positive control is 0.2 µl of *E. coli* RNAseH. Reaction components are as follows:

| Component | 1x |
| --- | --- |
| Protein extract | 6 µl |
| 10x RH buffer | 2 |
| DNA oligo | 3 |
| *RNA | 1 |
| RNAseOut | 0.5 |
| Test compound | 2 |
| 0.5% NP40 | 2 |
| DEPC H$_2$O | 3.5 |
| Total volume | 20 µl |

1. Assemble reactions on ice:
    a. Dilute test compound to 10x desired concentration with 10% DMSO in DEPC H$_2$O.
    b. Put H$_2$O, NP40, buffer, RNAseOut in each reaction tube (RNaseOUT Recombinant Ribonuclease Inhibitor is an acidic protein with a molecular weight of ~52 kDa available from Life Technologies).
    c. Add 3 µl of the appropriate DNA oligo to each reaction tube.
    d. Add 2 µl test compound to each reaction tube.
    e. Add 6 µl protein to each reaction tube.
    f. Add 1 µl RNA substrate to each reaction tube.
2. Incubate reactions at 42° C. for 90 min. Stop reactions with 5 µl 5x sample buffer or 80 µl formamide loading buffer depending on gel system to be used.
3. Run reactions on 12% SDS PAGE or 6% acrylamide/6M urea gels. Boil samples for 5 min., then load 12 µl/lane for SDS-PAGE or 50 µl/lane for urea gels. Store remaining reactions at −80° C. in case the samples need to be re-run. Stop gel when dye front is ~0.5 cm from bottom. Cut off dye front and stacking gel (discard them in radioactive waste).
4. Stain SDS-PAGE gels with Coomassie blue and then destain until can see the protein bands (does not need to be fully destained). Wash acrylamide/urea gels in dH$_2$O for 30 min. to remove the urea.
5. Dry gel. Place on film with intensifier screen at −80° C. for 3 hours to 1.5 days, depending on how fresh the RNA is.

2. 6% Sequencing Gels for RNAseH Assays

The follow protocol can be used for testing RNAseH activity and for screening of inhibitors. To use this gel system, one stops the standard 20 μl RNAseH reactions with 80 μl 1× formamide loading buffer per reaction:

1. The gels are 6% acrylamide/6M urea in 1×TBE. Warm the 6% Sequencing Acrylamide solution to near room temperature and check to be sure the urea has not crystallized before pouring a gel.
2. Pour the gel. Set up a vertical mini-gel plate as usual. Use thick spacers (1.5 mm). Pour a single phase gel and insert the comb. Each minigel needs 20 ml 6% Sequencing Acrylamide mix. Initiate with 150 μl 10% APS and 20 ul TMED. The gel will be ready to use in ~40 minutes.
3. Remove casting clamps, rinse the plates carefully with dH$_2$O and remove the comb. Mount the gel in a minigel rig as usual, using 1×TBE as the running buffer. Immediately rinse the residual unpolymerized acrylamide and urea from the wells using a syringe and needle.
4. Pre-run the gel for ~5 min. Set the original current to ~40 mA (~220-230V). Turn off current prior to loading the gel.
5. Heat samples to >90° C. for 3-5 min. and chill them immediately on ice. Rinse the wells in the gel again with a syringe and needle to remove urea that has diffused into the wells. Promptly load 50 μl of sample per well.
6. Electrophorese at ~40 mA (~220-230V) until the faster-migrating dye (bromophenol blue) is near the bottom of the gel. Cut the bromophenol blue band from the bottom of the gel and discard it in the radioactive trash.
7. Soak gel in dH$_2$O with shaking for 30-45 min. to remove the urea. Change the water 2 or 3 times during the soaking phase.
8. Dry the gel at 80° C. under vacuum for ~1 hour. Check the surface of the dried gel—if it is sticky, dust it with baby powder and wipe the gel with a kimwipe to remove the excess powder. Expose to film as usual.

E. CHEMICAL ENTITIES

1. Compounds

Compounds described herein are represented by Formulas I, II, III, and IV below:

FORMULA I

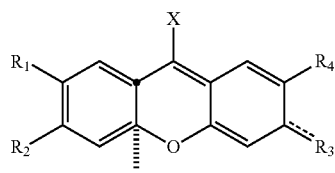

wherein $R_1$ is —OH; $R_2$ is —OH; $R_3$ is —OH or O; $R_4$ is —OH; and X is H, methyl, substituted or unsubstituted phenyl or piperidine; and

FORMULA II

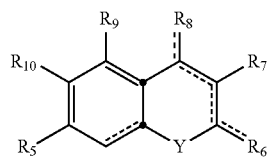

wherein $R_5$ is H, —OH or $C_1$-$C_6$ alkoxy; $R_6$ is H, O or substituted or unsubstituted phenyl; $R_7$ is H, —OH or —COOH; $R_8$ is —CH$_3$ or O; $R_9$ is —OH or H; $R_{10}$ is H, —OH, $C_1$-$C_4$ alkyl optionally substituted with substituted or unsubstituted phenyl; Y is O or NR$_{11}$, wherein R$_{11}$ is branched or straight-chain $C_1$-$C_6$ alkyl or hydroxyalkyl. or

FORMULA III

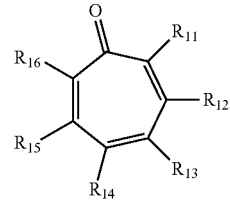

wherein: $R_{11}$ is hydrogen, —OR$_{17}$, hydroxy, or halo, wherein $R_{17}$ is $C_1$-$C_8$ acyl, $C_1$-$C_8$ alkyl, or a substituted version of either of these groups; $R_{12}$ is hydrogen, hydroxy or halo; $R_{13}$ and $R_{14}$ are each independently hydrogen, hydroxy, nitroso, $C_1$-$C_{12}$ alkyl, $C_1$-$C_{12}$ alkenyl, $C_1$-$C_{12}$ alkynyl, $C_1$-$C_{12}$ aryl, $C_1$-$C_{12}$ aralkyl, $C_1$-$C_{12}$ amido, or a substituted version of any of these groups, or $R_{13}$ is taken together with $R_{14}$ as provided below; $R_{15}$ is hydrogen, $C_1$-$C_{12}$ alkyl, $C_1$-$C_{12}$ alkenyl, $C_1$-$C_{12}$ alkynyl, $C_1$-$C_{12}$ aryl, $C_1$-$C_{12}$ aralkyl,

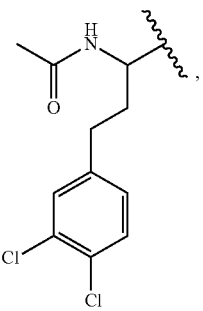 [SMILES: *C(CCc1ccc(Cl)c(Cl)c1)NC(C)=O]

or a substituted version of any of these groups; and $R_{16}$ is hydrogen, unsubstituted $C_1$-$C_6$ alkyl, substituted $C_1$-$C_6$ alkyl, or hydroxyl; provided that when $R_{13}$ and $R_{14}$ are taken together as further defined by FORMULA IV:

FORMULA IV

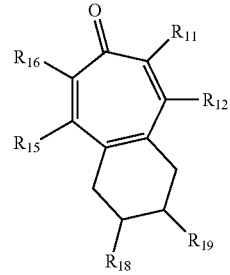

$R_{18}$ and $R_{19}$ are each independently hydrogen, $C_1$-$C_6$ alkyl, $C_1$-$C_6$ alkenyl, or $C_1$-$C_6$ alkynyl.

In particular, the compound of FORMULA I will have X being phenyl substituted with O or NR$_{12}$R$_{13}$ at the para position, wherein R$_{12}$ and R$_{13}$ are H or —CH$_3$. In another particular example, the compound of FORMULA II will have $R_6$ as di- or tri-substituted phenyl. Also, where the compound is of FORMULA II, $R_{10}$ will be $CH_2R_{14}$, wherein $R_{14}$ is halogen-disubstituted phenyl. In another particular example, the compound is of FORMULA III and $R_{11}$ is hydroxy. Also, in another particular example, the compound is of FORMULA III and at least one of $R_{12}$, $R_{13}$, $R_{14}$ or $R_{15}$ is $C_1$-$C_{12}$-alkyl. In another particular example, the compound is of FORMULA IV and $R_{18}$ is $C_1$-$C_6$ alkenyl.

Other particular compounds include:

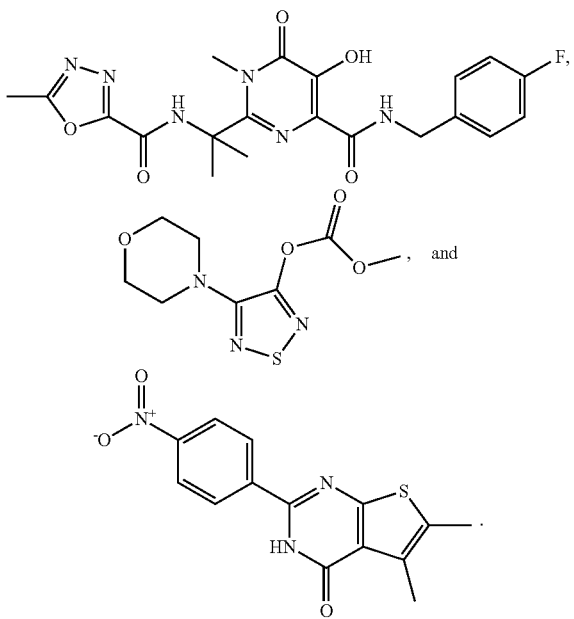

Compounds described herein may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds can have the S or the R configuration.

Chemical formulas used to represent compounds described herein will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

Compounds described herein may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the compounds described herein are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$. Similarly, it is contemplated that one or more carbon atom(s) of a compound described herein may be replaced by a silicon atom(s). Furthermore, it is contemplated that one or more oxygen atom(s) of a compound described herein may be replaced by a sulfur or selenium atom(s).

Compounds described herein may also exist in prodrug form. Since prodrugs are known to enhance numerous desirable qualities of pharmaceuticals (e.g., solubility, bioavailability, manufacturing, etc.), the compounds employed in some methods described herein may, if desired, be delivered in prodrug form. Thus, prodrugs of compounds described herein as well as methods of delivering prodrugs. Prodrugs of the compounds may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

2. Chemical Definitions

When used in the context of a chemical group, "hydrogen" means —H; "hydroxy" means —OH; "oxo" means =O; "halo" means independently —F, —Cl, —Br or —I; "amino" means —$NH_2$; "hydroxyamino" means —NHOH; "nitro" means —$NO_2$; "nitroso" means —NO; imino means =NH; "cyano" means —CN; "isocyanate" means —N=C=O; "azido" means —$N_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; "thio" means =S; "sulfonyl" means —S(O)$_2$—; and "sulfinyl" means —S(O)—.

In the context of chemical formulas, the symbol "—" means a single bond, "=" means a double bond; and "≡" means triple bond. The symbol "----" represents an optional bond, which if present is either single or double. The symbol '' represents a single bond or a double bond. Thus, for example, the structure includes the structures

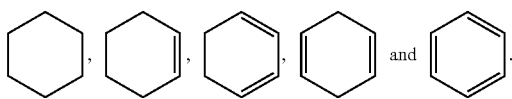

As will be understood by a person of skill in the art, no one such ring atom forms part of more than one double bond. The symbol " ~~ ", when drawn perpendicularly across a bond indicates a point of attachment of the group. It is noted that the point of attachment is typically only identified in this manner for larger groups in order to assist the reader in rapidly and unambiguously identifying a point of attachment. The symbol "◄━" means a single bond where the group attached to the thick end of the wedge is "out of the page." The symbol "▫▫▫▫" means a single bond where the group attached to the thick end of the wedge is "into the page". The symbol " ~~ " means a single bond where the conformation (e.g., either R or S) or the geometry is undefined (e.g., either E or Z).

Any undefined valency on an atom of a structure shown in this application implicitly represents a hydrogen atom bonded to the atom. When a group "R" is depicted as a "floating group" on a ring system, for example, in the formula:

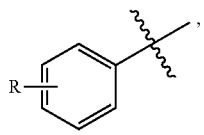

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

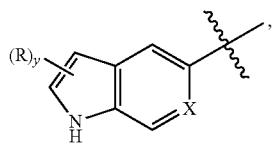

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. For example, "alkoxy$_{(C≤10)}$" designates those alkoxy groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "saturated" as used herein means the compound or group so modified has no carbon-carbon double and no carbon-carbon triple bonds, except as noted below. The term does not preclude carbon-heteroatom multiple bonds, for example a carbon oxygen double bond or a carbon nitrogen double bond. Moreover, it does not preclude a carbon-carbon double bond that may occur as part of keto-enol tautomerism or imine/enamine tautomerism.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl). When the term "aliphatic" is used without the "substituted" modifier only carbon and hydrogen atoms are present. When the term is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl. The groups —CH$_3$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neopentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, —CH$_2$CH$_2$CH$_2$—, and

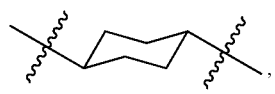 [SMILES: *C1CCC(*)CC1]

are non-limiting examples of alkanediyl groups. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =CH$_2$, =CH(CH$_2$CH$_3$), and =C(CH$_3$)$_2$. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which one or more hydrogen atoms has been substituted with a halo group and no other atoms aside from carbon, hydrogen and halogen are present. The group, —CH$_2$Cl is a non-limiting examples of a haloalkyl. An "alkane" refers to the compound H—R, wherein R is alkyl. The term "fluoroalkyl" is a subset of substituted alkyl, in which one or more hydrogen has been substituted with a fluoro group and no other atoms aside from carbon, hydrogen and fluorine are present. The groups, —CH$_2$F, —CF$_3$, and —CH$_2$CF$_3$ are non-limiting examples of fluoroalkyl groups. An "alkane" refers to the compound H—R, wherein R is alkyl.

The term "alkenyl" when used without the "substituted" modifier refers to an monovalent unsaturated aliphatic group with a carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CH—C$_6$H$_5$. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH$_3$)CH$_2$—, —CH=CHCH$_2$—, and

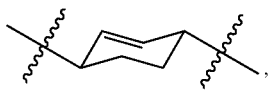 [SMILES: *C1C=CC(*)CC1]

are non-limiting examples of alkenediyl groups. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The groups, —CH=CHF, —CH=CHCl and —CH=CHBr, are non-limiting examples of substituted alkenyl groups. An "alkene" refers to the compound H—R, wherein R is alkenyl.

The term "alkynyl" when used without the "substituted" modifier refers to an monovalent unsaturated aliphatic group with a carbon atom as the point of attachment, a linear or branched, cyclo, cyclic or acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH$_3$, and —CH$_2$C≡CCH$_3$, are non-limiting examples of alkynyl groups. When alkynyl is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. An "alkyne" refers to the compound H—R, wherein R is alkynyl.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl group (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and the monovalent group derived from biphenyl. The term "arenediyl" when used without the "substituted" modifier refers to a divalent aromatic group, with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl group (carbon number limitation permitting) attached to the first aromatic ring or any additional aromatic ring present. If more than one ring is present, the rings may be fused or unfused. Non-limiting examples of arenediyl groups include:

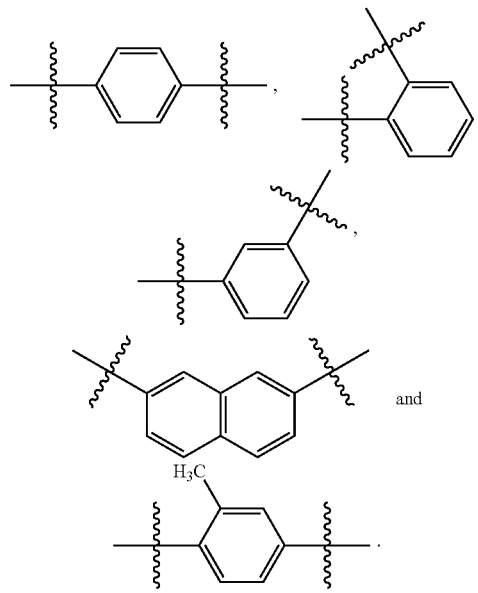

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. An "arene" refers to the compound H—R, wherein R is aryl.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term is used with the "substituted" modifier one or more hydrogen atom from the alkanediyl and/or the aryl has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. Non-limiting examples of substituted aralkyls are: β-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroaryl groups include furanyl, imidazolyl, indolyl, indazolyl (Im), isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroarenediyl groups include:

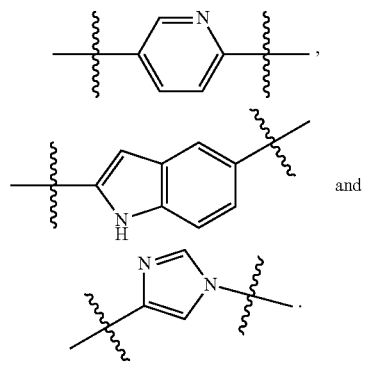

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. As used herein, the term does not preclude the presence of one or more alkyl groups (carbon number limitation permitting) attached to the ring or ring system. If more than one ring is present, the rings may be fused or unfused. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, and pyranyl. When the term "heterocycloalkyl" used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The term "acyl" when used without the "substituted" modifier refers to the group —C(O)R, in which R is a hydrogen, alkyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. When either of these terms are used with the "substituted" modifier one or more hydrogen atom (including the hydrogen atom directly attached the carbonyl or thiocarbonyl group) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples of alkoxy groups include: —OCH$_3$ (methoxy), —OCH$_2$CH$_3$ (ethoxy), —OCH$_2$CH$_2$CH$_3$, —OCH(CH$_3$)$_2$ (isopropoxy), —OCH(CH$_2$)$_2$, —O-cyclopentyl, and —O-cyclohexyl. The terms "alkenyloxy", "alkynyloxy", "aryloxy", "aralkoxy", "heteroaryloxy", and "acyloxy", when used without the "substituted" modifier, refers to groups, defined as —OR, in which R is alkenyl, alkynyl, aryl, aralkyl, heteroaryl, and acyl, respectively. The term "alkoxydiyl" refers to the divalent group —O-alkanediyl-, —O-alkanediyl-O—, or -alkanediyl-O-alkanediyl-. The term "alkylthio" and "acylthio" when used without the "substituted" modifier refers to the group —SR, in which R is an alkyl and acyl, respectively. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The term "alcohol" corresponds to an alkane, as defined above, wherein at least one of the hydrogen atoms has been replaced with a hydroxy group.

The term "alkylamino" when used without the "substituted" modifier refers to the group —NHR, in which R is an alkyl, as that term is defined above. Non-limiting examples of alkylamino groups include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The terms "alkoxyamino", "alkenylamino", "alkynylamino", "arylamino", "aralkylamino", "heteroarylamino", and "alkylsulfonylamino" when used without the "substituted" modifier, refers to groups, defined as —NHR, in which R is alkoxy, alkenyl, alkynyl, aryl, aralkyl, heteroaryl, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. The term "alkylaminodiyl" refers to the divalent group —NH-alkanediyl-, —NH-alkanediyl-NH—, or -alkanediyl-NH-alkanediyl-. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The groups —NHC(O)OCH$_3$ and —NHC(O)NHCH$_3$ are non-limiting examples of substituted amido groups.

The terms "alkylsulfonyl" and "alkylsulfinyl" when used without the "substituted" modifier refers to the groups —S(O)$_2$R and —S(O)R, respectively, in which R is an alkyl, as that term is defined above. The terms "alkenylsulfonyl", "alkynylsulfonyl", "arylsulfonyl", "aralkylsulfonyl", and "heteroarylsulfonyl", are defined in an analogous manner. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

As used herein, a "chiral auxiliary" refers to a removable chiral group that is capable of influencing the stereoselectivity of a reaction. Persons of skill in the art are familiar with such compounds, and many are commercially available.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "IC$_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiary-butylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002).

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexyl-sulfamates, quinates, esters of amino acids, and the like. Similarly, a compound comprising an amine group may be administered as an amide that is converted by hydrolysis in vivo to the amine compound.

The term "saturated" when referring to an atom means that the atom is connected to other atoms only by means of single bonds.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed 2n, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diasteromers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Effective amount," "Therapeutically effective amount" or "pharmaceutically effective amount" means that amount which, when administered to a subject or patient for treating a disease, is sufficient to effect such treatment for the disease.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease. In some embodiments, treatment of a patient afflicted with one of the pathological conditions described herein comprises administering to such a patient an amount of compound described herein which is therapeutically effective in controlling the condition or in prolonging the survivability of the patient beyond that expected in the absence of such treatment. As used herein, the term "inhibition" of the condition also refers to slowing, interrupting, arresting or stopping the condition and does not necessarily indicate a total elimination of the condition. It is believed that prolonging the survivability of a patient, beyond being a significant advantageous effect in and of itself, also indicates that the condition is beneficially controlled to some extent.

Other abbreviations used herein are as follows: $^1$H-NMR is proton nuclear magnetic resonance, AcOH is acetic acid, Ar is argon, $CH_3CN$ is acetonitrile, CHN analysis is carbon/hydrogen/nitrogen elemental analysis, CHNCl analysis is carbon/hydrogen/nitrogen/chlorine elemental analysis, CHNS analysis is carbon/hydrogen/nitrogen/sulfur elemental analysis, DI water is deionized water, DIC is diisopropyl carbodiimide, DMA is N,N-dimethylacetamide, DMAP is 4-(N,N-dimethylamino)pyridine, DMF is N,N-dimethylformamide, EDCl is 1-(β-dimethylaminopropyl)-3-ethylcarbodiimide hydrochloride, EtOAc is ethyl acetate, EtOH is ethanol, FAB MS is fast atom bombardment mass spectroscopy, g is gram(s), HOBT is 1-hydroxybenzotriazole hydrate, HPLC is high performance liquid chromatography, IBCF is isobutylchloroformate, KSCN is potassium thiocyanate, L is liter, LiOH is lithium hydroxide, MEM is methoxyethoxymethyl, MEMCl is methoxyethoxymethyl chloride, MeOH is methanol, mg is milligram, $MgSO_4$ is magnesium sulfate, ml is milliliter, mL is milliliter, MS is mass spectroscopy, MTBE is methyl tert-butyl ether, $N_2$ is nitrogen, $NaHCO_3$ is sodium bicarbonate, NaOH is sodium hydroxide, $Na_2SO_4$ is sodium sulfate, NMM is N-methylmorpholine, NMP is N-methyl pyrrolidinone, NMR is nuclear magnetic resonance, $P_2O_5$ is phosphorous pentoxide, PTSA is para-toluenesulfonic acid, RPHPLC is reverse phase high performance liquid chromatography, RT is room temperature, TFA is trifluoroacetic acid, THF is tetrahydrofuran, TMS is trimethylsilyl, and Δ is heating the reaction mixture.

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

F. THERAPEUTIC METHODS

1. Pharmaceutical Formulations

In particular embodiments, where clinical application of an active ingredient is undertaken, it will be necessary to prepare a pharmaceutical composition appropriate for the intended application. Generally, this will entail preparing a pharmaceutical composition that is essentially free of pyrogens, as well as any other impurities that could be harmful to humans or animals. One also will generally desire to employ appropriate buffers to render the complex stable and allow for uptake by target cells.

Aqueous compositions comprise an effective amount of the active ingredient, as discussed above, further dispersed in pharmaceutically acceptable carrier or aqueous medium. Such compositions also are referred to as inocula. The phrases "pharmaceutically or pharmacologically acceptable" refer to compositions that do not produce an adverse, allergic or other untoward reaction when administered to an animal, or a human, as appropriate.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

Solutions of therapeutic compositions can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms.

The therapeutic compositions are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well-known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, a controlled release patch, salve or spray.

An effective amount of the therapeutic composition is determined based on the intended goal. The term "unit dose" or "dosage" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the protection desired.

Precise amounts of the therapeutic composition also depend on the judgment of the practitioner and are peculiar to each individual. Factors affecting dose include physical and clinical state of the patient, the route of administration, the intended goal of treatment and the potency, stability and toxicity of the particular therapeutic substance.

2. Routes of Administration

Formulations can be suitable for oral administration. However, the therapeutic compositions may be administered via any common route so long as the target tissue is available via that route. This includes nasal, buccal, rectal, vaginal or topical, intradermal subcutaneous, intramuscular, intraperitoneal or intravenous injection. As such, compositions would formulated pharmaceutically in route-acceptable compositions that include physiologically acceptable carriers, buffers or other excipients.

As with dosing amounts, the timing of delivery (including intervals and total number of doses) depends on the judgment of the practitioner and are peculiar to each individual. Factors affecting dose include physical and clinical state of the patient, the route of administration, the intended goal of treatment and the potency, stability and toxicity of the particular therapeutic substance.

3. Combination Therapy

In many clinical situations, it is advisable to use a combination of distinct therapies. Thus, it is envisioned that, in addition to the therapies described above, one would also wish to provide to the patient more "standard" pharmaceutical HBV therapies. Examples of standard therapies are described above. Combinations may be achieved by administering a single composition or pharmacological formulation that includes both agents, or with two distinct compositions or formulations, at the same time, wherein one composition includes the agents described herein and the other includes the standard therapy. Alternatively, standard therapy may precede or follow the present agent treatment by intervals ranging from minutes to weeks. In embodiments where the treatments are applied separately, one would generally ensure that a significant period of time did not expire between the time of each delivery, such that the agents would still be able to exert an advantageously combined effect on the subject. In such instances, it is contemplated that one would administer both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either (a) the agent described herein, or (b) the standard therapy will be desired. Various combinations may be employed, where the compound is "A" and the standard therapy is "B", as exemplified below:

A/B/A B/A/B B/B/A A/A/B B/A/A A/B/B B/B/B/A B/B/ A/B A/A/B/B A/B/A/B A/B/B/A B/B/A/A B/A/B/A B/A/A/B B/B/B/A A/A/A/B B/A/A/A A/B/A/A A/A/ B/A A/B/B/B B/A/B/B B/B/A/B

Other combinations are contemplated as well. Drugs suitable for such combinations are described above and include, but are not limited to, Intron A® (Interferon Alpha), Pegasys® (Pegylated Interferon), Epivir HBV® (Lamivudine), Hepsera® (Adefovir), Baraclude® (Entecavir), Tyzeka® (Telbivudine), and Viread® (Tenofovir).

G. EXAMPLES

The following examples are included to further illustrate various aspects of the disclosure. It should be appreciated by those of skill in the art that the techniques disclosed in the examples which follow represent techniques and/or compositions discovered by the inventor to function well in the practice of the methods herein, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

1. Materials and Methods

Plasmids and Viral Strains Employed.

pCMV-HBV-LE-(CMV-HBV) is an HBV over-length genomic expression vector containing 1.2 copies of the HBV(adw2) genome (Genbank X02763.1) downstream of the CMV promoter cloned into pBS (Promega). Surface protein expression from this vector is ablated by mutating the preS and S open reading frames. pCMV-HBV(genotype D) is an analogous HBV genomic expression construct and was a gift from Dr. Shuping Tong (Brown University). For bacterial expression, codon-optimized cDNA sequences for HRHPL (genotypes A, B, C, D, and H), and noncodon-optimized sequences for HHC1 and HHC2 were cloned by gene synthesis (Genscript) between the NcoI and EcoRI sites into pTrcHis2B (Invitrogen) with a C-terminal hexahistidine tag. HRHPL contains HBV genotype D (Genbank V01460) polymerase residues 684-845. HHC1 is an HRHPL derivative in which HBV polymerase residues 800-808 were replaced with HIV residues corresponding to the RNAseH helix D (VNQIIEQLIVK; SEQ ID NO:6). HHC2 is an HRHPL derivative in which HBV polymerase residues 800-845 were replaced with HIV residues corresponding to the RNAseH helix D to the C-terminus (VNQIIEQLIVK-KEKVYLAWVPAHKGIGGNEQVDKLVSAGIRKVL; SEQ ID NO:7). The human RNAseH1 gene (NP_002927.2) was cloned with an N-terminal hexahistidine-tag between the BamHI and XhoI sites of pRsetB (Invitrogen) by gene synthesis.

RNAseH Expression and Enrichment.

HRHPL, HHC1, HHC2, and human RNAseH1 were expressed in E. coli B121 codon+ cells (Invitrogen). Saturated overnight bacterial cultures were diluted 4-fold into 100 ml fresh medium and protein expression was induced with 0.5 mM IPTG at 30° C. for six hours. The cells were lysed by sonication in lysis buffer [50 mM HEPES pH 8.0, 800 mM NaCl, 0.1% NP40, 27.5% glycerol, 2 mM DTT 20 mM imidazole, and protease inhibitor cocktail (Sigma)]. RNAseH proteins were enriched by nickel-agarose affinity chromatography, eluted with 350 mM imidazole, dialyzed into 50 mM HEPES pH 7.3, 300 mM NaCl, 20% glycerol, and 5 mM DTT, and stored in liquid nitrogen.

In Vitro RNAseH Assays.

Figure 5:
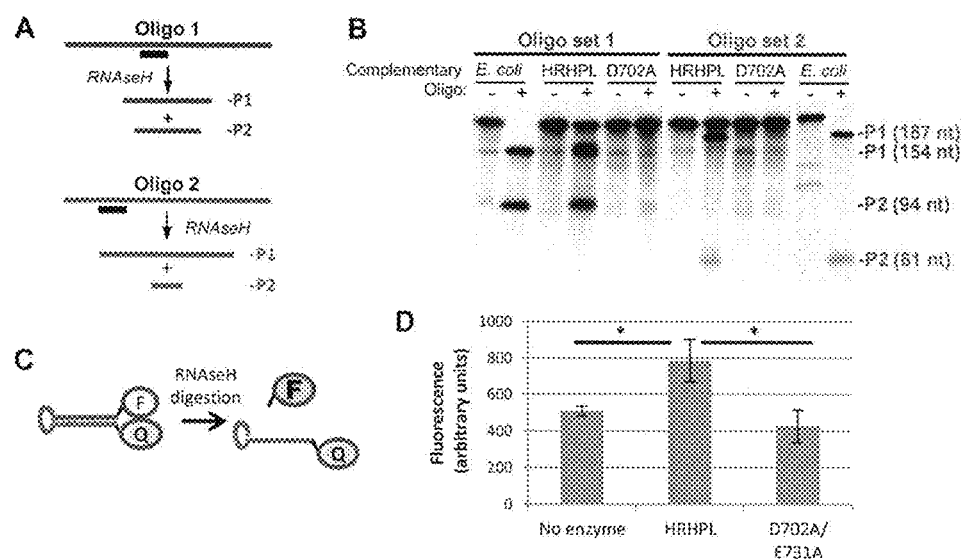
FIGS. 5A-D. Recombinant HBV RNAseH is enzymatically active.

For the oligonucleotide-directed RNAseH cleavage assay (Gong et al., 2001), 6 µl protein extract (typical protein concentration 2.8 mg/ml) was mixed with 0.5 µg internally $^{32}$P-labeled DRF+ RNA (nucleotides 2401-2605 of the duck HBV genome plus 60 nucleotides of flanking sequences from pBluescript) and 3 µg oligonucleotide D2507- or its corresponding negative control D2526+ on ice in 20 µl under the conditions in Table 1. Some reactions in FIG. 5 employed oligonucleotide D2543M-Sal or its D2453+ negative control as indicated. The reactions were incubated at 42° C. for 90 min. and terminated by addition of Laemmli protein loading buffer and boiling. The samples were resolved by 12% SDS-PAGE, the gels were stained with Coomassie blue to monitor protein loading, and labeled RNA was detected by autoradiography. Candidate inhibitors were dissolved in DMSO and added at the indicated concentrations during assembly of the reactions. Control reactions lacking the compounds contained DMSO as a vehicle control. The RNAseH autoradiograms were scanned and quantified with ImageJ. The oligonucleotides were: D2526+ (CCACATAGGCTATGTGGAAC; SEQ ID NO:8), D2507- (GTTCCACATAGCCTATGTGG; SEQ ID NO:9), D2453+ (CCGCCTGATTGGACGGCTTTTCC; SEQ ID NO:10), and D2543M-Sal (GCAACTGTGTCGACAGCAGCTC-CGAAGGAGA; SEQ ID NO:11).

For the fluorescent RNAseH assay, the DRF+ RNA and DNA oligonucleotides were omitted from the RNAseH reactions and replaced with 20 µM of the quenched fluorescent chimeric RNA:DNA oligonucleotide RHF1; the reaction conditions were identical to the oligonucleotide-directed reactions except that the NaCl concentration was reduced to 130 mM. The reactions were incubated in the dark at 42° C. for 90 min. prior to termination by addition EDTA to 10 mM and detection of fluorescence at 520 nM on Synergy 4 plate reader (Biotec, Inc.). The sequence of the RHF1 substrate (IDT, Inc.) was: 5'-56-FAM/rCrCrAr-CrArUrArGrGrCrUrArUrGrUrGrGrArArCTTTTGTTC-CACATAGCCTATG TGG/3IBkFQ/-3' (5'-56-FAM/SEQ ID NO:12/3IBkFQ/-3'). The RNA:DNA heteroduplex in the RHF1 substrate was the same as the heteroduplex formed by oligo D2507- annealed to DRF+.

Cell-Based HBV Replication Inhibition Assays.

Huh7 cells were maintained in Dulbecco's modified Eagle's medium with 10% fetal bovine serum at 37° C. in 5% CO$_2$. Cells were seeded into 60 mm dishes and transfected at 70% confluency with 2.6 µg of plasmids using TransIT-LT1 (Mirus, Inc.). Test compounds were added the morning following transfection at 10 or 50 µM, and fresh medium containing the compounds was provided every 1-2 days. Four or five days post-transfection HBV cores were isolated by lysis of the cells in 10 mM Tris pH 7.5, 1 mM EDTA, 0.25% NP40, 50 mM NaCl, and 8% sucrose followed by sedimentation through a 30% sucrose cushion as described (Travis, et al., 1998). Viral DNAs were isolated from cytoplasmic core particle preparations by proteinase K digestion followed by phenol/chloroform extraction as described (Gong et al., 2001). Duplicate aliquots of the nucleic acids were treated with 2 U E. coli DNAse-free RNAseH (Invitrogen) at 37° C. for 30 min. or were mock treated. The nucleic acid samples were resolved by electrophoresis on 1.2% agarose gels and detected by Southern blotting with $^{32}$P-labeled HBV DNA as a probe.

2. Results

Confirmation of Key HBV RNAseH Active Site Residues.

Figure 2A:
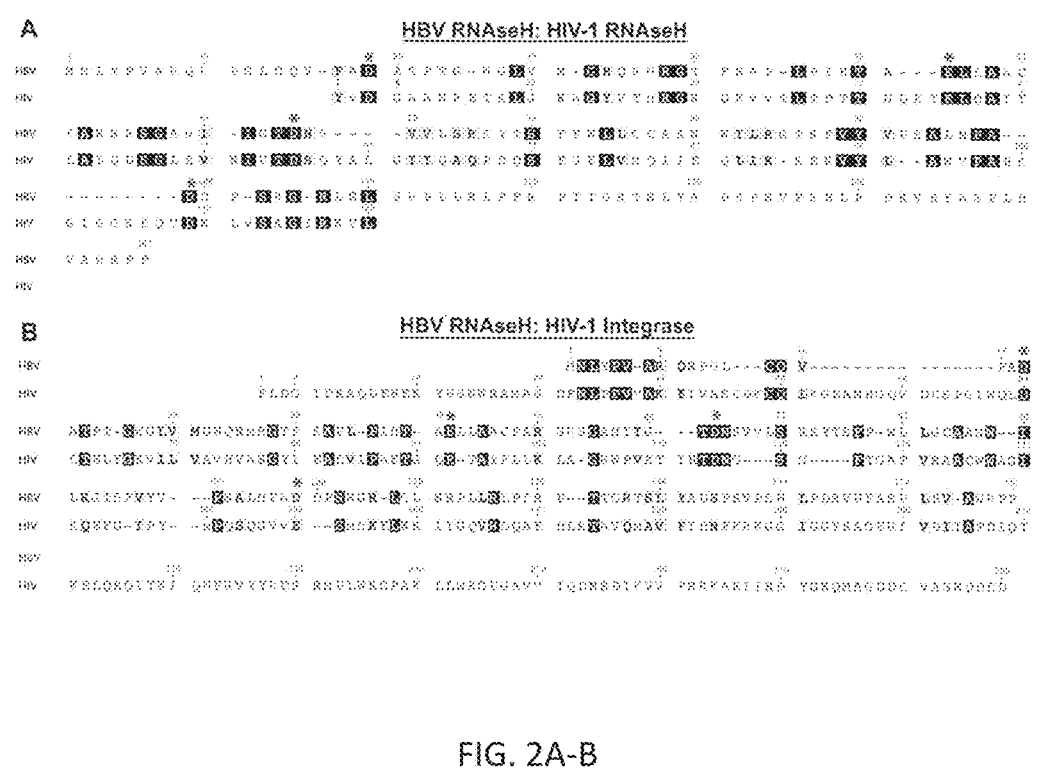
Figure 3:
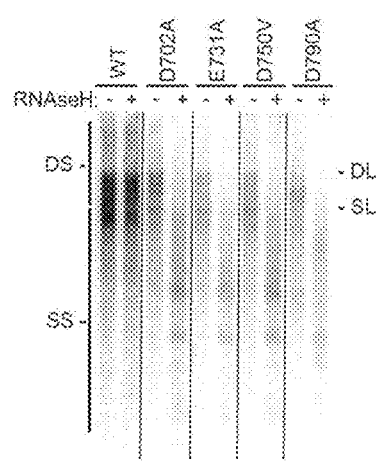
FIG. 3. Identification of the DEDD motif in the HBV RNAseH active site. Wild-type and mutant genotype A HBV genomic expression vectors were transfected into cells, intracellular capsids were isolated five days later, and viral nucleic acids were purified from the capsids. The nucleic acids were divided into two aliquots; one aliquot was treated with DNAse-free E. coli RNAseH to destroy RNA:DNA heteroduplexes and the other was mock treated. The nucleic acids were resolved by agarose electrophoresis and HBV DNAs were detected by Southern analysis. The signature of an RNAseH-deficient genome is production of RNA:DNA heteroduplexes in which the DNA migrates as double-stranded species without treatment with exogenous RNAseH treatment but as singe-stranded species following degradation of the RNA. The positions of the duplex linear (DL) and full-length single-stranded linear (SL) HBV DNA markers are shown. DS indicates the spectrum of double-stranded nucleic acids produced by reverse transcription, and SS indicates the spectrum of single-stranded nucleic acids.

The HBV DEDD residues have been implicated to be D702, E731, D750, and D790 (numbering for HBV strain adw2) by sequence alignments against other RNAseHs (FIGS. 2A-B), but only D750 has been experimentally confirmed to be essential for RNAseH activity (Gerelsaikhan, 1996 #2057). Therefore, the inventor introduced D702A, E731A, D750V, and D790A mutations into the predicted DEDD motif residue in an HBV genomic expression vector. The wild-type and mutant genomes were transfected into Huh7 cells, five days later intracellular viral capsids were purified, and then HBV DNAs within the particles were detected by Southern analysis. All four mutants supported DNA synthesis and hence could be analyzed by this approach. The signature of an RNAseH-deficient enzyme is production of RNA:DNA heteroduplexes that migrate like double-stranded DNAs on native gels but as faster-migrating single-stranded DNAs of multiple lengths following digestion of the capsid-derived nucleic acids with exogenous RNAseH. DNAs produced by the wild-type genome were unaffected by treatment with RNAseH prior to electrophoresis (FIG. 3). Mutating each of the four of the predicted RNAseH DEDD residues blocked production of the slowest-migrating double-stranded forms (mature relaxed-circular DNAs) and led to accumulation of smaller forms that migrated similarly to other double-stranded DNAs (primarily less-mature relaxed-circular DNAs) produced by the wild-type genome. Treatment of the nucleic acids from the mutant genomes with exogenous RNAseH collapsed the double-stranded forms to single-stranded forms (FIG. 3). Therefore, all four mutants were RNAseH deficient.

Production of Enzymatically Active Recombinant HBV RNAseH.

Figure 4:
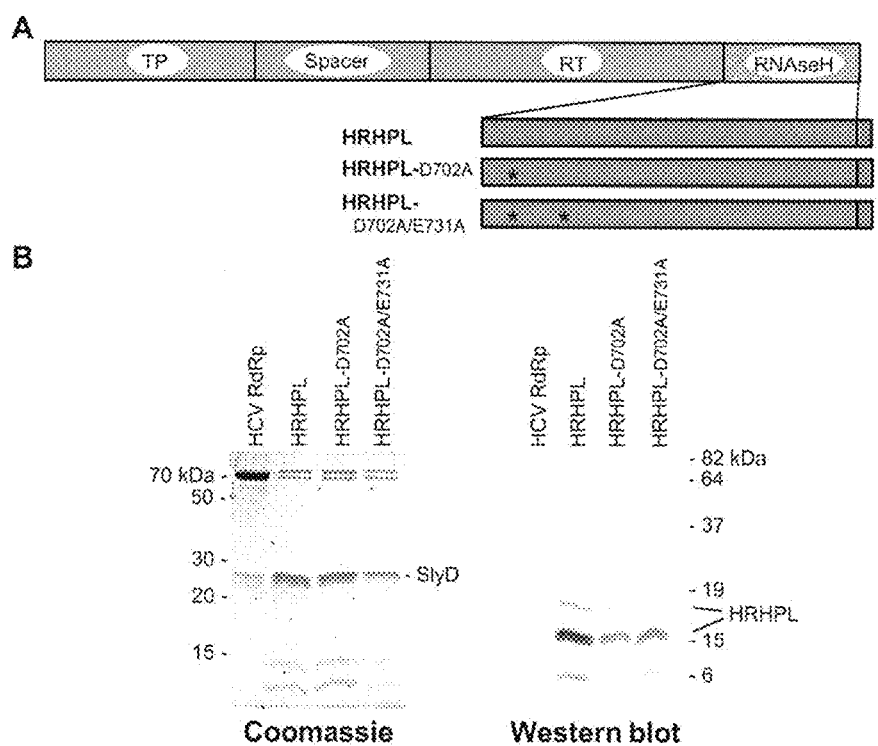
FIGS. 4A-B. Recombinant HBV RNAseH proteins.

The inventors expressed HBV RNAseH sequences from the HBV isolate employed by (Potenza et al., 2007) in *E. coli* as a carboxy-terminally hexahistidine tagged recombinant protein, but they moved the amino terminus nine residues upstream to a site he felt was more probable to yield soluble protein (HRHPL; FIG. 4A). As a negative control, the inventors mutated two of the DEDD active site residues (D702A and E731A). These constructs were expressed in *E. coli*, soluble lysates were prepared, and the lysates were subjected to nickel-affinity chromatography.

Five proteins of approximately 80, 70, 26, 14, and 11 kDa detectable by Coomassie staining were recovered following chromatography, none of which correlated with the predicted mass of 18.9 kDa for HRHPL (FIG. 4B). Mass spectrometry identified the dominant 26 kDa band as the *E. coli* prolyl isomerase SlyD. Concentrating the samples seven-fold did not increase the RNAseH to levels detectable by Coomassie staining. However, western analysis with the anti-HBV RNAseH domain antibody 9F9 (Zu Putlitz et al., 1999) Santa Cruz Biotechnology revealed a small amount of recombinant HBV RNAseH that migrated close to its predicted mass plus a larger amount of the protein that migrated as a doublet near 15 kDa (FIG. 4B). The doublet is presumably due to proteolysis near the protein's N-terminus because the antibody epitope and hexahistidine tag are at the C-terminus. The sizes of the truncation products imply that they were cleaved near HRHPL residue 36, which would remove the essential D702 carboxylate (HRHPL residue 20) and inactivate the protein. These experiments indicate one could express and enrich small but readily detectable amounts of soluble recombinant HBV RNAseH.

The inventors tested activity of the recombinant HBV RNAseHs in a DNA oligonucleotide-directed RNA cleavage assay. In this assay, a DNA oligonucleotide is annealed to a uniformly-labeled RNA to create an RNA:DNA heteroduplex. Cleavage of the RNA in the heteroduplex yields two RNA fragments of predictable size that are resolved by electrophoresis and detected by autoradiography (FIG. 5A). The inventor employed the 264 nt RNA (DRF+) used in previous RNAseH assays (Gong et al., 2001) in combination with two DNA oligonucleotide pairs. One oligonucleotide in each pair was the correct polarity to anneal to the DRF+ RNA and the other was its inverse complement as a negative control.

Oligonucleotide-directed RNAseH assays were conducted with wild-type HRHPL enzyme and the RNAseH-deficient D702A mutant. The RNA was not cleaved when the non-complementary oligonucleotides were employed in the reactions (FIG. 5B), demonstrating that the enzyme preparations did not contain non-specific RNAse activity. Use of complementary oligonucleotide #1 (D2507−) led to complete cleavage of the DRF+ RNA by *E. coli* RNAseH into products of 154 and 94 nt, and to partial cleavage of the RNA at the same site by wild-type HRHPL (FIG. 5B). The large majority of this RNAseH activity was due to the HBV enzyme because mutating DEDD residues D702A and/or E731A sharply reduced cleavage of the RNA. Note that although the relative yield of full-length mutant RNAseH is less than the wild-type enzyme in FIGS. 4A-B, in other preparations the amount of mutant RNAseH exceeded the amount of wild-type enzyme (e.g., FIGS. 6A-C). In all cases, the enzymatic activity associated with the mutant RNAseH preparations was far lower than in the wild-type preparations. The residual cleavage products in reactions with the mutant enzymes appear to be non-specific breakdown products from the RNA substrate and/or digestion products from trace contamination with bacterial RNAseH. The RNA products shifted sizes as expected when complementary oligonucleotide #2 (D2543M-Sal, which anneals 33 nt closer to the 3' end of the RNA) was employed in the RNAseH assays (FIG. 5B): the larger fragment became larger (187 nt) and the smaller fragment became smaller (61 nt). These data demonstrate that the RNAse activity in HRHP is specific for RNA annealed to the DNA oligonucleotides, and hence confirm that it is an RNAseH activity.

Finally, the inventors synthesized a quenched fluorescent RNA:DNA chimeric hairpin oligonucleotide substrate (RHF1) to confirm RNAseH activity with a different assay. RHF1 has fluorescein at its 5' end, 20 nt of RNA, a 4 nt DNA hairpin, 20 nt of DNA complementary to the RNA sequence, and an Iowa Black FQ quencher at the 3' terminus. The hairpin brings the fluorescein and quencher into close proximity, and digesting the RNA frees the fluorescein and increases its fluorescence (FIG. 5C). RHF1 was terminally digested with *E. coli* RNAseH, the reactions were terminated with 10 mM EDTA and fluorescence was measured. This digestion amplified the fluorescence of RHF1 22-fold, for a 95% quenching efficiency. RHF1 was then employed in an RNAseH assay with buffer alone, wild-type HBV RNAseH (HRHPL), and HRHPL-D702A/E731A. RNAseH activity for HRHPL was about 2-fold higher than the no-enzyme control, and mutating the RNAseH active site eliminated this activity (FIG. 5D). This weak signal (7% of the maximal signal strength in this assay) appears to be due to poor binding between the small substrate and the RNAseH in the relatively high ionic strength of the reactions because detection of RNAseH activity required reducing the NaCl concentration from 190 to 130 mM.

Together, these data indicate that one can readily detect HBV RNAseH activity in the enriched bacterial extracts despite the fact that the HBV RNAseH is a minor component of the mixture.

Optimization of Reaction Conditions.

The optimal enzymatic conditions for the HRHPL HBV RNAseH were determined by systematically varying the reaction components in the oligonucleotide-directed RNAseH assay (Table 1). Recombinant HBV RNAseH was active over a wide range of pH values but was most active near 8.0. Its activity maximum was at 190 mM NaCl and it lost specificity for RNA:DNA heteroduplexes below ~100 mM NaCl. The RNAseH required ~5 mM $Mg^{++}$ for maximal activity; increasing $Mg^{++}$ beyond ~7 mM suppressed RNAseH activity, and inclusion of $Mn^{++}$ in the reactions led to nonspecific degradation of the RNA. The enzyme became inactive at low reductant concentrations, but it could tolerate up to 2% DMSO, it was stable upon storage in liquid nitrogen, and only marginal loss of activity was observed following five sequential freeze-thaw cycles.

Recombinant RNAseH Enzymes from Other HBV Genotypes.

Figure 6:
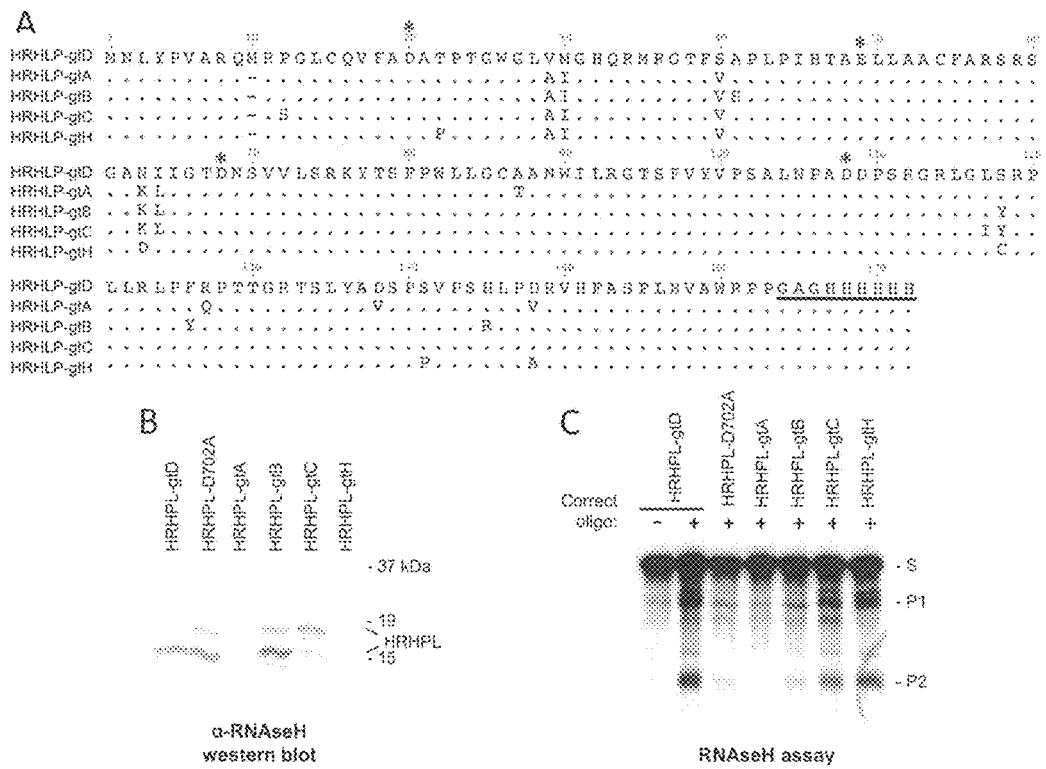
FIGS. 6A-C. Recombinant RNAseHs from HBV genotypes A, B, C, D, and H.

HBV has eight genotypes (A-H, plus provisional identification of genotypes I and J) that differ by >8% at the sequence level (Kramvis et al., 2005 and Kurbanov et al., 2010). The inventors cloned HBV RNAseH domains for genotype A, B, C, and H isolates using the same structure as the HRHPL construct (genotype D) to determine whether HBV's genetic diversity leads to variable sensitivity to inhibitors that must be taken into account during drug development (FIG. 6A). The protein profile detectable by Coomassie staining following expression and nickel-affinity enrichment for all additional constructs was the same as for HRHPL. Western blotting with antibody 9F9 detected the genotype B, C, and D RNAseHs, with the genotype C enzyme appearing primarily as the full-length protein (FIG. 6B). The failure to detect the genotype A and H RNAseHs was due either to lack of accumulation of the proteins or to amino acid variations in the C-terminus of the protein where the antibody epitope is located (Zu Putlitz et al., 1999).

The genotype A, B, C, D, and H RNAseH extracts were assessed with the oligonucleotide-directed RNAseH assay (FIG. 6C). The genotype A and B enzymes were inactive, genotype C RNAseH was active, and activity of the genotype H enzyme was similar to that of the genotype D RNAseH. The [NaCl]—, [$Mg^{++}$]-, temperature-, and pH-profiles of the genotype H RNAseH were very similar to those of the genotype D enzyme (data not shown).

Therefore, the inventors can express recombinant HBV genotype B, C, D, and H RNAseH proteins that are detectable by enzymatic assays and/or western blotting, but only the genotype C, D and H proteins are consistently active.

Production of Active HBV:HIV Chimeric RNAseHs.

Figure 7:
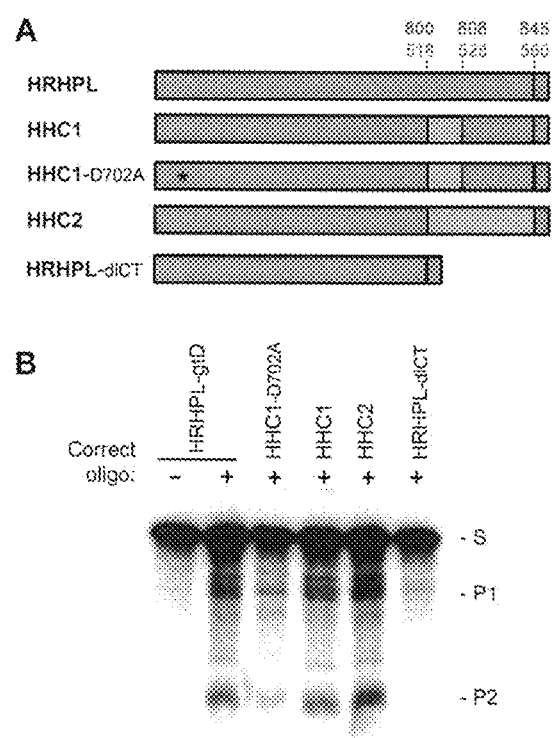
FIGS. 7A-B. Chimeric HBV:HIV RNAseH enzymes.

The C-termini of the HBV and other RNAseH sequences (including HIV) do not align well without extensive manual intervention in the alignments, implying that the HBV RNAseH may fold in a non-canonical manner. The inventors addressed this issue by creating two chimeric enzymes in which HBV sequences near the 3' end of the RNAseH gene were replaced by HIV-1 sequences (FIG. 7A). The hypothesis was that if HIV RNAseH sequences could substitute for the HBV sequences despite a lack of primary sequence similarity, then the enzymes would probably fold in a similar manner. The chimeric HHC1 protein contains HIV α helix D substituting for sequences in HRHPL as identified by secondary structure-guided alignments. HHC2 contains HIV sequences from helix D to the C-terminus of the HIV RNAseH sequences (α-helix D, β-sheet 5, and α-helix E) in place of the HBV RNAseH C-terminal sequences. The inventor also deleted HBV sequences from helix D to the C-terminus in the construct HRHPL-dlCT to determine whether the HBV sequences that were substituted by the HIV sequences in HHC2 were essential for HBV RNAseH function. As with the wild-type HBV RNAseHs, the chimeric RNAseH proteins were not detectable by Coomassie staining following nickel-affinity enrichment (data not shown).

HHC1 and HHC2 were active in the oligonucleotide-directed RNA cleavage assay (FIG. 7B). Mutating the HBV DEDD residue D702 to A eliminated the large majority of the activity in the enriched protein extracts, confirming that most of the RNAseH activity was due to the recombinant enzyme. The enzymatic profiles of both chimeric proteins were similar to those of the wild-type enzymes, but the chimeric enzymes had pH optima closer to 7.5 than 8.0, and that they were less stable upon storage. The HRHPL-dlCT extracts were inactive in the RNAseH assays. Therefore, the region of the HBV RNAseH that was replaced with HIV sequences was needed for RNAseH activity and/or for protein stability.

Identification of Anti-HBV RNAseH Compounds.

Figure 8:
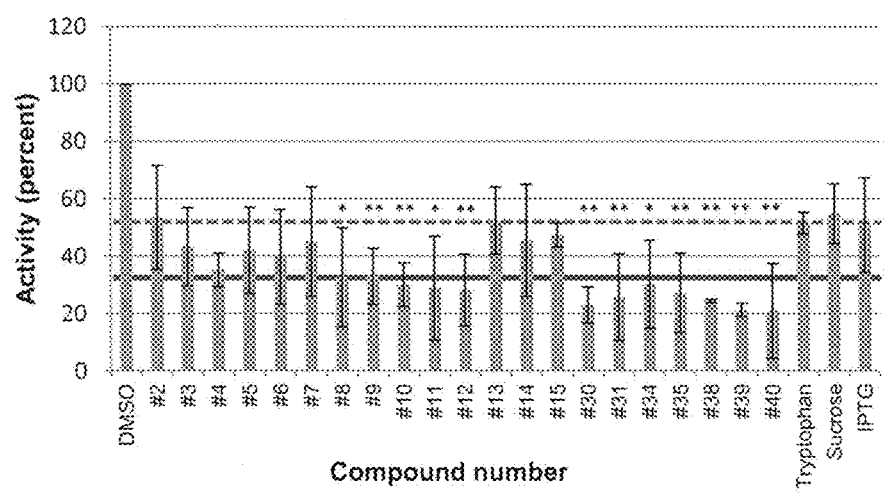
FIG. 8. Inhibition of the HBV RNAseH by candidate compounds selected for their similarity to antagonists of the HIV RNAseH and integrase. Candidate inhibitors (compounds #2-40) and irrelevant compounds (tryptophan, sucrose, and IPTG) were included at 10 µM in a standard oligonucleotide-directed RNAseH assay employing wild-type HBV RNAseH (HRHPL). DMSO, vehicle control. Error bars are ±one standard deviation from three to seven replicates. The dashed red line indicates the mean residual activity in the irrelevant control reactions (52%) and the solid red line is two standard deviations of the irrelevant control assays below their mean (33%). Compounds that inhibited the RNAseH to 33% or below were considered to be positive ("+" in Table 2). *, P<0.05 by T-test against the pooled data for the irrelevant controls; **, P<0.01.
Figure 9:
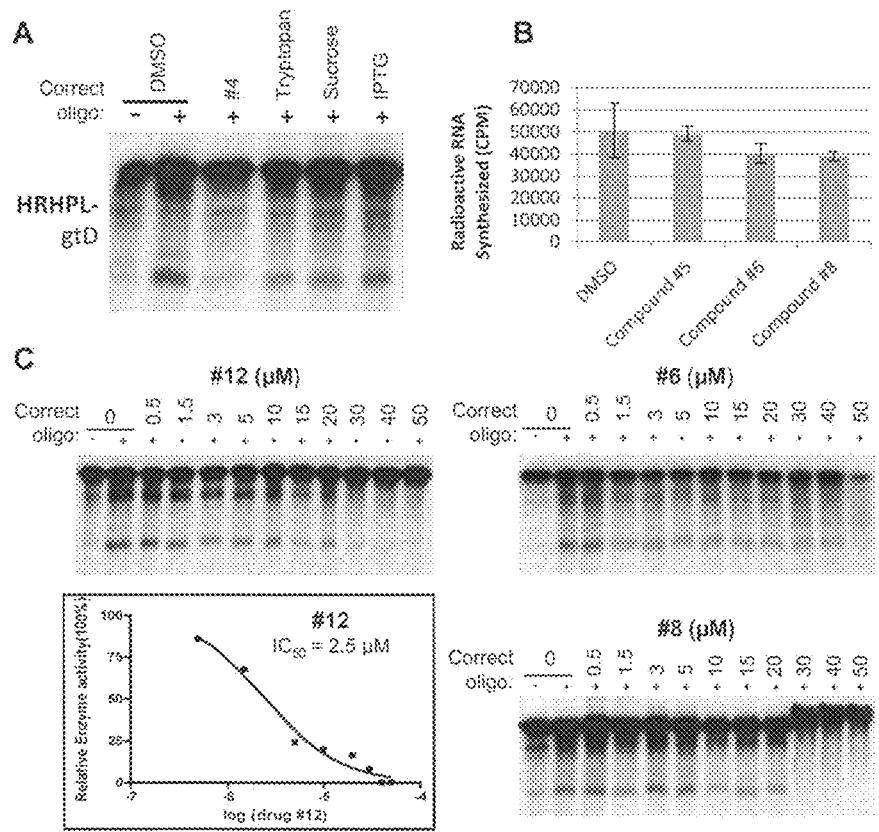
FIGS. 9A-C. Specificity of anti-HBV RNAseH compounds.
Figure 14:
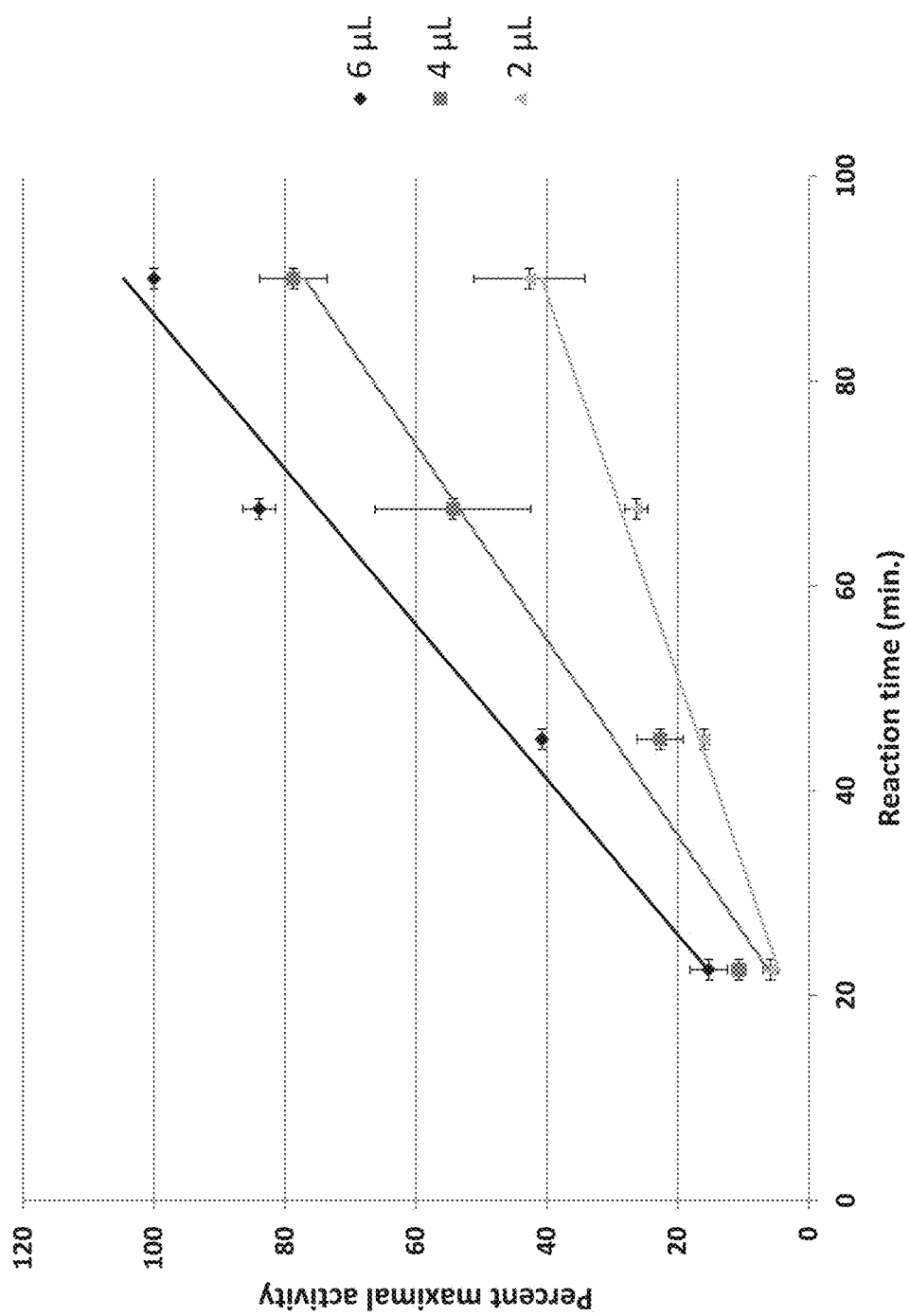
FIG. 14. Concentration and Time Dependence of Oligonucleotide-Directed RNAseH Assays. Standard oligonucleotide-directed RNAseH assays containing 2, 4, or 6 μL RNAseH extract were incubated for 20 to 90 minutes and fit to linear relationships based upon both concentration and time ($R^2 > 0.97$ for each fit). Error bars are ±1 standard deviation from three experiments.

The inventors hypothesized that the HBV RNAseH may be inhibited by antagonists of the HIV RNAseH based on the similarity of the reactions they catalyze. He identified 10 compounds known to inhibit the HIV RNAseH or that were predicted by chemical structure-activity relationships to do so (Table 2 and FIG. 12). They further hypothesized that anti-HIV integrase compounds may inhibit the HBV RNAseH because the integrase and RNAseH are both members of the nucleotidyl transferase superfamily and because some anti-HIV RNAseH and integrase compounds can cross-inhibit their target enzymes (Klarmann et al., *AIDS Rev* 4: 183-194, 2002; Williams, et al., *BioorgMedChemLett* 20: 6754-6757, 2010; Billamboz et al., *JMedChem* 54: 1812-1824, 2011; Shaw-Reid, et al., *JBiolChem* 278: 2777-2780, 2003 and Billamboz, et al., *JMedChem* 51: 7717-7730, 2008). Consequently, they also obtained 11 compounds either known to inhibit the HIV integrase or predicted by chemical structure-activity relationships to do so (Table 2 and FIG. 12). The inventors first measured the effect of irrelevant compounds (tryptophan, sucrose, and IPTG) on the RNAseH assay. These compounds reduced RNAseH activity of HRHPL to 52±9% relative to the DMSO vehicle control (FIGS. 8 and 9A). This allowed the inventors to define the mean of the residual activity in the presence of the irrelevant compounds minus two standard deviations of the irrelevant controls as a threshold reduction of the RNAseH activity that must be exceeded before the inventor considered inhibition by the test compounds to be relevant. Using this threshold, 12 of the 21 compounds inhibited the HBV genotype D RNAseH at 10 μM (FIG. 8, Table 2, and Table 3). These 21 compounds were also screened against the HBV genotype H RNAseH and the chimeric HHC1 enzyme using the oligonucleotide-directed RNAseH assay. Compounds #12, 14, 34, 39, and 40 inhibited the HBV genotype H RNAseH at 10 μM. Furthermore, the oligonucleotide-directed RNAseH assay showed that the change in percent activity is linear at both time and enzyme concentrations of 2-6 μL RNAseH extract (FIG. 14). The inhibition profile against the chimeric RNAseH HHC1 was similar to that of the genotype D HBV RNAseH, but the compounds were usually less effective than against the wild-type enzyme. This is consistent with the HBV portion of HHC1 being from genotype D HRHPL.

The unexpectedly high frequency of inhibition of the genotype D enzyme led us to question the mechanism(s) by which it was inhibited by the compounds. The inventors addressed this in two manners. First, RNAseH inhibitors usually block the HIV enzyme by interfering with the divalent cations in the active site (Fuji et al., *JMedChem* 52: 1380-1387, 2009; Su et al., *JVirol* 84: 7625-7633, 2010; Chung, et al., *JMedChem* 54: 4462-4473, 2011; Billamboz et al., *JMedChem* 54: 1812-1824, 2011; Himmel et al., *Structure* 17: 1625-1635, 2009; Kirschberg et al., *JMedChem* 52: 5781-5784, 2009). Consequently, the inventor asked whether the compounds act non-specifically by chelating $Mg^{++}$. Isothermal calorimetry demonstrated that compounds #5, 6, and 8 did not bind $Mg^{++}$ in the absence of the protein extracts (data not shown). This is consistent with their inability to significantly inhibit poly-G synthesis by the Hepatitis C virus (HCV) RNA polymerase which is also active in 5 mM $Mg^{++}$ (Cao et al., 2011) (FIG. 9B). Second, the inventors titrated selected compounds from 50 to 0.5 μM to examine dose-responsiveness of inhibition (FIG. 9C). Compound #12 had a typical inhibition curve with an $IC_{50}$ of 2.5 μM in this experiment; similar smooth dose-response curves were observed for compounds #39 and 40 (data not shown). In contrast, inhibition by compound #6 plateaued at 20-30% between 3 and 40 μM but then increased to 75% at 50 μM. Compound #8 was ineffective below 5 μM, it inhibited the enzyme by 40-85% between 10 and 30 μM, and caused aberrant migration of the RNA at 40 and 50 μM. These data indicate that some compounds behaved as predicted from their mechanism of action against HIV, but that inhibition by other compounds may have been due to alternative effects, possibly including interaction with the RNA and/or aggregation of the enzyme.

Activity of HBV RNAseH Inhibitors Against Human RNAseH1.

Figure 10:
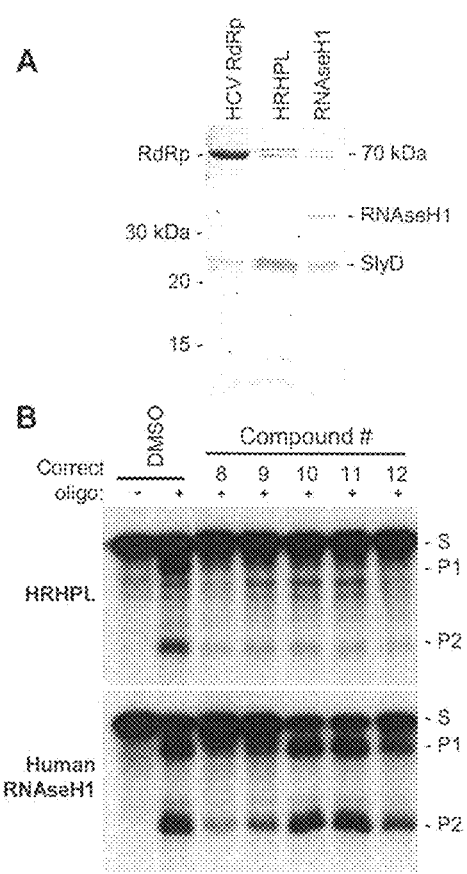
FIGS. 10A-B. Activity of HBV RNAseH inhibitors against human RNAseH1.

The most likely cause of cellular toxicity for anti-HBV RNAseH drugs would be inhibition of human RNAseH1 because it is responsible for about 80% of the RNAseH activity in human cells (Lima et al., 2001 and Lima et al., 2007). Therefore, the inventors cloned the human RNAseH1 with an N-terminal hexahistidine tag, expressed it in *E. coli*, and purified the protein by nickel affinity chromatography. The same spectrum of contaminating *E. coli* proteins as was observed for the other RNAseH preparations was detectable by Coomassie staining, but RNAseH1 could be detected at its predicted mass of 32 kDa (FIG. 10A). This enzyme was active in the oligonucleotide-directed and fluorescent RNAseH assays (FIG. 10B and data not shown). To determine how inhibition of human RNAseH1 compared to inhibition of the HBV RNAseH, the inventor titrated the RNAaseH1 enzyme to yield similar levels of activity as the HBV enzyme, and then the inventor directly compared the ability of compounds #8-12 to inhibit human RNAseH1 and HRHPL at 10 μM. All five compounds inhibited the HBV RNAseH. Compound #8 inhibited RNAseH1 well, #9 and 12 inhibited it weakly, and #10 and 11 had no effect on RNAseH1. Therefore, it is possible to inhibit the HBV RNAseH without inhibiting human RNAseH1.

Anti-HBV RNAseH Compounds can Inhibit HBV Replication in Culture.

Finally, the inventors asked whether HBV RNAseH inhibitors could block HBV replication in culture. Huh7 cells were transfected with genomic expression vectors for HBV genotype A or D isolates, the cells were treated with 10 or 50 μM compounds, and viral nucleic acids were isolated from intracellular HBV capsids after four days. Replicate nucleic acid aliquots were mock treated or treated with DNAse-free *E. coli* RNAseH to destroy RNA:DNA heteroduplexes, and then HBV DNAs were detected by Southern blotting. The signature of RNAseH inhibition is accumulation of RNA:DNA heteroduplexes that migrate as double-stranded species without exogenous RNAseH treatment but as faster-migrating single-stranded DNAs following RNAseH treatment.

Figure 11:
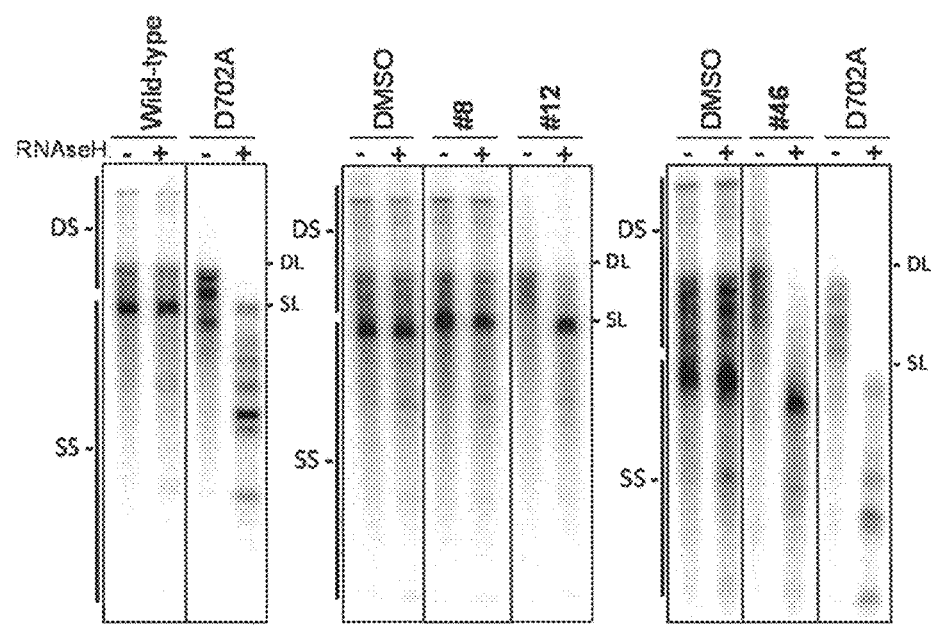
FIG. 11. Inhibition of HBV replication by compounds #12 and 46. Cells replicating HBV were treated with compounds #8, 12 and 46 at 10 µM. HBV DNAs were isolated and duplicate DNA aliquots were either treated with RNAseH or mock treated prior to Southern blotting. The left blot shows DNAs produced by untreated cells transfected with wild-type or D702A RNAseH-deficient genomes. DS, spectrum of all double-stranded nucleic acids; SS, spectrum of all single-stranded nucleic acids; DL, mobility of double-stranded linear HBV DNA; SL, mobility of heat-denatured HBV. Compounds #12 and 46 inhibited production of the slowest-migrating (mature) viral DNA at the top of the double-stranded DNA region and led to accumulation of double-stranded species whose mobility increased following RNAseH treatment. Compound #8 is included as an example compound that did not affect HBV replication.

The mobility of the DNAs synthesized in cells containing the wild-type genotype A genome was unaffected by exogenous RNAseH treatment (FIG. 11). Ablation of RNAseH activity in the D702A mutant altered migration of the double-stranded forms, and treatment of these samples with RNAseH collapsed the double-stranded forms to single-stranded DNAs (FIG. 11, left panel). The mobility of HBV DNAs from cells replicating HBV genotype A treated with DMSO was unaffected by RNAseH digestion (FIG. 11, center panel), but treatment of cells with compound #12 at 10 μM blocked production of the slowest-migrating double-stranded forms and led to accumulation of RNA:DNA heteroduplexes whose mobility increased upon removal of RNA. Treatment of cells with 3 to 50 μM compound #12 revealed that the degree of inhibition was proportional to the concentration of the compound (data not shown). Plus-strand preferential real-time PCR across the gap in the minus-polarity viral DNA revealed that 10 μM compound #12 reduced plus-strand DNA accumulation to 7.3% of the DMSO treated control (data not shown). None of the other compounds reproducibly inhibited HBV genome synthesis (Table 2), but compound #14 (25 μM) inhibited HBV replication in one experiment and #40 (50 μM) inhibited replication in another experiment. Overt cellular toxicity was not observed for any of the compounds at 10 μM. Toxicity was often observed at higher concentrations; this led to the reduced yield of HBV DNA from cultures treated with 50 μM compounds #5, 6, and 8 in FIG. 12.

The effect of the compounds on replication of this genotype D isolate was also tested to evaluate the generality of the results with the genotype A isolate. Treatment of capsid-derived nucleic acids from the DMSO control cells with exogenous RNAseH led to partial conversion of the double-stranded molecules to single-stranded forms. Therefore, RNA:DNA heteroduplexes accumulated in capsids even in the absence of RNAseH inhibitors. This indicates that the RNAseH activity during reverse transcription was incomplete for this isolate. Very few of the most slowly-migrating double-stranded nucleic acids accumulated in cells treated with 10 μM compound #12, and many of the duplex DNAs collapsed to single-stranded forms upon treatment with exogenous RNAseH. Therefore, the inefficient HBV RNAseH in this isolate created a high background, but the inventors were able to detect suppression of the HBV RNAseH activity above background by compound #12 in this assay. None of the other compounds tested against the genotype D isolate detectably inhibited HBV replication (Table 2).

Therefore, compound #12 inhibited replication of HBV genotypes A and D in cells at low M concentrations by blocking RNAseH activity, with the anti-RNAseH effect being somewhat less pronounced than complete ablation of the activity by mutating the RNAseH active site.

Figure 15A:
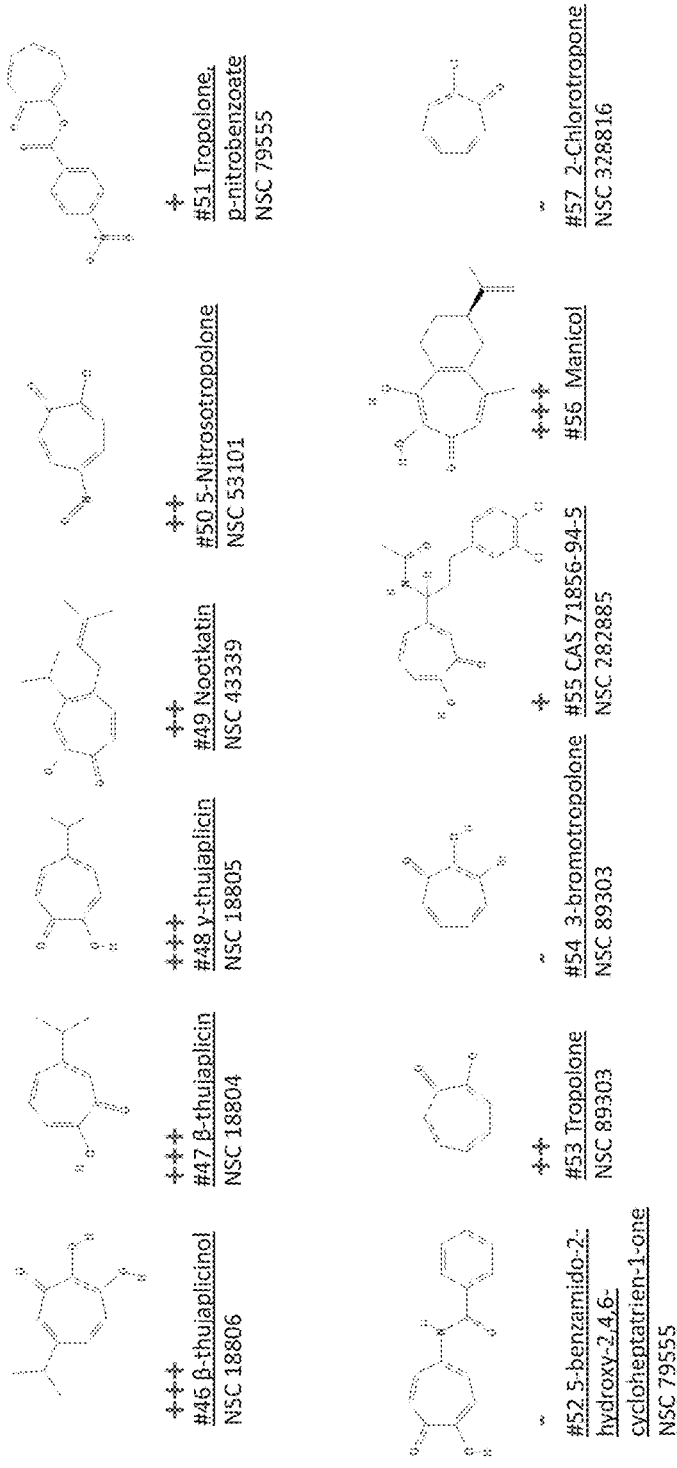
FIG. 15A-B. β-thujaplicinol Derivatives and Their Relative Inhibition of RNAseH Extract.
Figure 15B:
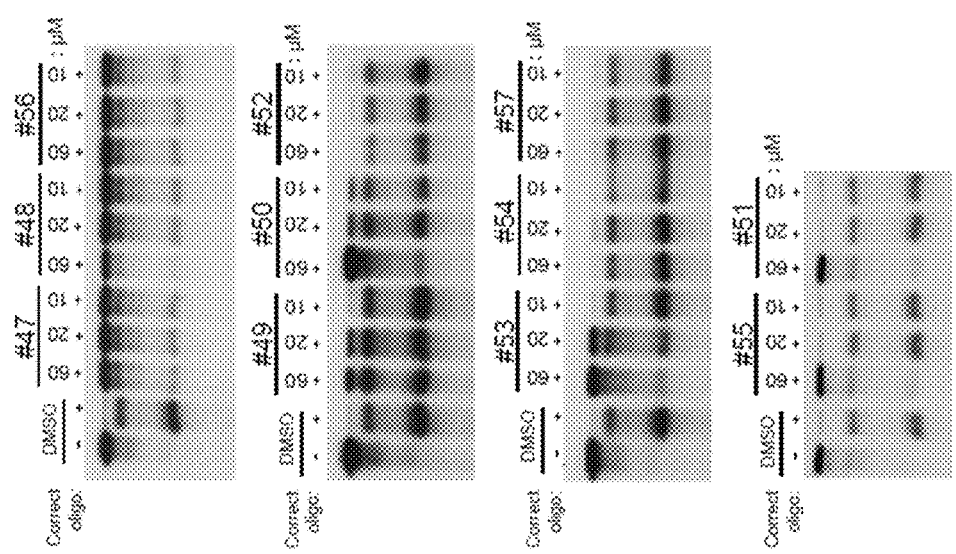

An oligonucleotide-directed RNAseH assay was performed with recombinant HBV RNAseH (genotypes D and H) and recombinant human RNAseH1 in the presence of 0, 5, or 20 μM β-thujaplicinol (FIG. 13A). Inclusion of a non-complementary DNA oligonucleotide (lanes labeled with "−") led to background cleavage signals, whereas inclusion of the complementary oligonucleotide ("+" lanes)

led to cleavage of the radioactively-labeled RNA substrate. Addition of increasing amounts of β-thujaplicinol progressively suppressed HBV RNAseH activity but had little effect on the human RNAseH1. The compound has an $IC_{50}$ of 6 μM against HBV genotype D (FIG. 13B) and a cytotoxic-concentration 50% ($CC_{50}$) of approximately 25 μM in Huh7 cells. An additional 11 derivatives of β-thujaplicinol were screened and eight of these compounds showed some level of inhibition with three compounds showing similar levels of inhibition as β-thujaplicinol (FIG. 15).

Generation of Active Recombinant HBV Genotype C RNAseH.

Figure 16:
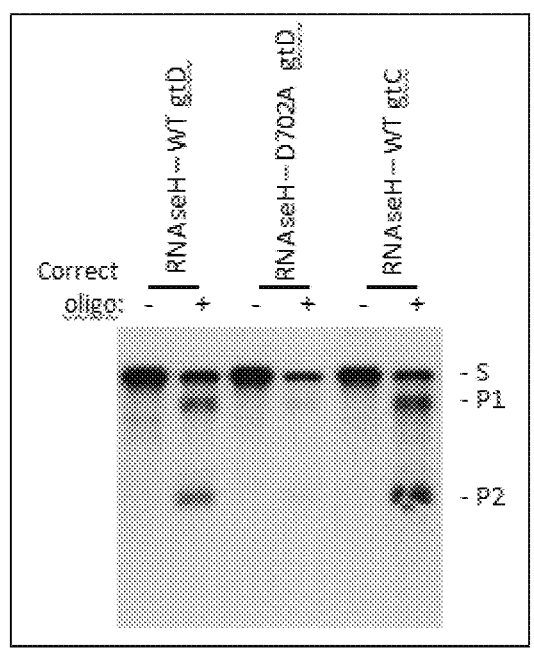
FIG. 16. RNAseH's from different HBV genotypes. HBV has 8 genotypes that differ by >8%, which variation may affect drug sensitivity. Recombinant RNAseH for genotypes B, C, D and H can be detected by Western blotting. Genotype C, D and H recombinant RNAseH's are active.

Incremental improvements were developed in extraction of the HBV RNAseH from the bacterial cell pellets since the data were generated for Examples 1 and 2. Key among these was shifting from using a cup sonicator to a probe sonicator and reducing the duration of the sonication period from 3×60 second bursts to 3×20 second bursts. When the HCV genotype C clone that had inconsistent activity under the old extraction conditions (FIG. 6C) was isolated under these conditions, it became consistently and robustly active (FIG. 16).

Therefore, the inventors can screen for inhibitors of the RNAseH activity against HBV genotypes D, H, and C. Importantly, genotype C HBV is the most wide-spread in southeast Asia (including China) where the majority of HBV-infected patients are located, and it is considered to be the most pathogenic of HBV's 8 genotypes. The availability of active enzyme from 3 different HBV genotypes, including genotype C, therefore greatly increases the probability of identifying inhibitors with broad activity against HBV clinical isolates from multiple genotypes.

Application of the Quantitative PCR Assay for Measuring Inhibition of HBV Replication by RNAseH Inhibitors.

Figure 17:
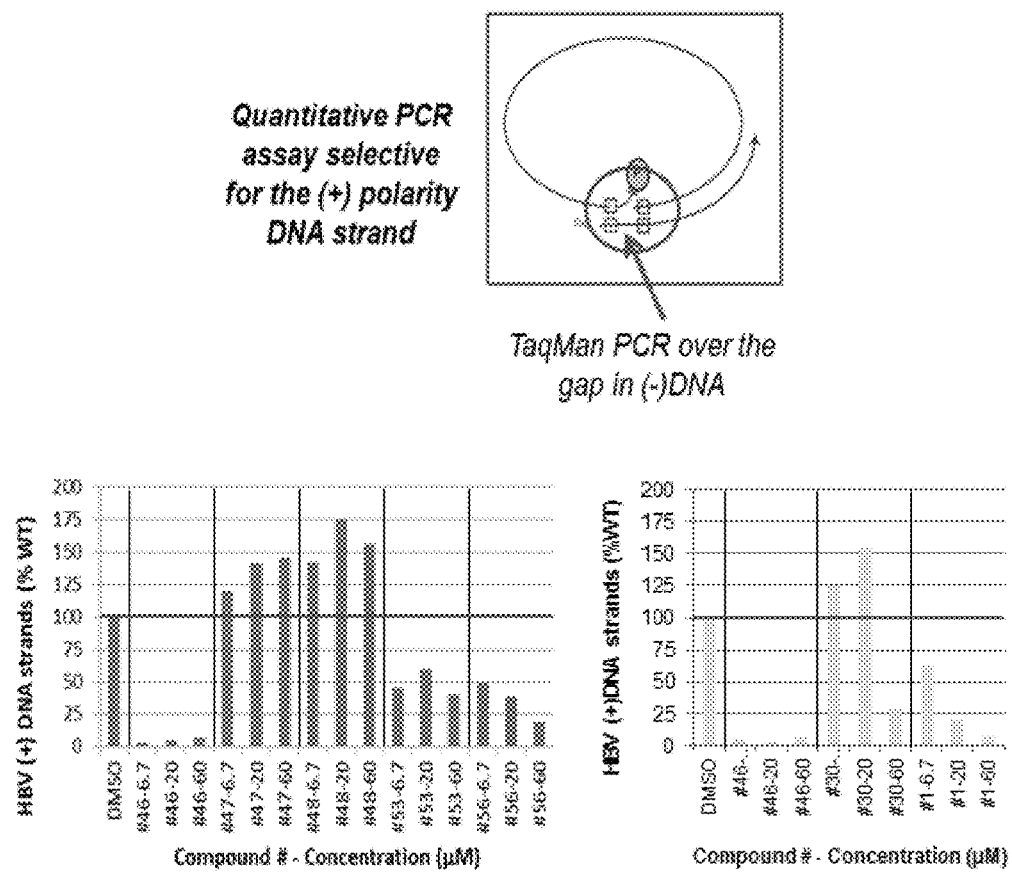
FIG. 17. Inhibition of HBV replication by RNAseH inhibitors. Quantitative PCR assay to assess HBV replication in the presence of various inhibitors.
Figure 18:
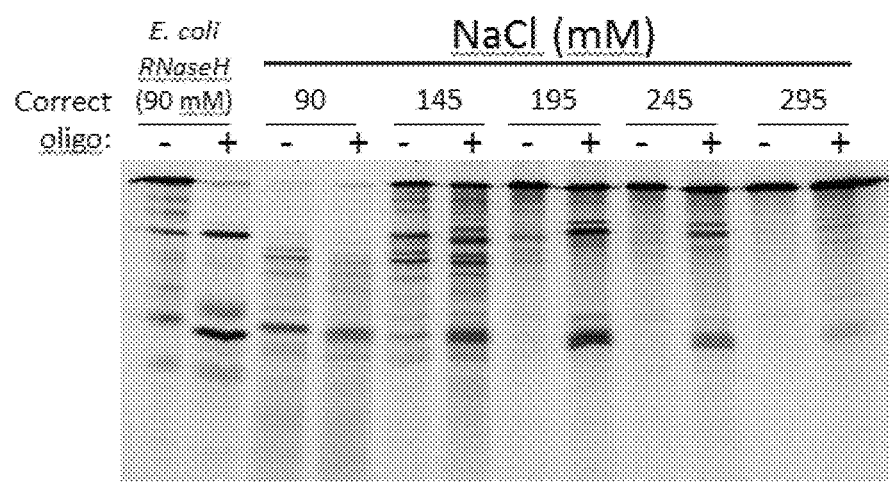
FIG. 18. NaCl Optimum and loss of fidelity in low salt. An Oligonucleotide-directed RNAseH cleavage assay was conducted with recombinant HBV RNAseH at the indicated NaCl concentrations. E. coli, commercial E. coli RNAseH; −, incorrect DNA oligonucleotide polarity; +, correct oligonucleotide polarity. RNAseH activity was most robust at 195 mM and activity declined above this concentration. Digestion of the RNA outside of the region hybridized to the DNA oligonucleotide was observed below 145 mM NaCl, and this non-specific activity became dominant at 90 mM.

The quantitative PCR assay described in section 2.6 of Example 2 measures HBV plus-polarity DNA accumulation by placing the PCR primers and probe across from the gap in the HBV minus-polarity DNA. This assay is useful for quantifying the effect of HBV RNAseH inhibitors because plus-polarity DNA does not accumulate without RNAseH activity. This assay was employed to screen 7 compounds for their ability to suppress HBV replication (FIG. 17). Cells replicating HBV DNA were incubated with DMSO vehicle control or test compounds at 60, 20, or 6.7 μM in a final DMSO concentration (day 0). Fresh medium containing compound was provided on days 1 and 2, and capsid-associated HBV DNAs were isolated on day 3. HBV plus-strand DNAs were measured using the cross-gap TaqMan PCR assay. Compound #46 suppressed viral replication to background at 6.7 μM, and compounds #53, 56, 30, and 1 inhibited accumulation of HBV plus-polarity DNA to lesser extents. Compounds #47 and 48 did not suppress HBV plus-polarity DNA accumulation. This assay provides a faster, cheaper, easier, and more quantitative means to measure the effect of HBV RNAseH inhibitors on viral DNA replication in cells than the Southern blot assay shown in FIGS. 3, 11, and 24 A-C.

Determination of the NaCl Optimum on Activity of Recombinant HBV RNAseH.

An oligonucleotide-directed RNAseH assay was conducted in the presence of NaCl concentrations varying from 90-205 μM to evaluate the effects of monovalent salts on the amount and specificity of the RNA cleavage reaction. The enzyme had a NaCl optimum of 195 μM. Above this level it gradually lost activity. Below this level it also lost activity, but it also lost specificity for RNA:DNA heteroduplexes and became capable of cleaving the single stranded regions of the RNA substrate. This experiment highlights the need to evaluate recombinant HBV RNAseH preparations for specificity for RNA:DNA heteroduplexes as well as for net RNA cleavage activity.

Determination of the Effect of $MnCl_2$ on Activity of the Recombinant HBV RNAseH.

Figure 19:
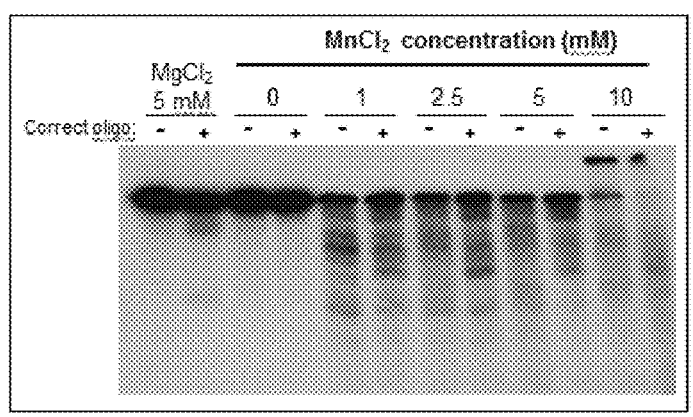
FIG. 19. Effect of $Mn^{++}$ on HBV RNAseH. An oligonucleotide-directed RNAseH cleavage assay was conducted with sufficient recombinant HBV RNAseH to give a weak digestion signal (lanes 1 and 2). The reactions contained either the standard 5 mM $MgCl_2$ (lanes 1 and 2) as a positive control or the indicated concentrations of $MnCl_2$. −, incorrect DNA oligonucleotide polarity; +, correct oligonucleotide polarity. The total amount of RNA digestion was higher in the $MnCl_2$-containing lanes, but the RNAse activity was not specific for the site where the DNA oligonucleotide was bound. Note: amount of enzyme in positive control (5 mM $MgCl_2$) is lower than other experiments and highlights the extreme non-specific cleavage patterns induced by $MnCl_2$.

The physiological ion for most divalent cation-dependent nucleic acid metabolizing enzymes in $Mg^{++}$. In most cases, enzymes will become more active but less specific in the presence of $Mn^{++}$ instead of $Mg^{++}$. Therefore, the inventors determined the effect of replacing the standard cation in the oligonucleotide-directed RNA cleavage assays (5 mM $Mg^{++}$) with 1-10 mM $Mn^{++}$. The assay was conducted under conditions where the positive control reaction containing Mg++ gave a barely-detectable cleavage signal (FIG. 19). A reaction conducted in the absence of divalent cations (0 mM lanes) led to no cleavage of the RNA, confirming the divalent cation-dependency of the HBV RNAseH. Addition of increasing concentrations of $Mn^{++}$ led to extensive cleavage of the RNA at sites outside of the region of RNA:DNA heteroduplex. Therefore, the HBV RNAseH behaves as other nucleic acid metabolizing enzymes, becoming more active but less specific in the presence of $Mn^{++}$. This again highlights the need to evaluate recombinant HBV RNAseH preparations for specificity for RNA:DNA heteroduplexes as well as for net RNA cleavage activity.

3. Discussion

Nucleos(t)ide analog therapy has turned chronic HBV infection into a disease that can be controlled indefinitely, with enormous benefits to patients (Cox and Tillmann, 2011; Kwon and Lok, 2011 and Liaw et al., 2011). However, the infection is very rarely cleared, so treatment is essentially life-long, very expensive, and may be associated with unpredictable long-term side effects. Despite these limitations, the ability of protracted nucleos(t)ide analog therapy to slowly suppress cccDNA and HBsAg and to cure a small minority of HBV patients (Van Bommel, et al., 2010; Woo et al., 2010; Marcellin et al., 2008; Wursthom et al., 2010; Werle-Lapostolle et al., 2004; Cheng et al., 2011 and Wong et al., 2006) indicates that the nucleos(t)ide analogs can push the virus to the brink of elimination. This implies that many more patients could be cured by employing a new drug against a novel HBV target in combination with the nucleos (t)ide analogs to further suppress HBV replication. Here, the inventors report production of recombinant HBV RNAseH suitable for low throughput antiviral drug screening and demonstrate that chemical structure-activity relationships based on HIV RNAseH and integrase inhibitors can guide identification of compounds likely to inhibit the HBV enzyme.

Production of soluble recombinant HBV polymerase or domains of the polymerase is notoriously difficult, and the inventors' experience with the HBV RNAseH domain was no exception. Soluble HBV RNAseH accumulated to low levels in *E. coli* and was a minor component of the extracts even after nickel-affinity enrichment (FIGS. 4A-B). Much of the RNAseH was apparently cleaved near its N-terminus, and these cleavage products are unlikely to be active because their sizes imply that they lack D702. Although the concentration of the intact enzyme was very low, its specific activity was high enough to yield readily detectable signals in both radioactive and fluorescent RNAseH assays (FIGS. 5A-D). Potenza et al. (Potenza et al., 2007) previously expressed recombinant HBV RNAseH that was very similar to HRHPL (genotype D), but their expression conditions led to accumulation of the enzyme in inclusion bodies, necessitating refolding following purification under denaturing conditions. The refolded enzyme possessed RNAse activity, but this activity was not demonstrated to be an RNAseH. Differences between the assays employed here and in Potenza's study prevent comparison of the specificity and specific activity of the enzyme prepared under native and denaturing conditions.

The optimal reaction conditions for the recombinant HBV RNAseH (Table 1) were typical for nucleic-acid modifying enzymes and were similar to conditions in which recombinant hepadnaviral reverse transcriptase is active (Tavis and Ganem, 1993; Lanford, et al., 1995; Hu and Anselmo, 2000 and Beck and Nassal, 2003). Its activity was dependent upon a divalent cation and its specificity for RNA in a heteroduplex was sharply reduced when $Mn^{++}$ was substituted for the physiological cation $Mg^{++}$ (data not shown). This is similar to the reduced fidelity of nucleic acid polymerases (including the duck HBV polymerase) in the presence of $Mn^{++}$ (Lin et al., 2008; Arnold et al., 1999; Pelletier et al., 1996 and Vartanian et al., 1996). The RNAseH had a relatively high NaCl optimum of 190 mM and it lost specificity for heteroduplex RNA at low ionic strength (data not shown). Importantly given that a primary goal of this study was to produce enzyme suitable for antiviral drug screening, recombinant HBV RNAseH was stable upon storage in liquid nitrogen, could be repeatedly frozen and thawed, and was fully active in up to 2% DMSO. Therefore, enzyme suitable for low-throughput anti-HBV RNAseH drug screening has been produced.

The HIV RNAseH is a very active target of ongoing antiviral drug discovery (Klumpp, et al., 2003; Klarmann et al., 2002; Klumpp and Mirzadegan, 2006; Takada, et al., 2007; Bokesch, et al., 2008; Wendeler et al., 2008; Fuji et al., 2009; Su et al., 2010; Di, et al., 2010; Chung, et al., 2010; Williams, et al., 2010; Chung, et al., 2011; Billamboz et al., 2011; Didierjean et al., 2005; Budihas, et al., 2005; Himmel et al., 2009; Shaw-Reid, et al., 2003; Himmel, et al., 2006; Kirschberg et al., 2009; Suchaud et al., 2012; Gong et al., 2011), but to the inventors' knowledge none of the anti-HIV RNAseH compounds have entered clinical trials yet. This is primarily due to the relatively low therapeutic indexes of most known anti-HIV RNAseH compounds. Similar challenges were faced by the HIV integrase field in the early stages of development of anti-integrase drugs. Many inhibitors were discovered, but clinical development did not begin until strand transfer inhibitors, active site metal binders, etc., were discovered. The failure to advance to HIV RNAseH inhibitors to clinical trials may also be partially due to the large number, high potency, and diverse profile of existing anti-HIV drugs. In contrast, current anti-HBV therapies are primarily based on a single class of inhibitors, nucleos(t)ide analogs. Hence, inhibitors of a new HBV enzymatic function would address the current challenges of limited efficacy and cross-resistance among the nucleos(t)ide analogs, and this would allow meaningful combination therapies for HBV similar to HAART that dramatically changed the landscape of anti-HIV therapy.

The ability to template HBV RNAseH drug discovery on the HIV experience would greatly accelerate anti-HBV efforts. The HIV data could narrow the chemical space to be assessed during screening, compounds synthesized during anti-HIV RNAseH screening would be available for immediate screening against HBV, and the toxicity profile of some of these compounds is known. Templating anti-HBV RNAseH drug development on HIV efforts would be analogous to the development of the anti-HBV nucleos(t)ide analogs, which was greatly facilitated by the parallel development of anti-HIV nucleoside analogs (Sturmer, et al., 2009).

The inventors compared the similarity of the HBV and HIV RNAseHs as a first step towards evaluating the feasibility of using HIV studies to guide work with the HBV enzyme. Poor alignments were obtained at the C-termini without extensive manual intervention, impling that the HBV enzyme may fold differently in this region. Despite this prediction, HBV:HIV RNAseH chimeras that substituted all (HHC1) or part (HHC2) of the HBV C-terminal sequences with HIV sequences were enzymatically active (FIGS. 7A-B). Deletion of the chimerized region in HRHPL-dlCT failed to produce active enzyme, indicating that the HIV sequences substitute for the HBV residues by contributing to the enzyme's folding or stability, and/or by directly contributing to the enzymatic reaction. Unfortunately, the mechanism by which the HIV sequences promoted RNAseH activity could not be determined due to their low expression levels. Regardless of the mechanism, these experiments encouraged screening for HBV RNAseH inhibitors based on anti-HIV RNAseH inhibitors.

Twenty-two candidate RNAseH inhibitors were selected due to their similarity to known inhibitors of the HIV RNAseH or integrase. Thirteen of these compounds (59%) inhibited the HBV RNAseH at 10 μM to below the threshold defined by control reactions with irrelevant compounds (FIG. 8, Table 2 and FIG. 13). Importantly, 10 of 11 compounds analogous to anti-HIV integrase compounds inhibited the HBV RNAseH, including both approved anti-HIV integrase drugs, raltegravir (compound #11) and elvitegravir (#10). This is consistent with the membership of both the RNAseH and integrase in the nucleotidyl transferase superfamily of enzymes. Therefore, there is enough similarity between the HBV RNAseH and the HIV RNAseH and integrase active sites to guide screening for anti-HBV RNAseH compounds.

Most anti-HIV RNAseH inhibitors bind to the enzyme and chelate the divalent cations in the active site (Fuji et al., 2009; Su et al., 2010; Chung et al., 2011; Billamboz et al., 2011; Himmel et al., 2009 and Kirschberg et al., 2009). Similarly, anti-HIV integrase compounds that target the active site typically do so by binding to the enzyme or the enzyme plus DNA and chelating the active site divalent cations (Agrawal, et al., 2012). The compounds tested here were selected for the ability to bind to $Mg^{++}$ ions oriented as they are in the HIV RNAseH or integrase active sites, and hence inhibition of the HBV enzyme is predicted to be through binding to the active site and interfering with the $Mg^{++}$ ions. The mechanisms by which the HBV RNAseH inhibitors function have not been explored in detail, but $IC_{50}$ curves reveal at least two patterns. The profiles for compounds #12, 39, and 40 were consistent with the predicted competitive inhibition mechanism (FIG. 9C and data not shown). In these cases, inhibition appears to be specific. Other compounds, such as #6 and #8, had inhibition profiles with one or more broad plateaus, and these profiles were inconsistent with simple competitive binding to the active site. In addition, the electrophoretic mobility of the RNA was retarded at high concentrations of compound #8 (FIG. 9C), implying that this compound may react with the RNA substrate.

The compounds employed here were selected by structure-activity relationships with the goal of testing whether these relationships could predict biochemical inhibition of the HBV RNAseH. The compounds were not selected to have other properties necessary for a drug, such as the ability to enter cells. Nevertheless, compounds #12 and #46 (also called β-thujaplicinol) inhibited HBV replication in cell culture at 10 μM without extensive cellular toxicity (FIGS. 11 and 13). The reduction in mobility following treatment of capsid-derived nucleic acids with *E. coli* RNAseH demonstrates that RNA:DNA heteroduplexes accumulated in the viral capsid in the presence of compounds #12 and 46, confirming that these compounds blocked HBV RNAseH activity in culture. Therefore, it is possible to pharmacologically inhibit the HBV RNAseH in cells, and identification of anti-HBV compounds that are active in cells can be achieved employing structure-activity relationships based on anti-HIV compounds. Furthermore, the ability of compounds identified by screening against recombinant genotype D and H enzymes to inhibit both genotype A and D isolates in culture demonstrates that it is possible to identify RNAseH inhibitors that are active against a range of HBV isolates.

The sensitivity profile of the HBV genotype D and H RNAseHs to the inhibitors was not the same (Table 2). This has two implications. First, the genotype H RNAseH may be a better candidate for primary drug screening than the genotype D enzyme because its inhibition profile more accurately predicted inhibition of HBV replication in culture. Second, the variable sensitivity of the genotype D and H enzymes to the compounds indicates that HBV's high genetic diversity is likely to be an important issue during development of anti-HBV RNAseH drugs.

The key HBV molecule that must be eradicated to cure patients is the viral cccDNA (FIG. 1) (Agrawal et al., 2012 and Zoulim, 2004). Ideally, clearing the cccDNA would be achieved by simultaneously suppressing its synthesis rate with the existing nucleos(t)ide inhibitors and increasing its degradation rate with a new drug. The problem with this approach is that it is not known how to safely destabilize the cccDNA, so the approach that has the most realistic chance of clearing HBV in the foreseeable future is to further suppress its synthesis rate. Importantly, pharmacological suppression of viral genomic synthesis may not need to completely eradicate the cccDNA by itself because the latter stages of viral clearance may be assisted by the immune system. HBV's proteins, including HBsAg (Op den Brouw et al., 2009; Vanlandschoot et al., 2002; Woltman et al., 2011; Wu et al., 2009; Xu et al., 2009 and Cheng et al., 2005), HBeAg (Chen et al., 2005 and Chen et al., 2004), and the polymerase (Wang et al., 2010; Foster et al., 1991 and Wu et al., 2007), have immunosuppressive activities. Consequently, if viral genomic replication can be suppressed far enough to inhibit cccDNA synthesis rather than just virion secretion (FIG. 1) as is usually achieved with the nucleos(t)ide analogs, levels of the cccDNA would drop. This reduction in the transcriptional template would reduce production of HBV's proteins, presumably weakening HBV's immunosuppression and promoting immune-mediated viral clearance.

Three challenges remain prior to beginning full-scale antiviral drug screening against the HBV RNAseH. First, the majority of HBV's disease burden is caused by genotypes B and C, and the inventor have been unsuccessful to date in generating consistently active recombinant RNAseH from these genotypes. This challenge is likely to be surmountable because only a few isolates of these genotypes have been tested for activity and because compound #12 identified by screening against genotypes D and H inhibited replication of HBV genotype A in culture, confirming that cross-genotype inhibition is possible. Second, the existing tissue culture and biochemical assays are sufficient for low throughput drug screening, but anti-HBV RNAseH drug development is anticipated to require screening many thousands of compounds even when the chemical search space is constrained by prior studies with HIV. Therefore, full-scale drug screening and subsequent mechanistic assessment of hit compounds will require improving the yield and purity of the biochemical RNAseH assay. This challenge should be met by further optimizing the induction and extraction conditions, expanding the bacterial induction cultures beyond the 100 ml scale used in this study, adding a second purification step such as ion-exchange chromatography, and expanding efforts to control proteolysis of the enzyme. The inventor is optimistic this goal can be achieved because recent efforts altering the induction and extraction conditions have increased the specific activity of the enzyme approximately four-fold, and initial scale-up experiments have not met with difficulty. Finally, the HBV RNAseH assay must be adapted to a format suitable for high throughput screening. This challenge should also be surmountable because fluorescent RNAseH assays have been widely employed to screen for anti-HIV RNAseH inhibitors and because the signal:background ratio for the first-generation HBV RNAseH fluorescent assay in FIG. 5 should be improved by increasing the concentration of the RNAseH and/or by optimizing the substrate structure.

TABLE 1

| Optimal reaction conditions | |
|---|---|
| Tris pH 7.5 | 65 mM |
| NaCl | 190 mM |
| $MgCl_2$ | 5 mM |
| DTT | 5 mM |
| Glycerol | 6% |
| DMSO | 1% |
| NP40 | 0.05% |
| DNA Oligo (20 mer) | 0.1 μg/μl |
| RNA (264 nt) | 0.025 μg/μl |
| Temperature | 42° C. |
| RNAseIn | 0.5 U/μl |

TABLE 2

| JT Compound Number | Formal name | Tool Set number | Reference enzyme | Derivative series | Activity vs. HBV | | | Activity vs. human RNAseH1 |
|---|---|---|---|---|---|---|---|---|
| | | | | | Biochemical vs. gtD | Biochemical vs. gtC | Genomic Replication | |
| 1 | FCHC 2456 | 3 | R | 1 | +++ | +++ | ++ | + |
| 41 | TRC C432800 (Ciclopirox) | 3 | R | 1 | − | | | + |
| 42 | Labotest 72543251 | 3 | R | 1 | − | | | + |
| 43 | Sigma PH008969 | 3 | R | 1 | − | + | | − |
| 44 | Labotest 12243782 | 3 | R | 1 | − | | | − |
| 45 | TCI America H1040 | 3 | R | 1 | − | + | − | − |
| 2 | Sigma 74540 | 1 | R | | − | | | − |

TABLE 2-continued

| JT Compound Number | Formal name | Tool Set number | Reference enzyme | Derivative series | Activity vs. HBV Biochemical vs. gtD | Biochemical vs. gtC | Genomic Replication | Activity vs. human RNAseH1 |
|---|---|---|---|---|---|---|---|---|
| 3 | Sigma n8164 | 1 | R |  | − |  | − |  |
| 4 | TimTec ST029023 | 1 | R |  | + |  | − |  |
| 5 | Enamine T0506-3483 | 1 | R | 5 | + |  | − |  |
| 19 | Sigma-586862 | 2 | R | 5 | − |  |  |  |
| 20 | Sigma-L133671 | 2 | R | 5 | − | − |  |  |
| 21 | Sigma-S647632 | 2 | R | 5 | − |  |  |  |
| 33 | Indofine-17-083 | 2 | R | 5 | − |  |  |  |
| 6 | Chembridge 7929959 | 1 | R | 6 | + |  | − |  |
| 24 | Chembridge-7933420 | 2 | R | 6 | − |  |  |  |
| 25 | Chembridge-7878467 | 2 | R | 6 | − |  |  |  |
| 26 | Chembridge-7962359 | 2 | R | 6 | − |  |  |  |
| 27 | Chembridge-7698174 | 2 | R | 6 | − |  |  |  |
| 28 | Chembridge-7570508 | 2 | R | 6 | − |  |  | + |
| 29 | Chembridge-7943262 | 2 | R | 6 | − |  |  |  |
| 32 | Enamine-T6060486 | 2 | R | 6 | − |  |  |  |
| 37 | Vistas M Lab-STK082278 | 2 | R | 6 | − |  |  |  |
| 7 | Idofine 02030 | 1 | I |  | − |  | − | +++ |
| 8 | Sigma S439274 | 1 | I | 8 | ++ |  | − | +++ |
| 30 | Chembridge-7248520 | 2 | I | 8 | +++ | ++ | + | +++ |
| 31 | Chembridge-5104346 | 2 | I | 8 | +++ |  | − | +++ |
| 34 | Indofine-D-009 | 2 | I | 8 | ++ | +++ | − | + |
| 35 | TCI America-D1118 | 2 | I | 8 | +++ |  | − | +++ |
| 9 | Sigma 70050 | 1 | I |  | ++ |  | − | ++ |
| 10 | Selleck S2001 (Elvitegravir) | 1 | I | 10 | ++ | ++ | − | − |
| 11 | Selleck S2005 (Raltegravir) | 1 | I | 10 | ++ | ++ | − | − |
| 40 | 118-D-24 (NIH) |  | I | 10 | +++ |  | − |  |
| 64 | Sigma CDS015295 | 5 | I | 10 | + | − |  |  |
| 65 | Sigma O0877 | 5 | I | 10 | − |  |  |  |
| 66 | Sigma PHR1174 | 5 | I | 10 | − |  |  |  |
| 67 | Sigma 17850 | 5 | I | 10 | − |  |  |  |
| 68 | Sigma O8757 | 5 | I | 10 | − |  |  |  |
| 69 | Sigma R747092 | 5 | I | 10 | ++ | + |  |  |
| 70 | Sigma N8878 | 5 | I | 10 | − |  |  |  |
| 71 | Enoxacin | 5 | I | 10 | − | − |  |  |
| 72 | BMS-707035 | 5b | I | 10 | ++ | + |  |  |
| 73 | Dolutegravir | 5b | I | 10 | + | − |  |  |
| 74 | MK-2048 | 5b | I | 10 | − |  |  |  |
| 77 | CAS 518048-03-8 | 5b | I | 10 | − |  |  |  |
| 12 | napthyridinone | S | R |  | +++ | +++ | ++ |  |
| 13 | KHMP05 | S | R |  | − |  | − |  |
| 14 | KHMP02 | S | R |  | − |  | − |  |
| 15 | BHMP07 | S | R |  | − |  | − |  |
| 22 | Sigma-N8164 | 2 | R |  | − |  |  |  |
| 38 | Vistas M Lab-STK317995 | 2 | R |  | +++ |  |  |  |
| 46 | beta-thujaplicinol | 4 | R | 46 | +++ | +++ | ++ | − |
| 47 | beta-thujaplicin | 4 | R | 46 | +++ | − | − | − |
| 49 | Nootkatin | 4 | R | 46 | ++ |  | − |  |
| 50 | 5-nitrosotropolone | 4 | R | 46 | ++ |  | + | − |
| 51 | tropolone p-nitrobenzoate | 4 | R | 46 | + |  |  |  |
| 52 | NSC 79556 | 4 | R | 46 | − |  |  | − |
| 53 | Tropolone | 4 | R | 46 | ++ |  | − |  |
| 54 | 3-bromotropolone | 4 | R | 46 | − |  |  |  |
| 55 | NSC 282885 | 4 | R | 46 | + |  |  | + |
| 56 | Manicol | 4 | R | 46 | +++ | +++ | + | − |
| 57 | 2-chlorotropone | 4 | R | 46 | − |  |  |  |
| 59 | Chembridge 5945310 | 4 | R | 46 | − |  |  | + |
| 60 | Chembridge 5942159 | 4 | R | 46 | − |  |  |  |
| 61 | Chembridge 5940946 | 4 | R | 46 | − |  |  | ++ |
| 62 | Chembridge 5946384 | 4 | R | 46 | + |  |  |  |
| 63 | Chembridge 5938894 | 4 | R | 46 | − |  |  |  |

Figure 12:
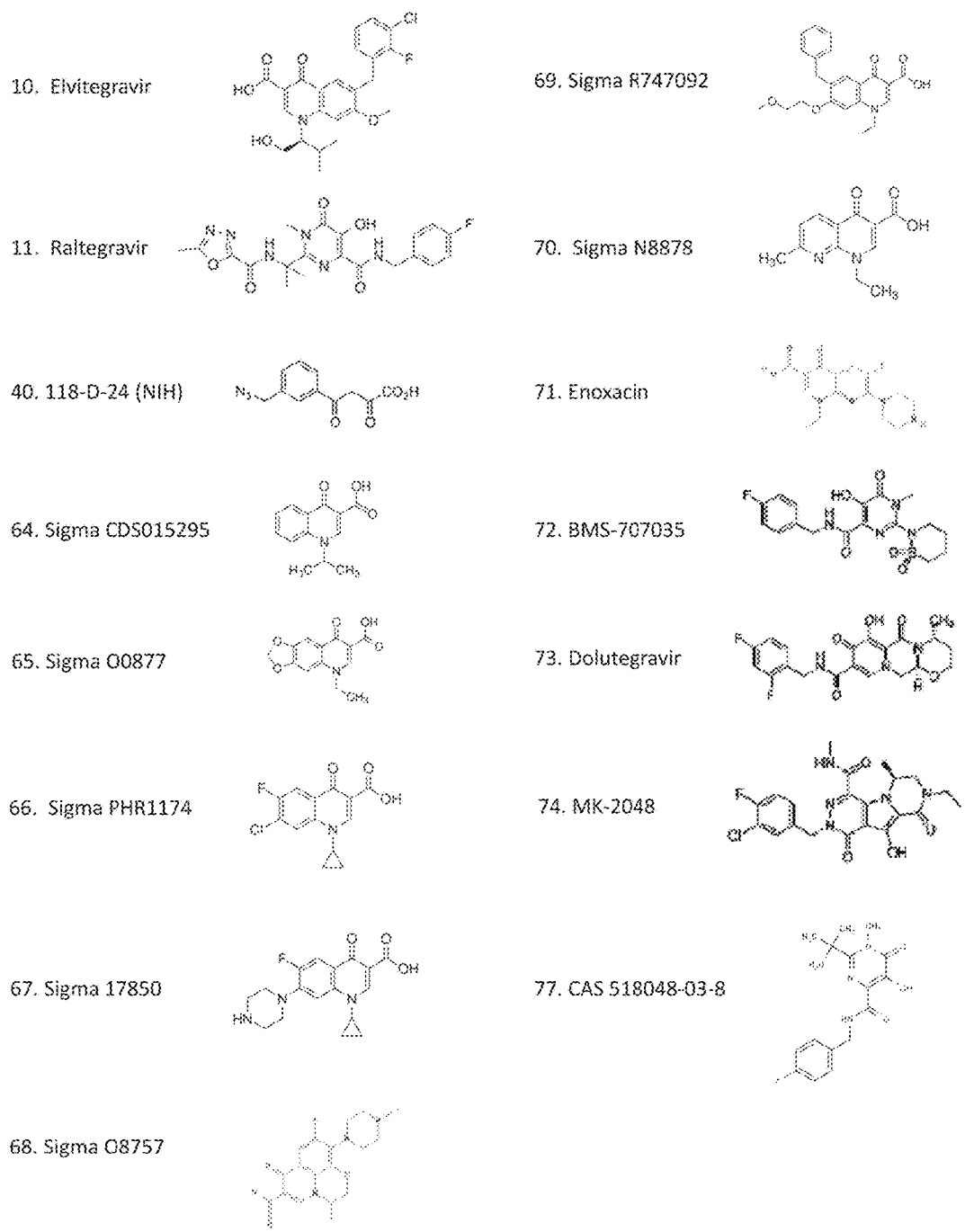
FIG. 12. Chemical structures of the compounds tested. Compounds are named by the company/product number or their formal names, as appropriate. The approved anti-HIV integrase drugs elvitegravir (#10) and raltegravir (#11) are listed by their common names, pharmaceutical developer's codes, and company/product numbers.

[1] Structures are found in FIGS. 12 and 15
[2] Biochemical assays: +++ inhibition at 10 μM; ++ inhibition at 20 μM; + inhibition at 60 μM; − no inhibition at 60 μM
[3] Replication assays: ++, clear activity at <10 μM; +, activity detectable at >10 μM; − no activity at 60 μM
[4] Series affiliations: 1 = Ciclopirox derivatives; 5 = Cyanopyran derivatives; 6 = Aminocyanothiophenes; 8 = Hydroxyanthenones; 10 = Elvitagravir and related HIV integrase inhibitors; 46 = Hydroxylated tropolones

TABLE 3

Residual activity in RNAseH reactions conducted in the presence of 10 μM of the test compounds

| Compound | Residual activity at 10 uM[1] | | |
|---|---|---|---|
| | Genotype D | Genotype H | HHC1 |
| 2 | 54 ± 18 | 67 ± 20 | 35 ± 6 |
| 3 | 43 ± 14 | 68 ± 14 | 60 ± 19 |
| 4 | 35 ± 6 | 68 ± 18 | 37 ± 5 |
| 5 | 42 ± 15 | 76 ± 14 | 36 ± 6 |
| 6 | 40 ± 16 | 81 ± 24 | 55 ± 23 |
| 7 | 45 ± 19 | 68 ± 24 | 56 ± 13 |
| 8 | 33 ± 17 | 74 ± 21 | 55 ± 18 |
| 9 | 33 ± 10 | 66 ± 23 | 58 ± 15 |
| 10 | 30 ± 8 | 66 ± 21 | 35 ± 7 |
| 11 | 29 ± 18 | 63 ± 21 | 59 ± 23 |
| 12 | 28 ± 12 | 17 ± 6 | 32 ± 8 |
| 13 | 52 ± 12 | 42 ± 26 | 65 ± 14 |
| 14 | 46 ± 20 | 27 ± 13 | 72 ± 2 |
| 15 | 47 ± 4 | 37 ± 23 | 68 ± 6 |
| 30 | 23 ± 6 | 37 ± 8 | 58 ± 12 |
| 31 | 26 ± 15 | 50 ± 10 | 42 ± 12 |
| 34 | 30 ± 15 | 33 ± 12 | 39 ± 4 |
| 35 | 27 ± 14 | 38 ± 20 | 39 ± 9 |
| 38 | 24 ± 1 | 38 ± 25 | 32 ± 4 |
| 39 | 21 ± 2 | 26 ± 0 | 60 ± 24 |
| 40 | 21 ± 16 | 22 ± 2 | 44 ± 10 |

[1]Percent DMSO control ± standard deviation
Values are normalized to vehicle control reactions containing 1% DMSO and the error bars represent the standard deviation from 3 to 7 replicate experiments.

Example 2

1. Materials and Methods
2.1. Plasmids and Viral Strains Employed.

Codon-optimized coding sequences for recombinant genotypes D and H HBV RNAseH (HRHPL) with a C-terminal hexahistidine tag were cloned by gene synthesis in pTrcHis2B (Invitrogen). Genotype D HRHPL encodes HBV polymerase residues 684-845 from Genbank V01460; the genotype H clone encodes the homologous amino acid sequences from Genbank AB298362. The human RNAseH1 gene (NP_002927.2) was cloned with an N-terminal hexahistidine-tag in pRsetB (Invitrogen) by gene synthesis. pCMV-HBV-LE- is an HBV over-length genomic expression vector with mutations that block HBV surface protein expression for biosafety reasons. It contains 1.2 copies of the HBV (adw2, genotype A) genome (Genbank X02763.1) downstream of the CMV promoter in pBS (Promega). pCMV-HBV(gtD) is an analogous HBV genomic expression construct for genotype D that expresses wild-type surface antigen proteins.

2.2. Compound Acquisition.

βTJ was obtained from the Drug Synthesis and Chemistry Branch, Developmental Therapeutics Program, Division of Cancer Treatment and Diagnosis, National Cancer Institute. It was dissolved in dimethyl sulfoxide (DMSO) at 10 mM and stored at −80° C.

2.3. RNAseH Expression and Enrichment.

HRHPL and human RNAseH1 were expressed in *E. coli* and enriched by nickel-affinity chromatography as described (Tavis et al., 2013). The enriched extracts were dialyzed into 50 mM HEPES pH 7.3, 300 mM NaCl, 20% glycerol, and 5 mM DTT, and stored in liquid nitrogen.

2.4. Biochemical RNAseH Assays.

Oligonucleotide-directed RNAseH cleavage assays (Gong et al., 2001) were performed as described (Tavis et al., 2013). Briefly, HBV RNAseH extracts were mixed with a 264 nt-long internally $^{32}$P-labeled RNA plus an excess of a complementary DNA oligonucleotide or its inverse-complement as a negative control in a final concentration of 65 mM Tris pH 8.0, 190 mM NaCl, 5 mM MgCl$_2$, 5 mM dTT, 0.05% NP40, and 6% glycerol. βTJ was dissolved in DMSO and added at the indicated concentrations; the final concentration of DMSO in all reactions was 1%. The reactions were incubated at 42° C. for 90 min. and terminated by addition of Laemmli protein electrophoresis buffer. The samples were resolved by SDS-PAGE, labeled RNA was detected by autoradiography, the autoradiograms were scanned, and the RNA cleavage products were quantified with ImageJ (National Institutes of Health). IC$_{50}$ values were calculated by non-linear regression using GraphPad Prism (GraphPad Software, Inc.).

2.5. HBV Replication Inhibition Assays.

Inhibition of HBV replication by βTJ was measured as recently described (Tavis et al., 2013). Briefly, Huh7 cells were transfected with HBV genomic expression vectors using TransIT-LT1 (Mirus, Inc.), βTJ was added 12-16 hrs post-transfection at the indicated concentrations, and fresh medium containing the compounds was provided two days later. HBV core particles were isolated four days post-transfection by detergent lysis of the cells and sedimentation through a sucrose cushion as described (Tavis et al., 1998). Viral DNAs were isolated from cytoplasmic core particle preparations by proteinase K digestion followed by phenol/chloroform extraction as described (Gong et al., 2001). Duplicate aliquots of each nucleic acid preparation were treated with 2 U *E. coli* DNAse-free RNAseH (Invitrogen) at 37° C. for 30 min. or were mock treated. The nucleic acids were resolved by electrophoresis on 1.2% agarose gels and HBV DNAs were detected by Southern blotting with $^{32}$P-labeled double-stranded HBV DNA as a probe to detect both the plus- and minus-polarity HBV DNA strands. HBV core protein (HBc) and β-actin in the cytoplasmic lysates were monitored by western analysis using an anti-HBc antibody (HBP-023-9, Austral Biologicals) and a mouse anti-3-actin monoclonal antibody from ZSGB-BIO Co., Ltd., respectively. HBV surface antigen (HBs) proteins were quantified by ELISA (Shanghai Kehua Biotech).

2.6. Real-Time PCR Quantification of HBV DNA.

Plus-polarity preferential quantitative TaqMan PCR for the HBV DNA was conducted employing forward primer GGAGGCTGTAGGCATAAATTGG (SEQ ID NO: 13), reverse primer AGATGATTAGGCAGAGGTGAAAAAG (SEQ ID NO:14), and probe 5'-6Fam-CTGCGCACC-Zen-AGCACCATGCA-IabkFQ-3' (5'-6Fam-SEQ ID NO:15-Zen-SEQ ID NO: 16-IabkFQ-3') (Integrated DNA Technologies). PCR was conducted on purified HBV capsid-derived nucleic acids for 40 cycles of 95° C. for 15 sec. and 65° C. for 1 min. employing the TaqMan universal PCR master mix (Applied Biosystems). Results were standardized against serial dilutions of cloned HBV DNA. The EC$_{50}$ was estimated by linear regression of the real-time PCR data.

2.7. Cytotoxicity.

Toxicity of βTJ in Huh7 cells was determined with 3-(4,5-dimethylthiazol-2-yl)-5-β-carboxymethoxyphenyl)-2-(4-sulfophenyl)-2H-tetrazolium (MTS) assays that measures mitochondrial dysfunction employing the Cell Titre 96 aqueous nonradioactive cell proliferation assay (Promega), and with the CytoTox-Glo assay (Promega) that reflects cellular integrity. Huh7 and HepG2 cells (1×10$^4$) were plated in 96-well tissue culture plates, medium containing βTJ at the indicated concentrations was added the next day, the medium was replaced with fresh medium containing βTJ after two days, and after four days the MTS or CytoTox-Glo assays were conducted according to the manufacturer's instructions. The 50% cytotoxicity concentrations ($CC_{50}$) were calculated by non-linear regression with GraphPad Prism.

2. Results 3.1. Inhibition of Recombinant HBV RNAseH by βTJ.

The inventor recently expressed recombinant HBV genotype D and H RNAseH in *E. coli* and enriched the enzymes by nickel-affinity chromatography (Tavis et al., 2013). The HBV RNAseH was a minor component in these enriched extracts. It was undetectable by Coomassie staining but was detectable by western analysis with the anti-HBV RNAseH domain monoclonal antibody 9F9 (FIG. 21A). The concentration of full-length HRHPL was estimated to be 0.5 ng/μl in these extracts by comparison in western blots to full-length HBV polymerase at a known concentration. The RNAseH activity of this enzyme was readily detected using an oligonucleotide-directed RNA cleavage assay, and the HBV enzyme was proven to be the source of this activity by mutating two key active site "DEDD" residues (FIGS. 21B and 21C). In this assay, a DNA oligonucleotide is annealed to a uniformly-labeled RNA to create an RNA:DNA heteroduplex and cleavage of the RNA in the heteroduplex yields two RNA fragments. The RNAs are resolved by electrophoresis, detected by autoradiography, and the cleavage products are quantified by densitometry. Control experiments that varied the reaction time from 20 to 90 min and the amount of RNAseH from 1-3 ng demonstrated that the assay is linear with respect to both time and enzyme concentration (FIG. 21D). Addition of βTJ to the RNAseH assays at concentrations ranging from 0.02 to 100 μM revealed that βTJ inhibited the RNAseH, with 50% inhibitory concentrations ($IC_{50}$) of 5.9±0.7 μM for the genotype D RNAseH and 2.3±1.7 μM for the genotype H enzyme (FIG. 22A-C).

3.2. Effect of βTJ on Human RNAseH1.

Figure 23:
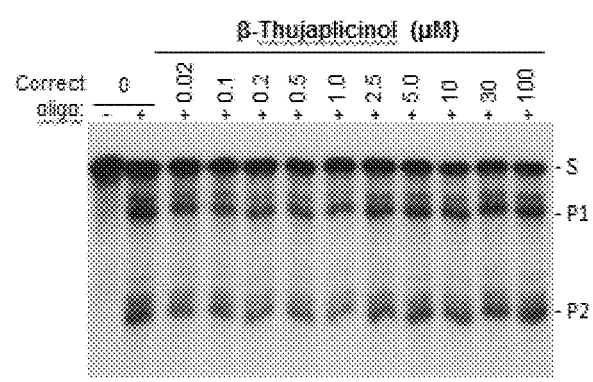
FIG. 23. βTJ does not inhibit recombinant human RNAseH1 in the oligonucleotide-directed RNAseH assay. Oligonucleotide-directed RNAseH assay employing recombinant human RNAseH1. S, substrate; P1, larger RNA cleavage product; P2, smaller RNA cleavage product.

RNAseH1 is responsible for about 80% of the RNAseH activity in human cells (Lima et al., 2007; Lima et al., 2001), and hence inhibition of it would be a possible contributor to cellular toxicity from anti-HBV RNAseH drugs. Therefore, we expressed the human RNAseH1 in *E. coli*, enriched it by nickel affinity chromatography as described (Tavis et al., 2013), and tested the effects of βTJ on the recombinant human enzyme in oligonucleotide-directed RNAseH assays. Inclusion of βTJ from 0.02 to 100 μM had no effect on RNAseH1 activity in this assay (FIG. 23).

3.3. Inhibition of HBV Replication by βTJ.

βTJ was tested for its ability to suppress HBV replication in culture. Huh7 human hepatoma cells were transfected with HBV genomic expression vectors to initiate HBV replication, medium containing vehicle or βTJ at 2.5, 10, 15, and 20 μM was added the following morning, and the βTJ-containing medium was refreshed two days later. After four days, the cells were lysed, HBV capsid particles were isolated by sucrose sedimentation, and nucleic acids were purified. Replicate nucleic acid aliquots were mock treated or treated with DNAse-free *E. coli* RNAseH to destroy RNA:DNA heteroduplexes, and then HBV DNAs were detected by Southern blotting employing a HBV DNA probe that detects both strands of the viral DNA.

RNAseH deficiency blocks synthesis of HBV plus-polarity DNA and consequently blocks production of the slowest-migrating, most-mature relaxed circular form of the viral DNA (RC DNA). It also causes accumulation of RNA:DNA heteroduplexes in which the DNA migrates as double-stranded species in the absence of exogenous RNAseH treatment, but as faster-migrating single-stranded species upon degradation of the RNA strand. Therefore, inhibiting the RNAseH activity in this experiment would have two effects. First, the amount of the RC DNA in the mock-treated sample would be reduced. Second, DNAs that appeared as double-stranded forms in the mock-treated aliquot would migrate faster in the RNAseH-treated aliquot of the same nucleic acid preparation.

DNAs produced by the wild-type genome contained the mature RC DNA, and mobility of the spectrum of double-stranded species was unaffected by RNAseH treatment (FIG. 24A, compare the mock-treated sample in lane 1 to the RNAseH-treated sample in lane 2). Cells transfected with an RNAseH-deficient genome carrying a mutation in an essential active site DEDD residue (D702A) did not produce mature RC DNA (FIG. 24A lane 3); rather, the viral DNAs were found in duplexes that collapsed to single-stranded forms in the RNAseH-treated aliquot (FIG. 24A compare lanes 3 and 4). The heterogeneity in length of the minus-polarity DNA strands revealed following treatment with *E. coli* RNAseH was due to stalling of minus-polarity DNA synthesis in the absence of removal of the RNA strand during reverse transcription that we previously reported (Gerelsaikhan et al., 1996).

Treating cells replicating a wild-type genotype A HBV isolate with βTJ suppressed accumulation of the RC DNA and led to accumulation of RNA:DNA heteroduplexes whose mobility increased upon removal of the RNA strand (FIG. 24B, compare lanes 1 and 2 to the pairs of βTJ-treated samples, for example, lanes 5 and 6). The proportion of HBV DNAs found in heteroduplexes (i.e., DNA strands whose mobility increased following treatment with exogenous RNAseH) increased at higher βTJ concentrations, and the total amount of viral DNA detected was suppressed at 15 and 20 μM. Similar results were observed when cells replicating a HBV genotype D isolate were evaluated (FIG. 24C).

The HBV plus-polarity DNA strand was measured to quantify the effects of βTJ on HBV replication because plus-polarity DNA cannot be made without RNAseH activity. Real-time PCR primers flanking the gap in the HBV minus-polarity DNA were designed that preferentially measure plus-polarity DNA because amplification across the gap in the minus-polarity DNA is inefficient. Plus-polarity preferential PCR revealed that βTJ suppressed HBV genotype A replication to 79±20% relative the DMSO-treated control at 2.5 μM (FIG. 24D). Above 10 μM, βTJ suppressed HBV plus-polarity DNA levels to below the assay background of approximately 14% that was determined with the D702A RNAseH-deficient genome. This implies a 50% effective concentration ($EC_{50}$) for βTJ against this genotype A isolate in Huh7 cells of approximately 5 μM.

Three control experiments were conducted to determine whether βTJ treatment affected viral or cellular protein accumulation during this four day assay. First, levels of the HBV core protein (HBc) in cytoplasmic extracts were measured by western analysis. Although some sample-to-sample variation was observed in western analysis of HBc in the cellular extracts, HBc levels at the higher βTJ concentrations were similar to those in the DMSO vehicle control (FIGS. 24B and C). Second, β-actin was detected in extracts from βTJ-treated cells by western blots as a marker for cellular protein accumulation. Actin levels were unchanged at day four post-transfection (FIGS. 24B and C). Finally, levels of the viral surface proteins (HBs) in the medium were analyzed by ELISA to evaluate whether βTJ altered viral protein secretion. HBs expression and secretion by the genotype D isolate was unaffected by βTJ at the end of the experiment even at 20 μM (FIG. 24E). Therefore, βTJ did not substantially affect viral protein expression or overall cellular protein levels over the course of this experiment.

3.4. Cytotoxicity.

Toxicity of βTJ in Huh7 cells was assessed by measuring mitochondrial function with an MTS assay, and also by measuring membrane integrity as reflected by release of cytoplasmic proteases into the culture medium employing the CytoTox-Glo assay (Promega). In both assays, cells were plated at the same density employed in the HBV replication assays, medium containing various concentrations of βTJ was added, the βTJ-containing medium was refreshed on day 2, and the toxicity assays were conducted after four days. βTJ was moderately toxic by the MTS assay, with a 50% cytotoxicity concentration ($CC_{50}$) value of 10.1±1.7 µM. However, βTJ was much less toxic by the membrane integrity assay, with a $CC_{50}$>150 µM (FIG. 25A). The low toxicity in the membrane integrity assay was consistent with the unchanged levels of HBc, HBs, and β-actin detected at the end of the assay (FIG. 24A-E). Therefore, PβTJ has a significant impact on mitochondrial function in Huh7 cells, but this effect was not enough to kill the cells during the four day HBV replication assay.

Toxicity of βTJ was also assessed in HepG2 cells because these cells are another human hepatocyte-derived cell line that supports HBV reverse transcription. The $CC_{50}$ of βTJ in HepG2 cells was 16.7±3.7 µM by the MTS assay, similar to its effect on Huh7 cells (FIG. 24B).

3. Discussion

The inventor hypothesized that βTJ may inhibit the HBV RNAseH because it is active against the HIV RNAseH (Beilhartz et al., 2009; Budihas et al., 2005; Farias et al., 2011). As predicted, βTJ inhibited recombinant HBV RNAseH with low micromolar $IC_{50}$ values in biochemical assays, and it blocked HBV replication in cell culture by inhibiting the RNAseH in its native context within the full-length HBV polymerase. βTJ was effective against HBV genotype D and H isolates in biochemical assays and against genotype A and D isolates in the replication assays, indicating that its efficacy against HBV is not genotype-specific.

βTJ has an $IC_{50}$ value of 0.2-0.3 µM against the HIV-1 RNAseH (Beilhartz et al., 2009; Budihas et al., 2005; Farias et al., 2011), but its $IC_{50}$ against the HBV RNAseH was 5.9 and 2.3 µM for the genotype D and H enzymes, respectively. This ~10-fold difference was not surprising because the HBV enzyme is genetically distant from the HIV RNAseH, sharing only about 23% amino acid identity in the core RNAseH domain with its HIV counterpart.

βTJ can efficiently inhibit the HIV RNAseH in biochemical assays, but it is inactive against HIV replication in cells (Chung et al., 2011). In contrast, βTJ inhibited HBV replication in Huh7 cells by targeting the viral RNAseH activity (FIGS. 24A-E). βTJ is only the second compound demonstrated to inhibit HBV replication by blocking the viral RNAseH activity, and this is the first time that a tropolone has been shown to inhibit the HBV RNAseH. The inventor previously reported that napthyridinone inhibited the HBV RNAseH with an $IC_{50}$ of 2.5 µM and that it blocked viral replication in Huh7 cells by ~93% at 10 µM (Tavis et al., 2013). Like βTJ, napthyridinone was moderately toxic, with an estimated $CC_{50}$ in the low µM range in Huh7 cells by the MTS assay. The inventor's observation with βTJ confirms that the HBV replication can be pharmacologically inhibited in cells by targeting the RNAseH. Because βTJ was selected for analysis due to its ability to inhibit the HIV RNAseH, these data emphasize the high potential for success from screening inhibitors of the HIV RNAseH for ability to inhibit the HBV enzyme.

βTJ induced substantial toxicity during the four day HBV replication assays in Huh7 cells, with $CC_{50}$ of 10.1 µM by the MTS assay (FIG. 25A). This is similar to the $CC_{50}$ of 2.3 M that has been reported for βTJ in CEM-SS cells (Chung et al., 2011) and the value of 16.7 µM in HepG2 cells (FIG. 25B). This toxicity appears to be due to mitochondrial dysfunction because the MTS assay measures mitochondrial function. Furthermore, mitochondrial toxicity has been reported for the related compounds β-thujaplicin, tropolone, and tropone in rat hepatocytes (Nakagawa and Tayama, 1998). An alternative mechanism of toxicity due to inhibition of the human RNAseH 1 appears unlikely because βTJ failed to inhibit recombinant human RNAseH1 in our RNAseH assay even when a wide range of enzyme and inhibitor concentrations were employed (FIG. 23 and data not shown). However, βTJ has been reported to have an $IC_{50}$ of 3.5 µM against a similar recombinant N-terminally hexahistidine-tagged human RNAseH1 (Budihas et al., 2005). The inventor's RNAseH1 preparation can be inhibited to varying degrees by other RNAseH antagonists (including napthyridinone) (Tavis et al., 2013), so the reason(s) for this discrepancy is unknown. The much lower toxicity of βTJ in Huh7 cells as measured by the membrane integrity assay ($CC_{50}$>150 µM) in this short-term assay is consistent with the MTS assay reflecting a direct action of the inhibitor on the cell. In this context, the lower toxicity measured by the membrane integrity assay would reflect the time needed for mitochondrially-mediated toxicity to cause cellular lysis.

Direct inhibition of HBV replication by βTJ that was independent of its negative impact on cells could be discerned for three reasons. First, HBV capsid protein (HBc) accumulation in the cells (FIGS. 24B-C, bottom panels) and secretion of the viral surface proteins (HBs) into the supernatant (FIG. 24E) was unaffected even at 20 µM βTJ. The HBs data are particularly important because this assay measures secretion of HBs between the last medium change and harvesting of the cells (days 3 and 4 post-transfection), eliminating the possibility that the inventors were detecting residual viral proteins that had been produced early in the experiment. Together, the HBc and HBs accumulation data demonstrate that viral protein production was unaffected despite the declining health of the cells at the higher βTJ doses late in the experiment. Second, toxicity in βTJ-treated cells was much lower when cell death was measured by detecting rupture of the plasma membrane (FIG. 25A). This indicates that the detrimental effects of βTJ on cellular metabolism had not progressed to the point where cells were dying and detaching from the plate at the end of the replication assay. Third, the key feature of our Southern blot assay is that it specifically measures the effect of RNAseH activity during viral replication by detecting RNA:DNA heteroduplexes. Comparing the patterns of HBV DNAs in mock-treated and RNAseH-treated aliquots of each HBV nucleic acid preparation reveals the presence of heteroduplexes regardless of the total yield of viral nucleic acids.

The HBV replication assays in FIGS. 24A-E also measured the total yield of viral DNAs in the cultures, as reflected by the net intensity of the Southern blot signal. Part of the reduction in yield of HBV DNAs at high βTJ concentrations may have been due to impaired function of the cells from βTJ toxicity, but part of the loss was also due to inefficient elongation of the minus-polarity DNA strand and lack of synthesis of the plus-polarity DNA strand in the absence of RNAseH activity (FIGS. 24A and 24D D702A samples, and (Chen and Marion, 1996; Chen et al., 1994; Gerelsaikhan et al., 1996)).

The $EC_{50}$ of βTJ against HBV replication (~5 μM) and its $CC_{50}$ by the MTS assay (10.1 μM) were similar in Huh7 cells. This precludes use of βTJ in humans, especially in a long-term treatment regimen such as would be envisioned for anti-HBV therapy. Therefore, chemical optimization will be needed if tropolone compounds are to be developed into anti-HBV drugs. Seven variants of the core hydroxylated tropolone moiety in βTJ have been tested against the HIV RNAseH (Budihas et al., 2005). Two compounds in addition to βTJ inhibited the RNAseH (α-thuaplicin and manicol) with $IC_{50}$ values of 50 and 60 μM, respectively; the remaining compounds had $IC_{50}$ values >100 μM. Subsequent derivatization of manicol identified 14 α-tropolones with $IC_{50}$ values against HIV <2.0 μM (Chung et al., 2011). Importantly, all of these compounds were less cytotoxic than either βTJ or manicol, and 12 of them could inhibit HIV replication in culture. These precedents with tropolone compounds imply that it may be possible to improve efficacy of βTJ against HBV and reduce its cytotoxicity through chemical derivatization.

The anti-HBV nucleos(t)ide analog drugs are extremely effective at suppressing viremia, and it is very unlikely that a derivative of βTJ would exceed their efficacy as a monotherapy. The clinical potential of βTJ derivatives therefore depends on their ability to work either additively or synergistically with drugs that act through other mechanisms. βTJ presumably inhibits the HBV RNAseH by binding to the enzyme's active site, as has been demonstrated for its effect against the HIV RNAseH (Beilhartz et al., 2009; Farias et al., 2011; Himmel et al., 2009). Binding of the nucleos(t)ide analogs and RNAseH inhibitors to different domains of the HBV polymerase indicates that additive or synergistic action with the nucleos(t)ide analogs against HBV replication is plausible. A precedent with HIV for simultaneous action by βTJ and an inhibitor of the DNA polymerase activity exists because βTJ acts synergistically with calanolide A, a non-nucleoside inhibitor of DNA synthesis by the HIV reverse transcriptase (Budihas et al., 2005).

Employing RNAseH inhibitors in combination with the nucleos(t)ide analogs would have two clinical benefits if they work additively or synergistically with the existing drugs. First, combining nucleos(t)ide analog and anti-RNAseH drugs may suppress HBV replication enough to eliminate HBV from more patients than is currently possible. Second, if HBV RNAseH inhibitors can be produced inexpensively, they could be combined with the inexpensive anti-HBV drug lamivudine. Long-term efficacy of lamivudine treatment is limited because resistance mutations appear in ~20% of patients in the first year and in ~80% after five years (Shaw et al., 2006; Zoulim and Locamini, 2009). However, lamivudine monotherapy is still widely used in many parts of the world because it is the only drug many patients can afford. Combining lamivudine plus an RNAseH inhibitor would be predicted more effectively suppress viral replication than either drug could achieve alone, and this would slow development of resistance against both lamivudine and the RNAseH inhibitor. Slowing evolution of resistant HBV variants would prolong window of efficacy for these low-cost therapies and have a major impact on hepatitis B in resource-limiting settings.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods, and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

G. REFERENCES

The following references, to the extent that they provide exemplary procedural or other details supplementary to those set forth herein, are specifically incorporated herein by reference:

Agrawal et al, *ProcNatlAcadSci USA* 109: 2251-2256, 2012
Ariyoshi et al, *Cell* 78: 1063-1072, 1994
Arnold et al, *JBiolChem* 274: 37060-37069, 1999
Beck and Nassal, *JBiolChem* 278: 36128-36138, 2003
Beilhartz et al., J Mol Biol 388, 462-474, 2009.
Billamboz et al, *JMedChem* 54: 1812-1824, 2011
Billamboz et al, *JMedChem* 51: 7717-7730, 2008
Bokesch et al, *JNatProd* 71: 1634-1636, 2008
Braunshofer-Reiter et al., *ProcNatlAcadSciUSA* 95: 12872-12877, 1998
Braunshofer-Reiter et al., *BiolChem* 379: 1407-1412, 1998.
Budihas et al, *Nucleic Acids Res* 33: 1249-1256, 2005
Buti et al, *JHepatol* 51: 640-646, 2009
Cao et al, *JViral Hepat* 18: 349-357, 2011
Chang et al, *JVirol* 64: 5553-5558, 1990
Chang et al, *JVirol* 68: 5225-5231, 1994
Chen et al, *JVirol* 68: 5232-5238, 1994
Chen et al, *JVirol* 79: 3016-3027, 2005
Chen et al, *ProcNatlAcadSci USA* 101: 14913-14918, 2004
Chen and Marion, *J Virol.* 70, 6151-6156, 1996.
Cheng et al, *JMedVirol* 83: 602-607, 2011
Cheng et al, *JHepatol* 43: 465-471, 2005
Choi et al, *Antiviral Res* 55: 279-290, 2002
Chung et al, *Chemother* 54: 3913-3921, 2010
Chung et al, *JMedChem* 54: 4462-4473, 2011
Coffin et al, *JViral Hepat* 18: 415-423, 2011
Cox and Tillmann, *ExpertOpinEmergDrugs* 16: 713-729, 2011
Di et al, *BioorgMedChemLett* 20: 398-402, 2010
Didierjean et al, *Chemother* 49: 4884-4894, 2005
Dyda et al, *Science* 266: 1981-1986, 1994
Edward et al, *JChemEngData* 33: 538-540, 1998
Farias et al., *Antimicrob Agents Chemother* 55, 4735-4741, 2011.
Foster et al, *ProcNatlAcadSciUSA* 88: 2888-2892, 1991
Frank et al, *ProcNatlAcadSciUSA* 95: 12872-12877, 1998
Frank et al, *BiolChem* 379: 1407-1412, 1998
Freed and Martin, *Fields Virology Philadelphia:* 2107-2185, 2007
Fuji et al, *JMedChem* 52: 1380-1387, 2009
Ganem et al, *NEnglJMed* 350: 1118-1129, 2004
Gerelsaikhan et al, *JVirol* 70: 4269-4274, 1996
Ghany and Liang, *Gastroenterology* 132: 1574-1585, 2007
Goedken and Marqusee, *JBiolChem* 276: 7266-7271, 2001
Gong et al, *BMC Microbiology* 1: 12, 2001
Gong et al, *Chem Biol Drug Des* 77: 39-47, 2011
Hickman et al., *Science* 266: 1981-1986, 1994
Himmel et al, *Structure* 17: 1625-1635, 2009

Himmel et al, *ACS ChemBiol* 1: 702-712, 2006
Hostomsky et al, *Cold Spring Harbor Laboratory Press* pp 341-376, 1993
Hostomsky et al., *Structure* 3:131-134, 1993.
Hu and Anselmo, *JVirol* 74: 11447-11455, 2000
Hu and Seeger, *ProcNatlAcadSciUSA* 93: 1060-1064, 1996
Hu et al, *EMBO J* 16: 59-68, 1997
Katayanagi et al, *Nature* 347: 306-309, 1990
Keck et al, *JBiolChem* 273: 34128-34133, 1998
Kirschberg et al, *JMedChem* 52: 5781-5784, 2009
Klarmann et al, *AIDS Rev* 4: 183-194, 2002
Klumpp and Mirzadegan, *CurrPharmDes* 12: 1909-1922, 2006
Klumpp et al, *Nucleic Acids Res* 31: 6852-6859, 2003
Kramvis et al, *Vaccine* 23: 2409-2423, 2005
Kurbanov et al, *HepatolRes* 40: 14-30, 2010
Kwon and Lok, *NatRevGastroenterolHepatol* 8: 275-284, 2011
Lai et al, *Structure* 8: 897-904, 2000
Lanford et al, *JVirol* 69: 4431-4439, 1995
Lau, *Gastroenterology* 136: 1830-1832, 2009
Lavanchy et al, *J Viral Hepat* 11: 97-107, 2004
Lee et al, *BiochemBiophysResCommun* 233: 401-407, 1997
Levrero et al, *JHepatol* 51: 581-592, 2009
Li et al, *Mol Biol Evol* 12: 657-670, 1995
Liaw et al *Liver Int* 31 *Suppl* 1: 117-121, 2011
Lima et al, *Methods Enzymol* 341: 430-440, 2001
Lima et al, *MolPharmacol* 71: 83-91, 2007
Lin et al, *JVirol* 82: 5703-5714, 2008
Lui et al, *AntivirTher* 15: 145-155, 2010
Marcellin et al, *NEnglJMed* 359: 2442-2455, 2008
McClure, *Cold Spring Harbor Laboratory Press.* 425-444, 1993
Michailidis et al, *Int J Biochem Cell Biol* 44: 1060-1071, 2012
Monto et al, *AmJGastroenterol* 105: 989-1004, 2010
Nowotny and Yang, *EMBO J* 25: 1924-1933, 2006
Nowotny et al, *Cell* 121: 1005-1016, 2005
Op den Brouw, et al, *Immunology* 126: 280-289, 2009
Parker et al, *EMBO J* 23: 4727-4737, 2004
Pelletier et al, *Biochemistry* 35: 12762-12777, 1996
Perrillo and Marcellin, *AntivirTher* 15: 13-22, 2010
Poch et al, *EMBO J* 8: 3867-3874, 1998
Potenza et al, *Protein ExprPurif* 55: 93-99, 2007
Radziwill et al, *JVirol* 64: 613-620, 1990
Radziwill et al, *Virology* 163: 123-132, 1988
Rice and Baker, *NatStructBiol* 8: 302-307, 2001
Ruggeri et al, *Health Policy* 102: 72-80, 2011
Seeger et al, *Fields Virology* 2977-3029, 2007
Shaw et al., *J. Hepatol.* 44, 593-606, 2006.
Shaw-Reid, et al, *JBiolChem* 278: 2777-2780, 2003
Shepard et al, *EpidemiolRev* 28: 112-125, 2006
Song et al, *Science* 305: 1434-1437, 2004
Sorrell et al, *AnnInternMed* 150: 104-110, 2009.
Steitz, *Structure* 3: 131-134, 1995
Sturmer et al, *MedMicrobiolImmunol* 198: 147-155, 2009
Su et al, *JVirol* 84: 7625-7633, 2010
Suchaud et al, *BioorgMedChemLett* 22: 3988-3992, 2012
Takada, et al, *JNatProd* 70: 1647-1649, 2007
Tavis and Badtke, *Springer Science+Business Media, LLC* pp 129-143, 2009
Tavis and Ganem, *ProcNatlAcadSciUSA* 90: 4107-4111, 1993
Tavis et al, *JVirol* 72: 5789-5796, 1998
Tavis et al., *PLoS pathogens* 9, e1003125, 2013.
Tuttleman et al, *Cell* 47: 451-460, 1986
Van Bommel et al, *Hepatology* 51: 73-80, 2010
Vanlandschoot et al, *JGenVirol* 83: 1281-1289, 2002
Vartanian et al, *Nucleic Acids Res* 24: 2627-2631, 1996
Wang et al, *PLoSPathog* 6: e1000986, 2010
Wei et al, *JVirol* 70: 6455-6458, 1996
Wei et al, *JBiolChem* 271: 32617-32622, 1996
Wendeler et al, *ACS ChemBiol* 3: 635-644, 2008
Werle-Lapostolle, et al, *Gastroenterology* 126: 1750-1758, 2004
Williams et al, *BioorgMedChemLett* 20: 6754-6757, 2010
Woltman et al, *PLoS ONE* 6: e15324, 2011
Wong et al, *AntivirTher* 11: 909-916, 2006
Woo et al, *Gastroenterology* 139: 1218-1229, 2010
Wu et al, *Hepatology* 49: 1132-1140, 2009
Wu et al, *JGenVirol* 88: 3260-3269, 2007
Wursthom et al, *Hepatology* 52: 1611-1620, 2010
Xu et al, *MolImmunol* 46: 2640-2646, 2009
Yang and Steitz, *Structure* 3: 131-134, 1995
Yang et al, *Science* 249: 1398-1405, 1990
Zoulim and Locamini, *Gastroenterology* 137: 1593-1608, 2009
Zoulim, *Antiviral Res* 71: 206-215, 2006
Zoulim, *AntivirChemChemother* 15: 299-305, 2004
Zu Putlitz et al, *JVirol* 73: 4188-4196, 1999

What is claimed:

1. A method of inhibiting a hepatitis B virus (HBV) RNAseH comprising contacting said enzyme with a compound having the formula:

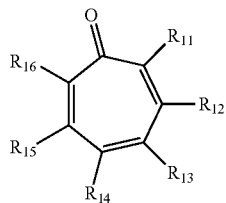

FORMULA III wherein:

$R_{11}$ is hydrogen, —$OR_{17}$, hydroxy, or halo, wherein $R_{17}$ is $C_1$-$C_8$ acyl, $C_1$-$C_8$ alkyl, or a substituted version of either of these groups;

$R_{12}$ is hydrogen, hydroxy or halo;

$R_{13}$ and $R_{14}$ are each independently hydrogen, hydroxy, nitroso, $C_1$-$C_{12}$ alkyl, $C_1$-$C_{12}$ alkenyl, $C_1$-$C_{12}$ alkynyl, $C_1$-$C_{12}$ aryl, $C_1$-$C_{12}$ aralkyl, $C_1$-$C_{12}$ amido, a substituted version of any of these groups, or $R_{13}$ is taken together with $R_{14}$ as provided below;

$R_{15}$ is hydrogen, $C_1$-$C_{12}$ alkyl, $C_1$-$C_{12}$ alkenyl, $C_1$-$C_{12}$ alkynyl, $C_1$-$C_{12}$ aryl, $C_1$-$C_{12}$ aralkyl,

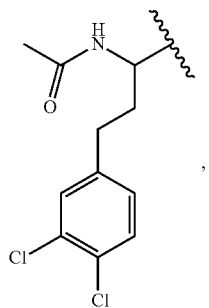 [SMILES: *C(CCc1ccc(Cl)c(Cl)c1)NC(C)=O]

, or a substituted version of any of these groups; and $R_{16}$ is hydrogen, unsubstituted $C_1$-$C_6$ alkyl, substituted $C_1$-$C_6$ alkyl, or hydroxyl;

provided that when $R_{13}$ and $R_{14}$ are taken together as further defined by FORMULA IV:

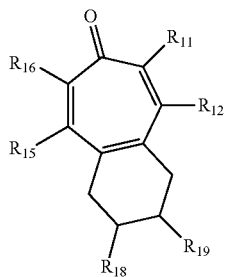

FORMULA IV $R_{18}$ and $R_{19}$ are each independently hydrogen, $C_1$-$C_6$ alkyl, $C_1$-$C_6$ alkenyl, $C_1$-$C_6$ alkynyl.

2. The method of claim 1, wherein the compound is of FORMULA III and $R_{11}$ is hydroxy.

3. The method of claim 1, wherein the compound is of FORMULA III and at least one of $R_{12}$, $R_{13}$, $R_{14}$ or $R_{15}$ is $C_1$-$C_{12}$-alkyl.

4. The method of claim 1, wherein the compound is of FORMULA IV and $R_{18}$ is $C_1$-$C_6$ alkenyl.

5. The method of claim 1, further comprising contacting said enzyme with a second inhibitor of RNAse enzyme activity.

6. The method of claim 5, wherein said second inhibitor is a nucleoside analog.

7. The method of claim 1, further comprising contacting said enzyme with said compound a second time.

8. The method of claim 1, wherein said enzyme is located in a cell.

9. The method of claim 8, wherein said cell is located in vitro.

10. The method of claim 8, wherein said cell is located in a living subject.

11. The method of claim 10, wherein said subject is a mammal infected with HBV.

12. The method of claim 11, wherein said compound is administered intravenously, intra-arterially, orally, or subcutaneously.

13. The method of claim 11, wherein said subject is further administered a second inhibitor of RNAse enzyme activity.

14. The method of claim 13, wherein said second inhibitor is a nucleoside analog.

15. The method of claim 13, wherein said second inhibitor is administered to said subject before or after said compound.

16. The method of claim 13, wherein said second inhibitor is administered to said subject at the same time as said compound.

17. The method of claim 10, wherein said subject has previously received a first-line HBV therapy.

18. The method of claim 17, wherein said HBV has developed resistance to said first-line HBV therapy.

19. The method of claim 11, wherein said subject is administered interferon or pegylated interferon.

20. The method of claim 1, wherein the compound is further defined as:

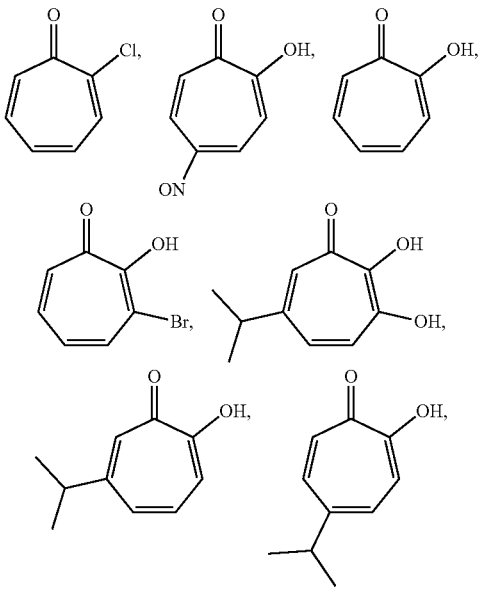

79
-continued
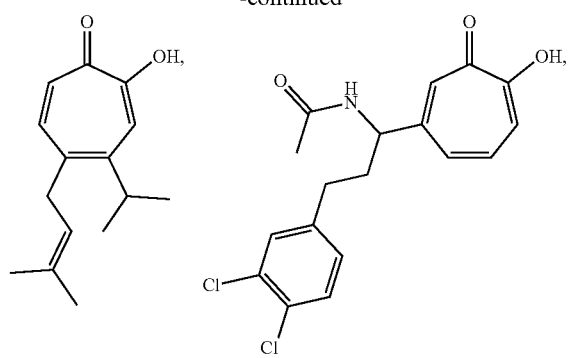
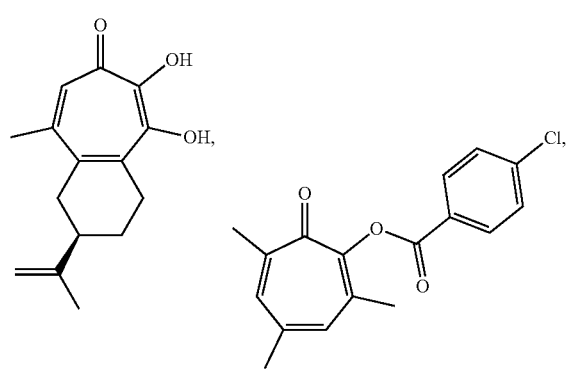
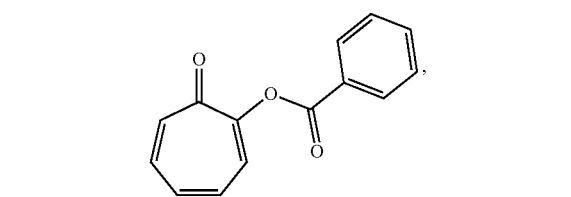
80
-continued
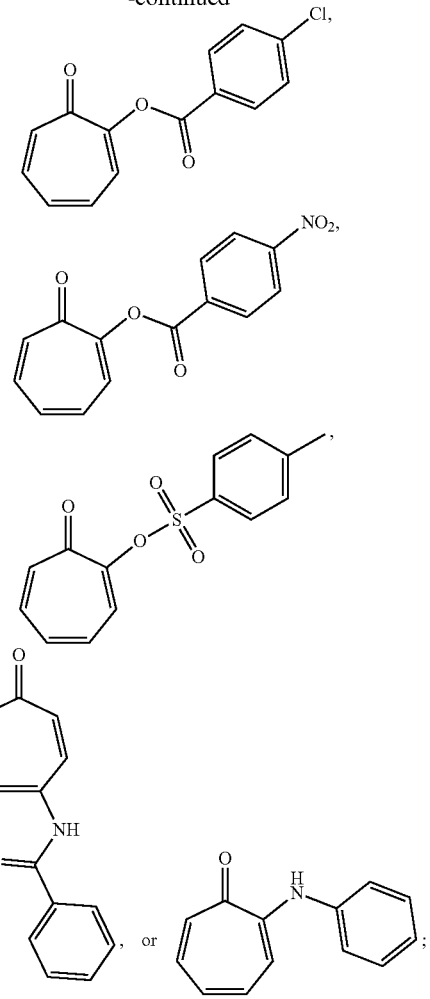
or a pharmaceutically acceptable salt thereof.
* * * * *

SEQUENCE LISTING

<160> NUMBER OF SEQ ID NOS: 19

<210> SEQ ID NO 1
<211> LENGTH: 171
<212> TYPE: PRT
<213> ORGANISM: Artificial
<220> FEATURE:
<223> OTHER INFORMATION: HRHLP genotype A

<400> SEQUENCE: 1

Met Asn Leu Tyr Pro Val Ala Arg Gln Arg Pro Gly Leu Cys Gln Val
1               5                   10                  15

Phe Ala Asp Ala Thr Pro Thr Gly Trp Gly Leu Ala Ile Gly His Gln
            20                  25                  30

Arg Met Arg Gly Thr Phe Val Ala Pro Leu Pro Ile His Thr Ala Glu
        35                  40                  45

Leu Leu Ala Ala Cys Phe Ala Arg Ser Arg Ser Gly Ala Lys Leu Ile

```
                    50                  55                  60
Gly Thr Asp Asn Ser Val Val Leu Ser Arg Lys Tyr Thr Ser Phe Pro
 65                  70                  75                  80

Trp Leu Leu Gly Cys Thr Ala Asn Trp Ile Leu Arg Gly Thr Ser Phe
                 85                  90                  95

Val Tyr Val Pro Ser Ala Leu Asn Pro Ala Asp Asp Pro Ser Arg Gly
            100                 105                 110

Arg Leu Gly Leu Ser Arg Pro Leu Leu Arg Leu Pro Phe Gln Pro Thr
        115                 120                 125

Thr Gly Arg Thr Ser Leu Tyr Ala Val Ser Pro Ser Val Pro Ser His
    130                 135                 140

Leu Pro Val Arg Val His Phe Ala Ser Pro Leu His Val Ala Trp Arg
145                 150                 155                 160

Pro Pro Gly Ala Gly His His His His His
                165                 170

<210> SEQ ID NO 2
<211> LENGTH: 171
<212> TYPE: PRT
<213> ORGANISM: Artificial
<220> FEATURE:
<223> OTHER INFORMATION: HRHLP genotype B

<400> SEQUENCE: 2

Met Asn Leu Tyr Pro Val Ala Arg Gln Arg Pro Gly Leu Cys Gln Val
  1               5                  10                  15

Phe Ala Asp Ala Thr Pro Thr Gly Trp Gly Leu Ala Ile Gly His Gln
             20                  25                  30

Arg Met Arg Gly Thr Phe Val Ser Pro Leu Pro Ile His Thr Ala Glu
         35                  40                  45

Leu Leu Ala Ala Cys Phe Ala Arg Ser Arg Ser Gly Ala Lys Leu Ile
     50                  55                  60

Gly Thr Asp Asn Ser Val Val Leu Ser Arg Lys Tyr Thr Ser Phe Pro
 65                  70                  75                  80

Trp Leu Leu Gly Cys Ala Ala Asn Trp Ile Leu Arg Gly Thr Ser Phe
                 85                  90                  95

Val Tyr Val Pro Ser Ala Leu Asn Pro Ala Asp Asp Pro Ser Arg Gly
            100                 105                 110

Arg Leu Gly Leu Tyr Arg Pro Leu Leu Arg Leu Pro Tyr Arg Pro Thr
        115                 120                 125

Thr Gly Arg Thr Ser Leu Tyr Ala Asp Ser Pro Ser Val Pro Ser Arg
    130                 135                 140

Leu Pro Asp Arg Val His Phe Ala Ser Pro Leu His Val Ala Trp Arg
145                 150                 155                 160

Pro Pro Gly Ala Gly His His His His His
                165                 170

<210> SEQ ID NO 3
<211> LENGTH: 171
<212> TYPE: PRT
<213> ORGANISM: Artificial
<220> FEATURE:
<223> OTHER INFORMATION: HRHLP genotype C

<400> SEQUENCE: 3

Met Asn Leu Tyr Pro Val Ala Arg Gln Arg Ser Gly Leu Cys Gln Val
  1               5                  10                  15
```

```
Phe Ala Asp Ala Thr Pro Thr Gly Trp Gly Leu Ala Ile Gly His Gln
             20                  25                  30

Arg Met Arg Gly Thr Phe Val Ala Pro Leu Pro Ile His Thr Ala Glu
         35                  40                  45

Leu Leu Ala Ala Cys Phe Ala Arg Ser Arg Ser Gly Ala Lys Leu Ile
     50                  55                  60

Gly Thr Asp Asn Ser Val Val Leu Ser Arg Lys Tyr Thr Ser Phe Pro
65                  70                  75                  80

Trp Leu Leu Gly Cys Ala Ala Asn Trp Ile Leu Arg Gly Thr Ser Phe
                 85                  90                  95

Val Tyr Val Pro Ser Ala Leu Asn Pro Ala Asp Asp Pro Ser Arg Gly
            100                 105                 110

Arg Leu Gly Ile Tyr Arg Pro Leu Leu Arg Leu Pro Phe Arg Pro Thr
        115                 120                 125

Thr Gly Arg Thr Ser Leu Tyr Ala Asp Ser Pro Ser Val Pro Ser His
    130                 135                 140

Leu Pro Asp Arg Val His Phe Ala Ser Pro Leu His Val Ala Trp Arg
145                 150                 155                 160

Pro Pro Gly Ala Gly His His His His His His
                165                 170

<210> SEQ ID NO 4
<211> LENGTH: 172
<212> TYPE: PRT
<213> ORGANISM: Artificial
<220> FEATURE:
<223> OTHER INFORMATION: HRHLP genotype D

<400> SEQUENCE: 4

Met Asn Leu Tyr Pro Val Ala Arg Gln Met Arg Pro Gly Leu Cys Gln
1               5                   10                  15

Val Phe Ala Asp Ala Thr Pro Thr Gly Trp Gly Leu Val Met Gly His
             20                  25                  30

Gln Arg Met Arg Gly Thr Phe Ser Ala Pro Leu Pro Ile His Thr Ala
         35                  40                  45

Glu Leu Leu Ala Ala Cys Phe Ala Arg Ser Arg Ser Gly Ala Asn Ile
     50                  55                  60

Ile Gly Thr Asp Asn Ser Val Val Leu Ser Arg Lys Tyr Thr Ser Phe
65                  70                  75                  80

Pro Trp Leu Leu Gly Cys Ala Ala Asn Trp Ile Leu Arg Gly Thr Ser
                 85                  90                  95

Phe Val Tyr Val Pro Ser Ala Leu Asn Pro Ala Asp Asp Pro Ser Arg
            100                 105                 110

Gly Arg Leu Gly Leu Ser Arg Pro Leu Leu Arg Leu Pro Phe Arg Pro
        115                 120                 125

Thr Thr Gly Arg Thr Ser Leu Tyr Ala Asp Ser Pro Ser Val Pro Ser
    130                 135                 140

His Leu Pro Asp Arg Val His Phe Ala Ser Pro Leu His Val Ala Trp
145                 150                 155                 160

Arg Pro Pro Gly Ala Gly His His His His His
                165                 170

<210> SEQ ID NO 5
<211> LENGTH: 171
<212> TYPE: PRT
<213> ORGANISM: Artificial
<220> FEATURE:
```

<223> OTHER INFORMATION: HRHLP genotype H

<400> SEQUENCE: 5

Met Asn Leu Tyr Pro Val Ala Arg Gln Arg Pro Gly Leu Cys Gln Val
1               5                   10                  15

Phe Ala Asp Ala Pro Pro Thr Gly Trp Gly Leu Ala Ile Gly His Gln
            20                  25                  30

Arg Met Arg Gly Thr Phe Val Ala Pro Leu Pro Ile His Thr Ala Glu
        35                  40                  45

Leu Leu Ala Ala Cys Phe Ala Arg Ser Arg Ser Gly Ala Asp Ile Ile
    50                  55                  60

Gly Thr Asp Asn Ser Val Val Leu Ser Arg Lys Tyr Thr Ser Phe Pro
65                  70                  75                  80

Trp Leu Leu Gly Cys Ala Ala Asn Trp Ile Leu Arg Gly Thr Ser Phe
                85                  90                  95

Val Tyr Val Pro Ser Ala Leu Asn Pro Ala Asp Asp Pro Ser Arg Gly
            100                 105                 110

Arg Leu Gly Leu Cys Arg Pro Leu Leu Arg Leu Pro Phe Arg Pro Thr
        115                 120                 125

Thr Gly Arg Thr Ser Leu Tyr Ala Asp Ser Pro Val Pro Ser His
    130                 135                 140

Leu Pro Ala Arg Val His Phe Ala Ser Pro Leu His Val Ala Trp Arg
145                 150                 155                 160

Pro Pro Gly Ala Gly His His His His His His
                165                 170

<210> SEQ ID NO 6
<211> LENGTH: 11
<212> TYPE: PRT
<213> ORGANISM: Artificial
<220> FEATURE:
<223> OTHER INFORMATION: Synthetic peptide

<400> SEQUENCE: 6

Val Asn Gln Ile Ile Glu Gln Leu Ile Val Lys
1               5                   10

<210> SEQ ID NO 7
<211> LENGTH: 44
<212> TYPE: PRT
<213> ORGANISM: Artificial
<220> FEATURE:
<223> OTHER INFORMATION: Synthetic peptide

<400> SEQUENCE: 7

Val Asn Gln Ile Ile Glu Gln Leu Ile Val Lys Lys Glu Lys Val Tyr
1               5                   10                  15

Leu Ala Trp Val Pro Ala His Lys Gly Ile Gly Gly Asn Glu Gln Val
            20                  25                  30

Asp Lys Leu Val Ser Ala Gly Ile Arg Lys Val Leu
        35                  40

<210> SEQ ID NO 8
<211> LENGTH: 20
<212> TYPE: DNA
<213> ORGANISM: Artificial
<220> FEATURE:
<223> OTHER INFORMATION: Synthetic oligonucleotide

<400> SEQUENCE: 8

```
ccacataggc tatgtggaac                                              20
```

<210> SEQ ID NO 9
<211> LENGTH: 20
<212> TYPE: DNA
<213> ORGANISM: Artificial
<220> FEATURE:
<223> OTHER INFORMATION: Synthetic oligonucleotide

<400> SEQUENCE: 9

```
gttccacata gcctatgtgg                                              20
```

<210> SEQ ID NO 10
<211> LENGTH: 23
<212> TYPE: DNA
<213> ORGANISM: Artificial
<220> FEATURE:
<223> OTHER INFORMATION: Synthetic oligonucleotide

<400> SEQUENCE: 10

```
ccgcctgatt ggacggcttt tcc                                          23
```

<210> SEQ ID NO 11
<211> LENGTH: 31
<212> TYPE: DNA
<213> ORGANISM: Artificial
<220> FEATURE:
<223> OTHER INFORMATION: Synthetic oligonucleotide

<400> SEQUENCE: 11

```
gcaactgtgt cgacagcagc tccgaaggag a                                 31
```

<210> SEQ ID NO 12
<211> LENGTH: 41
<212> TYPE: DNA
<213> ORGANISM: Artificial
<220> FEATURE:
<223> OTHER INFORMATION: Synthetic oligonucleotide

<400> SEQUENCE: 12

```
ccacauaggc uauguggaac ttttgttcca catagcctat g                      41
```

<210> SEQ ID NO 13
<211> LENGTH: 22
<212> TYPE: DNA
<213> ORGANISM: Artificial
<220> FEATURE:
<223> OTHER INFORMATION: Synthetic oligonucleotide

<400> SEQUENCE: 13

```
ggaggctgta ggcataaatt gg                                           22
```

<210> SEQ ID NO 14
<211> LENGTH: 25
<212> TYPE: DNA
<213> ORGANISM: Artificial
<220> FEATURE:
<223> OTHER INFORMATION: Synthetic oligonucleotide

<400> SEQUENCE: 14

```
agatgattag gcagaggtga aaaag                                        25
```

<210> SEQ ID NO 15
<211> LENGTH: 9
<212> TYPE: DNA
<213> ORGANISM: Artificial

```
<220> FEATURE:
<223> OTHER INFORMATION: Synthetic oligonucleotide

<400> SEQUENCE: 15 ctgcgcacc                                                                                   9

<210> SEQ ID NO 16
<211> LENGTH: 11
<212> TYPE: DNA
<213> ORGANISM: Artificial
<220> FEATURE:
<223> OTHER INFORMATION: Synthetic oligonucleotide

<400> SEQUENCE: 16
agcaccatgc a                                                                                11

<210> SEQ ID NO 17
<211> LENGTH: 162
<212> TYPE: PRT
<213> ORGANISM: Hepatitis B virus

<400> SEQUENCE: 17
```

Met Asn Leu Tyr Pro Val Ala Arg Gln Arg Pro Gly Leu Cys Gln Val
1               5                   10                  15

Phe Ala Asp Ala Thr Pro Thr Gly Trp Gly Leu Val Met Gly His Gln
            20                  25                  30

Arg Met Arg Gly Thr Phe Ser Ala Pro Leu Pro Ile His Thr Ala Glu
        35                  40                  45

Leu Leu Ala Ala Cys Phe Ala Arg Ser Arg Ser Gly Ala Asn Ile Ile
    50                  55                  60

Gly Thr Asp Asn Ser Val Val Leu Ser Arg Lys Tyr Thr Ser Phe Pro
65                  70                  75                  80

Trp Leu Leu Gly Cys Ala Ala Asn Trp Ile Leu Arg Gly Thr Ser Phe
                85                  90                  95

Val Tyr Val Pro Ser Ala Leu Asn Pro Ala Asp Asp Pro Ser Arg Gly
            100                 105                 110

Arg Leu Gly Leu Ser Arg Pro Leu Leu Arg Leu Pro Phe Arg Pro Thr
        115                 120                 125

Thr Gly Arg Thr Ser Leu Tyr Ala Asp Ser Pro Ser Val Pro Ser His
    130                 135                 140

Leu Pro Asp Arg Val His Phe Ala Ser Pro Leu His Val Ala Trp Arg
145                 150                 155                 160

Pro Pro

```
<210> SEQ ID NO 18
<211> LENGTH: 120
<212> TYPE: PRT
<213> ORGANISM: Human immunodeficiency virus type 1

<400> SEQUENCE: 18
```

Tyr Val Asp Gly Ala Ala Asn Arg Glu Thr Lys Leu Gly Lys Ala Gly
1               5                   10                  15

Tyr Val Thr Asn Arg Gly Arg Gln Lys Val Val Thr Leu Thr Asp Thr
            20                  25                  30

Thr Asn Gln Lys Thr Glu Leu Gln Ala Ile Tyr Leu Ala Leu Gln Asp
        35                  40                  45

Ser Gly Leu Glu Val Asn Ile Val Thr Asp Ser Gln Tyr Ala Leu Gly
    50                  55                  60

-continued

```
Ile Ile Gln Ala Gln Pro Asp Gln Ser Glu Ser Glu Leu Val Asn Gln
 65                  70                  75                  80

Ile Ile Glu Gln Leu Ile Lys Lys Glu Lys Val Tyr Leu Ala Trp Val
                 85                  90                  95

Pro Ala His Lys Gly Ile Gly Gly Asn Glu Gln Val Asp Lys Leu Val
            100                 105                 110

Ser Ala Gly Ile Arg Lys Val Leu
        115                 120

<210> SEQ ID NO 19
<211> LENGTH: 288
<212> TYPE: PRT
<213> ORGANISM: Human immunodeficiency virus type 1

<400> SEQUENCE: 19

Phe Leu Asp Gly Ile Asp Lys Ala Gln Asp Glu His Glu Lys Tyr His
  1               5                  10                  15

Ser Asn Trp Arg Ala Met Ala Ser Asp Phe Asn Leu Pro Pro Val Val
                 20                  25                  30

Ala Lys Glu Ile Val Ala Ser Cys Asp Lys Cys Gln Leu Lys Gly Glu
             35                  40                  45

Ala Met His Gly Gln Val Asp Cys Ser Pro Gly Ile Trp Gln Leu Asp
         50                  55                  60

Cys Thr His Leu Glu Gly Lys Val Ile Leu Val Ala Val His Val Ala
 65                  70                  75                  80

Ser Gly Tyr Ile Glu Ala Glu Val Ile Pro Ala Glu Thr Gly Gln Glu
                 85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Gly Ala Thr Val Arg Ala
        115                 120                 125

Ala Cys Trp Trp Ala Gly Ile Lys Gln Glu Phe Gly Ile Pro Tyr Asn
130                 135                 140

Pro Gln Ser Gln Gly Val Val Glu Ser Met Asn Lys Glu Leu Lys Lys
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285
```